(12) United States Patent
Tomich et al.

(10) Patent No.: US 8,163,870 B2
(45) Date of Patent: Apr. 24, 2012

(54) CHANNEL FORMING PEPTIDES

(75) Inventors: John M. Tomich, Manhattan, KS (US); Iwamoto Takeo, Manhattan, KS (US); James R. Broughman, Houston, TX (US); Bruce D. Schultz, Wamego, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 1847 days.

(21) Appl. No.: 10/867,431

(22) Filed: Jun. 14, 2004

(65) Prior Publication Data

US 2007/0298494 A1 Dec. 27, 2007

Related U.S. Application Data

(63) Continuation-in-part of application No. 09/710,419, filed on Nov. 9, 2000, now Pat. No. 6,750,200.

(60) Provisional application No. 60/569,299, filed on May 7, 2004.

(51) Int. Cl.
*C07K 14/00* (2006.01)
(52) U.S. Cl. .................................. 530/300; 530/350
(58) Field of Classification Search .................... None
See application file for complete search history.

(56) References Cited

U.S. PATENT DOCUMENTS

| 5,368,712 | A | | 11/1994 | Tomich et al. | |
|---|---|---|---|---|---|
| 5,922,840 | A | | 7/1999 | Tomich et al. | |
| 6,077,826 | A | * | 6/2000 | Tomich et al. | 514/12 |

FOREIGN PATENT DOCUMENTS

WO WO9726905 7/1997

OTHER PUBLICATIONS

Broughman, J.R., K. Mitchell, T. Iwamoto, B.D. Schultz, and J.M. Tomich. Amino-terminal Modification of a Channel-forming Peptide Increases Capacity for Epithelial Anion Secretion. *Am. J. Physiol: (Cell Physiol.)* 280; C451-C458, 2001.
Esposito, G., B. Dhanapal, P. Dumy, V. Varma, M. Mutter, and G. Bodenhausen. Lysine as Helix C-capping Residue in a Synthetic Peptide. *Biopolymers* 41, 27-35 (1997).
Gao, L., J.R. Broughman, T. Iwamoto, J.M. Tomich, C.J> Venglarik, J.J. Forman. Synthetic Chloride Channel Restores Glutathione Secretion in Cystic Fibrosis Airway Epithelia. *Am. J. Physiol. Lung Cell Mol. Physiol.* 281:L24-L30, 2001.
Mitchell, K.E., J.M. Tomich, T. Iwamoto, and L.C. Freeman. A Synthetic Peptide Based on a Glycine-gated Chloride Channel Induces a Novel Chloride Conductance in Isolated Epithelial Cells. *Biochim. Biophys. Acta* 1466, 47-60 (2000).
Reddy, L.G., T. Iwamoto, J.M. Tomich, and M. Montal. Synthetic Peptides and Four-helix Bundle Proteins as Model Systems for the Pore-forming Structure of Channel Proteins. II. Transmembrane Segment M2 of the Brain Glycine Receptor Channel Is a Plausible Candidate for the Pore-lining Structure. *J. Biol. Chem.* 268, 14608-14615 (1993).
Tomich, J.M., D.P. Wallace, K. Henderson, R. Brandt, C.A. Ambler, A.J. Scott, K.E. Mitchell, G. Radke, J.J. Grantham, L.P. Sullivan, and T. Iwamoto. Aqueous Solubilization of Transmembrane Peptide Sequences with Retention of Membrane Insertion and Function. *Biophys J.* 74, 256-267 (1998).
Tomich, J.M. Amphipathic Helices in Channel-Forming Structures. *The Amphipathic Helix* Chap. 9, pp. 221-254 (1993).
Wallace, D.P., J.M. Tomich, T. Iwamoto, K. Henderson, J.J. Grantham, and L.P. Sullivan. A Synthetic Peptide Derived from the Glycine-gated Cl-channel Generates Cl- channel induces transepithelial Cl- and fluid secretion by Epithelial Monolayers. *Am. J. Physiol:* 272 (*Cell Physiol.* 41) C1672-C1679 (1997).
Wallace, D.P., J.M. Tomich, J. Eppler, T. Iwamoto, J.J. Grantham, and L.P. Sullivan. A Synthetic Channel-Forming Peptide Induces Cl-Secretion: Modulation by $Ca^{2+}$ -dependent $K^+$ Channels. *Biochim. Biophys. Acta* 1464, 69-82 (2000).

* cited by examiner

*Primary Examiner* — Michael Pak
(74) *Attorney, Agent, or Firm* — Polsinelli Shughart PC; Tracey S. Truitt

(57) ABSTRACT

The present invention provides a family of peptides based upon the M2GlyR sequence. These peptides are derivatives of the M2GlyR sequence and can be modified at their ends to include a plurality of polar amino acid residues to enhance their solubility. Particularly preferred derivatives include portions of the M2GlyR sequence which are palindromic to another portion of the peptide or to the M2GlyR sequence itself. Preferably these portions are at least 7 amino acid residues in length. Peptides embraced by the present invention are characterized by having greater effects on the transepithelial electrical resistance of cells at lower concentrations. Peptides of the present invention have been shown to increase Isc in MDCK epithelial cell monolayers with half maximal effects observed at or below 30 μM, a nearly 10-fold improvement over any peptide previously characterized in the M2GlyR family. Additionally, peptides of the invention have been shown to increase transepithelial electrical conductance and modulate the permeability of tight junctions in epithelial cells.

12 Claims, 31 Drawing Sheets

$I_{sc}$ in MDCK cell monolayers.
E = 1-EBIO; all numbers represent μM concentrations.
Dotted line is at zero μA.

SEQ ID No. 5
NK4(a-L-a')

$I_{sc}$ in MDCK cell monolayers.
E = 1-EBIO; all numbers represent
µM concentrations.
Dotted line is at zero µA.

SEQ ID No. 19

SEQ ID No. 3
N-K$_4$ M2GlyR in water

SEQ ID No. 2
C-K$_4$ M2GlyR in water

SEQ ID No. 3
N-K₄ M2GlyR
(KKKKPARVGLGITTVLTMTTQSSGSRA)

SEQ ID No. 18
N-K₄ A•L•a
(KKKKAARVGLGITTVLVTTIGLGVRAA)

CHANNEL FORMING PEPTIDES

RELATED APPLICATIONS

This application is a continuation-in-part of application Ser. No. 09/710,419, filed on Nov. 9, 2000 now U.S. Pat. No. 6,750,200 and claims the benefit of Ser. No. 60/569,299, filed on May 7, 2004. The content and teachings of each of these applications is hereby incorporated by reference herein.

SEQUENCE LISTING

A printed Sequence Listing accompanies this application, and has also been submitted with identical contents in the form of a computer-readable ASCII file on a CD-ROM.

BACKGROUND OF THE INVENTION

1. Field of the Invention

The present invention is broadly concerned with multiple-peptide channel assemblies which provide transport of anions through epithelial cell membranes wherein the preferred peptides have from about 16-31 amino acid residues and are soluble in water to a level of at least 5 mM; such channel assemblies can be used in the treatment of diseases such as cystic fibrosis (CF) and adult polycystic kidney disease (APKD). More particularly, the invention pertains to such channel assembly forming peptides, and corresponding methods of use, wherein the peptides are derived from a segment of a native (i.e., naturally occurring) channel protein and have their water solubilities enhanced by modification of the C- or N-ends thereof modified with a plurality of polar amino acid residues such as lysine. The polar amino acids (both DNA coding and non-coding), which are not limited to the all L-stereoconfiguration, include: lysine, arginine, glutamic acid, aspartic acid, diaminopropionic acid, diaminobutyric acid, ornithine, and homolysine. These amino acids are characterized by their ability to adopt different charged states at different pH values. Under physiological conditions, pH 7.2-7.4, the side chain amino (+) or carboxylic acids (−) are in the charged or ionized state. Still more particularly, the invention pertains to derivatives of the M2GlyR sequence, which remain predominantly in monomer form when in solution, have a desired amount of helical configuration, and alter the transepithelial electrical resistance of cell layers to a greater extent than was heretofore possible. Additionally, one aspect of the invention pertains to derivatives of the M2GlyR sequence that modulate the permeability to polar and non-polar solutes across tight junctions that join epithelial cells into a confluent, electrically resistive layer.

2. Description of the Prior Art

Introduction. A major problem in CF is the inability of airway epithelia to secrete fluid. The resulting changes in the composition of the mucous coating the airway epithelia result in infection and subsequent inflammation, scarring, and eventual pulmonary destruction. The basis of the problem is the absence of functional cystic fibrosis transmembrane conductance regulator (CFTR) in the apical membrane of the epithelial cells. This leads to an increase in the absorption of salt and water and an inability to respond to appropriate stimuli by secreting chloride and water. CFTR is an anion channel; in addition it down-regulates sodium channel expression or function and modulates the activity of other ion permeation pathways (e.g., an outwardly rectifying chloride channel (ORCC) and some potassium channels). These properties of CFTR enable the airway cells to secrete chloride and this drives the secretion of sodium and water.

A synthetic-23-residue α-helical peptide designated M2GlyR forms anion-selective channels in phospholipid bilayers. This peptide has the amino acid sequence of the putative transmembrane segment, typically designated M2, of the strychnine-binding α subunit of the glycine receptor.

The origin and properties of M2GlyR. The glycine receptor is a membrane protein present in post-synaptic membranes. Binding of glycine activates a Cl⁻ conducting channel, leading to hyperpolarization of the membrane and inhibition of the synapse. The receptor consists of two major glycopolypeptides, an α subunit of 48 kd and a β subunit of 58 kd, and a receptor-associated cytoplasmic protein of 93 kd. Strychnine, an antagonist of the glycine receptor, binds only to the α subunit. Messenger RNA corresponding to this subunit leads to the expression of functional, glycine-activated, Cl⁻ channels upon injection into *Xenopus* oocytes.

The glycine receptor channel in cultures of embryonic mouse spinal cord is selective for monovalent anions, with conductances of 27 and 46 pS in 145 mM Cl⁻ solution. Pharmacological studies suggested the presence of two sequentially occupied anion binding sites in the channel. These sites are considered to be the functional correlates of the positively charged amino acids bordering the M2 segment of the α subunits. This finding led to the development of the synthetic peptide with the sequence of the M2 segment of the glycine receptor.

Electrical recordings from phospholipid bilayers containing M2GlyR showed single-channel conductances of 25 pS and 49 pS in symmetric 0.5 M KCl with channel open lifetimes in the millisecond range. Single channel events occurred in 0.5 M N-methyl-D-glucamine Cl but not in sodium gluconate, indicating that the channel is anion selective. A transference number for anions of 0.85 was calculated from reversal potential measurements under a 5-fold KCl concentration gradient.

After insertion into the lipid bilayers the monomeric peptides self-assemble to form oligomers that exhibit various amplitudes of ion conductance. To gain control over the aggregate number of monomers that form a functional ion-selective channel, four identical M2GlyR peptide units were tethered to a 9-amino acid carrier template to form a four-helix bundle protein. This tetramer, self-inserted into lipid bilayers, and formed uniform 25 pS channels. The 49 pS conductance described above is presumed to be due to the presence of a pentamer.

The tetrameric channel was blocked by the Cl⁻ channel blockers 9-anthracene carboxylic acid (9-AC) and niflumic acid (NFA). It was not blocked by QX-222, an analogue of lidocaine and a blocker of cation-selective channels. Strychnine, an antagonist of the glycine receptor, does not block the channel-forming tetramer. Strychnine is presumed to bind to the ligand-binding domain of the receptor exposed to the extracellular surface but not to the channel domain.

Structure of channel forming peptides. While great strides have been made in the area of channel function and regulation, using the intact protein or in some cases purified channel proteins reconstituted into model membranes, many aspects of channel function remain unresolved. A K⁺ channel from *streptomyces lividans* was crystallized and the structure determined at 3.2 Angstroms. This structure has served as a model for other ion channels using homology modeling methodologies. This structure, however, is for a 4 subunit channel as opposed to the five subunit channel proposed for the glycine receptor.

Considerable structural data exist for the related class of channel forming peptides (CFPs). Naturally occurring CFPs constitute a class of bioactive peptides. In the present application, the claimed CFPs are peptides that form discrete ion-selective conducting pores rather than sequences such as Magainins which form large non-selective holes in the membrane. These CFPs have channels that are much smaller in size and contain only a ring of short peptide chains organized around the central ion conducting pore in the lipid bilayer. These channels are unique in that they assemble by the oligomerization of a single peptide. These structures are models for studying the structure and function of the various regulated channels that occur in nature. This class of CFPs includes: the α-aminoisobutyric acid-containing channels such as alamethicin and zervamicin, and a number of toxins and venoms such as melittin, cecropins, mast cell degranulating peptides, and the defensins. Melittin is somewhat of a special case because it forms channels only at low concentrations; at higher concentrations it acts as a lytic agent. In some cases CFPs assemble spontaneously upon insertion into the bilayer while in the remaining cases the assembly requires an electrical potential across the membrane ($V_m$).

The structure of the channels arising from the assembly of these peptides vary from trimers to hexadecamers associated in the form of helical bundles or β-barrels. The most widely accepted model that is in accord with the model for channel proteins has the helices arranged with their dipoles all pointing in the same direction (parallel). Since CFP channels, unlike authentic channel proteins, are not generated from the association of large protein subunits, alternative stabilization schemes must be invoked to account for the presence of this higher energy arrangement of parallel segments. These could include aligning the dipoles in response to the presence of the membrane potential and/or an increase in the favorable intermolecular interactions promoted by the parallel assembly. Most CFPs form multiple size bundles of parallel segments (e.g., n=4, 5, 6) that can spontaneously increase or decrease in size upon the addition or deletion of a peptide monomer to or from the channel assembly. These observations imply that enough information is contained in a single channel forming polypeptide to drive the correct folding, assembly, and activity of these channels.

The activity of these assembled molecules, the opening and closing of the channels on the millisecond time scale, has been ascribed to numerous effects. Three different helical motions have been implicated: the bending and twisting of the helices, rigid-body fluctuations of the entire assembled structure with the lipid bilayer, and rotational motions of the polypeptide around its helical axis. Another hypothesis suggests that channel activity is a consequence of a conformational change that is transmitted along the helical axis. Others suggest that the movement of individual amino acid sidechains could provide this function, and one group contends that an electron transfer could disrupt a hydrogen bonding of four tyrosines in $K^+$ channels.

Fluorescence, Fourier transform infrared spectroscopy (FTIR), and circular dichroism (CD) measured in organic solvents, phospholipid micelles, liposomes, or oriented phospholipid bilayers, have been successfully used to probe the solution and membrane-bound conformations of these CFPs. Computer modeling studies have been performed to estimate the energetics of moving an ion across a lipid bilayer through a pore generated by a bundle of transmembrane helices. Structural experiments using NMR are yielding important results. In general, these studies have provided several conclusions concerning the solution behavior and membrane interactions of CFPs. Amphipathic helical peptides can co-exist as monomers and aggregates in solution. Monomers interact much more readily with lipid bilayers and micelles. Depending on the peptide to lipid ratio, type of lipid, ionic strength, solution pH, and lipid hydration, the peptide will preferentially orient itself either parallel to or perpendicular to the plane of the bilayer. Many CFPs do not require a potential difference across the bilayer to insert spontaneously into the bilayer. Once in the membrane, the helices associate in a time- and concentration-dependent manner to form the multistate helical bundles. It is these assemblies that conduct ions across the bilayer. These studies, when considered together, reveal the transmembrane amphipathic helix to be a dynamic structure. The ability to oligomerize in the membrane into stable ring structures, with a central aqueous pore capable of opening and closing, appears to be driven by the asymmetrical alignment of hydrophilic and hydrophobic amino acid residues that seem to obey a unique set of rules.

Putative channel forming segments from large channel proteins behave much like the small naturally occurring CFPs described above. They spontaneously insert into bilayers and self-assemble into an ion-conducting structure, presumably comprised of a parallel array of α-helices. These structures retain biological activities reminiscent of the associated native proteins. These channel-forming structures are reasonable models for exploring both the oligomerization of trans-membrane segments and for defining the molecular events that give rise to channel activity. The beauty of this system emanates from the appearance of a measurable activity (i.e., ion permeation) that arises from the assembly of an amphipathic transmembrane helix. The activity allows measurement of the effects of amino acid substitutions on either the size of the assemblies or the contribution of the residues to ion selectivity or translocation. The number of helices per channel can be precisely controlled, thus preventing multiple oligomerization states, by tethering the helical segments to a peptide backbone during synthesis. The small size of these assemblies makes them ideally suited for NMR structural studies using either detergent micelle solution NMR or oriented bilayer solid-state NMR.

Pharmacological studies have been a relatively recent addition to the single channel analysis of these model CFP channels. Using a four helix bundle CFP derived from the human L-type dihydropyridine sensitive $Ca^{2+}$ channel, the binding of a local anaesthetic as well as a number of calcium channel blockers with binding affinities on the order of those observed for the full length calcium channel protein have been observed. This avenue of investigation adds a sensitive method of discriminating between channels that truly mimic their parent structures as opposed to those that might produce non-discriminating ionic pores. Once the three dimensional structure for one of the synthetic channels has been solved, rational drug design of both channel agonists and antagonists may be attempted using these coordinates.

Membrane proteins are generally acknowledged to be the most difficult class of proteins for detailed structural analysis. The studies presented above clearly demonstrate the utility of working with small synthetic CFPs, as model systems, to study events involved in peptide association with lipid membranes, insertion into membranes, and assembly into ion-conducting oligomers. The amphipathic helix is a suitable structural motif for the pore of channel proteins that also contributes to the organization, size, function, and stabilization of ionic channels. As an assembled structure, these helical bundles can be used to investigate the structure, organization, and function of channels.

Application of synthetic peptides to biological membranes. Extensive evidence indicates that $Cl^-$ secretion drives fluid secretion across Madin-Darby canine kidney (MDCK) cells, across cells cultured from the cystic epithelium of the kidneys of patients with autosomal dominant polycystic kidney disease (APKD), and that a Cl⁻ channel is involved in fluid secretion. Indeed there is now extensive data indicating that CFTR is the channel involved in that secretion by APKD cells. Apparently, a net secretion of Cl⁻ into the lumen of the cysts leads to an increase in water volume in the cysts, ultimately resulting in kidney dysfunction. However, although there is a precedent for the application of synthetic channel-forming peptides to cells, no one previously has used channel-forming peptides to treat symptoms of any disease.

Tight junctions. Epithelial and endothelial cells form monolayers within the body that generate and separate fluid compartments of distinct compositions and protect the interstitial space from environmental factors. These activities are highly desirable in that they allow for physiological function and, in general, are associated with bodily health. However, in numerous pathological states the epithelium or endothelium provides a barrier that precludes therapeutic access to the targeted site. Notably, the intestine is a barrier to drug absorption, the nephron is a barrier to drug retention, and brain vessel endothelium inhibits access of psychoactive and other therapeutic drugs to the brain. Thus, modulation of the epithelial or endothelial barrier function is key to delivering therapy in many life-threatening situations.

The barrier function of epithelial cells is performed by tight junctions: complex, highly regulated, protean structures. The multitude of 'junctional' and associated proteins that participate in the barrier function suggests that one or more of the components might be targeted for therapeutic interventions. Transient openings of these junctions are required for a variety of bodily functions including sperm maturation, extravasation of lymphocytes across endothelia and nutrient uptake associated with activity of the Na⁺/glucose transporter. Pathology associated with aberrant function and dysregulation of the tight junction includes cancer metastases, autoimmune dysfunction, coeliac disease, and inflammatory bowel disease. Tight junctions are targets of bacterial toxins such as the *Vibrio cholerae* zonula occludens toxin (ZOT) and *Clostridium difficile* toxins TcdA and TcdB. Tight junction permeability is tightly regulated (see FIG. 31, adapted from Mitic, L. L., C. M. Van Itallie, and J. M. Anderson. Molecular physiology and pathophysiology of tight junctions I. Tight junction structure and function: lessons from mutant animals and proteins. *Am J Physiol Gastrointest Liver Physiol* 279: G250-4, 2000). The cytoskeleton of actin microfilaments, associated with myosin and other cellular proteins, maintains the morphology of epithelial cells. An intracellular ring of actin and myosin at the apical/lateral interface (the perijunctional actomyosin ring) provides a scaffold for the tight junctions between epithelial or endothelial cells. The primary transmembrane structural components of tight junctions are the claudin family proteins, junctional adhesion molecule (JAM) and occluden. These proteins interact directly with the ZO family proteins, which link them to the perijunctional ring of the cytoskeleton. These proteins also interact with several regulatory/signaling molecules. The ZO proteins contain a guanylate kinase (GUK) domain as well as a src homology 3 (SH3) domain and a PDZ domain. The atypical PKC isotype specific interacting protein (ASIP) and the ras binding protein AF-6 also contain PDZ domains, and have been shown to associate with junctional complexes. PKC phosphorylates occluden, which results in its translocation to the tight junction. In subconfluent epithelial cell cultures, ZO-1 localizes to the nucleus but is located at the junctions in confluent cultures of epithelial cells. Myosin light chain kinase phosphorylation of the myosin II (regulatory subunit) is associated with contraction of the perijunctional ring and increases in paracellular permeability. Protein kinase A (PKA) activation increases conductance, but not permeability to large molecules across tight junction, while activation of PKC increases paracellular permeability. Barrier function of the tight junction is also affected by calcium levels, which may be under the control of PKC. Rho GTPase family members control organization of the actin cytoskeleton, (specifically cdc42). Rab GTPase proteins, which play a regulatory role in vesicular trafficking, such as rab13 and rab3b, appear to play a role in junctional regulation that remains undefined. These observations demonstrate that numerous cellular components might be targeted to modulate the paracellular conductance.

Endothelial tight junctions share many components with epithelial tight junctions although distinct extracellular modulators impinge on their function. Inflammatory agents can increase endothelial permeability; these mechanisms include bradykinin, which increases blood-brain barrier permeability by acting on $B_2$ receptors, serotonin, which shows evidence for activation of 5-$HT_2$ receptors and a calcium-dependent permeability increase, and histamine, which is mediated by $H_2$ receptors and elevation of $[Ca^{2+}]_i$ and an $H_1$ receptor-mediated reduction in permeability coupled to an elevation of cAMP. Mechanisms induced by ionmycin have been shown to increase albumin clearance and decrease electrical resistance across bovine pulmonary microvascular and macrovascular endothelial cell monolayers. The ionmycin seems to produce barrier dysfunction by mechanisms that are independent of myosin light chain kinase activation and reductions in endothelial cell tethering forces via inhibition of protein kinase A and tyrosine kinase activities. In addition to these studies, many reports show that low molecular weight compounds may penetrate endothelial monolayers. Findings reveal that opening of the blood brain barrier by arachidonic acid, mediated by granulocytes and/or their products, can be attributed to the acid opening the blood-brain barrier for small molecular weight compounds at concentrations of 30-300 μM and 3 mM for larger molecular weight compounds. In other words, arachidonic acid, generated in response to granulocytes and their products, modulates the endothelial barrier to allow permeation by small solutes at low concentration (<300 μM) and larger solutes at higher concentrations. Recent studies show that intra-arterial administration of alkylglycerol represents a well controllable method for enhanced drug delivery to the brain and to brain tumors through the blood brain barrier; in the presence of alkylglycerols at concentrations of 10-30 mM, a reversible and concentration-dependent enrichment of administered drugs was observed. Another experiment revealed that leucine enkephalin enhanced bovine brain microvessel endothelial cell monolayer permeability either by altering paracellular openings or through formation of a small pore in the monolayers to allow preferential penetration of low molecular weight or small molecular size substances. These observations highlight that ongoing regulation of endothelial tight junctions occurs in vivo. The results further suggest that there is not a well-targeted pharmaceutical on the market that can be used to modulate the endothelial barrier.

Numerous techniques are currently being evaluated for the ability to selectively and transiently modulate epithelial and endothelial barrier function. In addition to the methods listed above, pharmaceuticals are being linked to actively transported peptides, as a means to cross the blood-brain barrier. While this allows very selective targeting, the method requires a unique synthetic process for every transported compound. Alternatively, methods are being developed to reduce epithelial tight junctions enough to allow large molecules to diffuse to the interstitial space. Both calcium chelators and surfactants have been employed, but have unacceptable side effects including global changes in cell function and diminished cell adhesion. Alternatively, the zonula occludens toxin of *Vibrio cholerae* (ZOT) provides a naturally occurring alternative for increasing the permeability of small intestine epithelia. ZOT and its eukaryotic homologue, zonulin, interact with an epithelial membrane receptor that leads to a reduction in epithelial electrical resistance, presumably by activation of PKCα. The effects of ZOT are rapid in onset (<20 minutes) and readily reversible on washout. Thus ZOT is an excellent candidate as an adjunct to standard therapy to increase oral bioavailablility of large molecules across intestinal epithelium. In fact, ZOT has been used to increase the permeation of anticonvulsant drugs across epithelial monolayers, to increases the uptake of PEG 4000 from rabbit small intestine and into the bloodstream. In diabetic rats, the bio-availability of oral insulin was sufficient to control blood glucose to the same degree as parenteral administration. However, ZOT has some drawbacks as a more generalized therapeutic in that it is a large peptide (399 a.a.) and has a relatively small therapeutic target. Effects are observed only in the small intestine where distinct receptors are present. It was subsequently reported that an 8 a.a. peptide could fully inhibit the effects of ZOT on small intestine. Thus, the small peptides that we are developing may have some therapeutic advantages in that a wider tissue applicability may be observed (effect on renal, reproductive, intestinal, and airway epithelia have been observed) and it is a small peptide making it much more economical to commercially produce.

Channel forming peptides have not previously been used to modulate or regulate tight junctions.

U.S. Pat. No. 5,543,399 describes the purification and lipid reconstitution of CFTR protein and CF therapy making use of that protein. There is no teaching or suggestion in this reference of the use of relatively small, easily prepared pure peptides, and particularly peptides which are fragments of channel-forming proteins.

U.S. Pat. No. 5,368,712 teaches the use of small peptides reconstituted in artificial membranes as diagnostic tools. This patent does not describe any therapeutic applications using such peptides.

U.S. Pat. No. 6,077,826, the content of which is hereby incorporated by reference, describes the use of multiple-peptide channel assemblies which transport anions through epithelial cells, synthetic peptides capable of forming such assemblies, channel assemblies which alter the flux of water across these cells, and channel assemblies which alter the transepithelial electrical resistance of cells. These assemblies were based on the M2GlyR sequence and were modified to increase their solubility. However, the activity of these assemblies is limited to about 15 μA/cm² at a concentration of about 500 μM. Additionally, the peptides of this invention form multimers in solution, which have decreased affinity for membranes and suffer from solution aggregation.

Accordingly, what is needed in the art are channel assemblies which exhibit a more potent effect on the transepithelial electrical resistance of cells and transport anions through cells with a greater efficiency. Such peptides should also exhibit greater stability and a lower occurrence of multimers when added to solution. What is further needed are peptides which modulate or regulate tight junctions.

SUMMARY OF THE INVENTION

The present invention solves the problems inherent in the prior art and provides a distinct advance in the state of the art. Peptides of the present invention exhibit an improvement in activity that is about 5 fold greater with respect to activity levels and/or a 10 fold increase in effective concentration than was heretofore possible. The present invention is directed to improved 1) multiple peptide channel assemblies for transport of anions (e.g., Cl⁻) through epithelial cells, 2) synthetic peptides capable of forming such channel assemblies, 3) methods of using the channel assemblies in therapeutic contexts for altering the flux of water across epithelial cell layers, and 4) multiple peptide channel assemblies which alter the transepithelial electrical resistance of cell layers. The peptides of present invention exhibit greater stability and reduced solution aggregation, which lead to increased bio-availability of the peptides, thereby reducing the amount of peptide necessary to affect a desired response.

In preferred forms, the channel assemblies of the invention comprise multiple peptides each having from about 16-31 amino acid residues, and more preferably from about 22-27 residues. The peptides are characterized by the ability of providing, in an embedded channel assembly, transport of anions through an epithelial cell membrane and modulation (alteration) of the water flux across the epithelium. The peptides are also characterized by their effect on reducing the transepithelial electrical resistance of cell monolayers. Preferred peptides of the present invention will have activity profiles of greater than about 15.0 μA/cm² in MDCK cells when applied to the MDCK cells at a concentration of about 500 μM. More preferably, peptides of the present invention will have activity profiles of greater than about 15.0 μA/cm² in MDCK cells when applied to the MDCK cells at a concentration of about 300 μM, and still more preferably at a concentration of about 200 μM, and most preferably at a concentration of less than about 100 μM. Moreover, some preferred peptides are soluble in water to a level of at least about 5 mM, and more preferably at least about 10 mM, and still more preferably at least about 15 mM. The peptides of the invention also should exhibit at least about 50% helical content (advantageously at least about 65% helical content, and still more preferably at least about 75%) when dispersed in a 20% trifluoroethanol/80% water solution and measured using circular dichroism spectroscopy (CD). Preferred peptides of the present invention are also characterized by greater stability and fewer multimeric forms in solutions. Preferably, the peptides will predominantly form only monomers when dissolved. Monomers are preferred due to their higher binding affinity to the membrane. This increased affinity is due to the non-aggregation of the hydrophobic portions, which are required for membrane binding, and are therefore available for binding. This increases the overall bio-availability of sequences comprising mainly monomers. When sequences include multimeric forms, the hydrophobic portions aggregate, thereby rendering them unavailable for binding and decreasing their bio-availability. For peptide sequences that affect epithelial barrier function, such sequences will induce a reduction in electrical resistivity of cell monolayers, that is transient in nature and allows for the passage of larger molecular weight polymers (up to 40,000 Daltons) that are hydrophilic in character. This effect is thought to reversibly modulate the tight junctions that join adjacent epithelial cells into a confluent layer.

In the case of CF therapies, the channel assemblies are embedded in the cytoplasmic membrane of affected epithelial cells. These peptides spontaneously insert into the cytoplasmic membrane on contact, and spontaneously aggregate within the membrane to form a channel assembly having a hydrophilic internal pore through which Cl⁻ may pass, and a lipophilic external surface allowing solubility of the assembly in the membrane. Preferably, the peptides making up the channel assemblies are identical.

The peptides ideally have an amino acid sequence based upon the sequence of the M2GlyR peptide, which has been subsequently modified by the addition of multiple polar amino acid residues on either the C- or -N termini. The peptide C-$K_4$-M2GlyR (PARVGLGITTVLTMTTQSSG-SRAKKKK) (SEQ ID No. 2), was initially chosen as the lead CF drug compound due to its higher solubility in water, higher proportion of monomer in solution, and its ability to better mimic the pharmacology associated with the unmodified M2GlyR sequence. The second peptide N-$K_4$-M2GlyR (SEQ ID No. 3) (KKKKPARVGLGITTVLTMTTQSSG-SRA), upon closer analysis, shows an approximately 50% higher level of conductance than the C-$K_4$ peptide. It also appeared to form channels faster and had channels with improved stability. This increase in activity may be due to a structural difference that was been observed in modeling studies. In addition to these differences, other disparate properties such as degrees of aggregation in solution, rates of aggregation in physiological buffers and sensitivities to different channel blocking agents have been noted between the two peptides. Anion permeation throughout these artificial channels is modified by the activity of potassium channels in the basolateral membrane that are thought to set the electrical driving force across the cell membrane. The anion conductance seen with C-$K_4$-M2GlyR is most likely the result of a novel chloride conductance pathway. These measurements were obtained using Madin-Darby canine kidney cells, the human colonic epithelial cell line (T84), and airway epithelial cells derived from a human cystic fibrosis patient (IB3-1). N-$K_4$-M2GlyR also acts to form a novel chloride-conductive pathway but yields an approximately 50% increase in short circuit current ($I_{SC}$) over that of C-$K_4$-M2GlyR as described above. This increase in activity may be due to a structural difference that has been observed in modeling studies. In recent studies, both peptides were shown to restore glutathione transport in cultured CF monolayers. Again, C-$K_4$-M2GlyR was active but to a much lesser extent, thereby reaffirming the theory that N-$K_4$-M2GlyR functions better than C-$K_4$-M2GlyR. Animal testing using N-$K_4$ and C-$K_4$ peptides (nasal PD's in the transgenic CF mouse model) indicated that the peptides were able to induce anion conductances in diseased mice that were at least 60% of normal (unaffected) activity. The fact that N-$K_4$-M2GlyR can be regulated by the cell through baso-lateral $K^+$ channels and that its presence in compromised CF cell line helps restore glutathione transport, suggests that this peptide improves the health of CF cells.

However, one of the obstacles to generating better channel forming sequences based on the M2GlyR sequence has been the multi-state nature of N-$K_4$M2GlyR and C-$K_4$M2GlyR in solution. Research has shown that monomeric and dimeric forms of the C-$K_4$- and N-$K_4$-M2GlyR peptides have high channel forming activity while higher molecular weight species are inactive. Any increases in low molecular weight species will increase the bio-availability of the peptide and thus reduce the amount of peptide needed to effect the desired response. Studies have shown that the $NH_2$-terminal half of the modified segments of the invention contributes to intramembrane helical bundle formation while the COOH-terminal half of the segment is responsible for aggregation in aqueous solution. Therefore, in an attempt to reduce the amount of solution aggregation, a new family of peptides based on the M2GlyR sequence was created using a modular approach. The modules consist of the 11 amino acid residue segments that surround the central leucine (L) residue: module A=PARVGLGITTV (SEQ ID No. 48) and module B=TMTTQSSGSRA (SEQ ID No. 49). Using this nomenclature, the native sequence for M2GlyR is A•L•B. Derivative sequences were created using module A (PARVGLGITTV), module B (TMTTQSSGSRA), the A module in reverse (VTTIGLGVRAP) (SEQ ID No. 50), referred to as a, the B module in reverse (ARSGSSQTTMT) (SEQ ID No. 51) referred to as b, the A' module (AARVGLGITTV) (SEQ ID No. 52) having an alanine substituted for the initial praline of the A module, and the a' module (VTTIGLGVRAA) (SEQ ID No. 53) which is the A' module in reverse. New sequences were generated by combining the six modules, A, B, a, b, A', and a', in all possible combinations separated by the leucine normally found between these modules in the wild-type sequence. Sequences such as A•L•A, a•L•a, a•L•A, A'•L•b, etc. were synthesized. In other sequences employing the six modules, tryptophan (W) was used between the modules, as opposed to the naturally occurring leucine. Additionally, other sequence variants were produced in an effort to develop M2GlyR variants with greater stability and higher potency.

Preliminary results indicated those newly designed peptides with a propensity to form an alpha-helical structure (assessed by CD in 20% or 40% trifluoroethanol (TFE) in $H_2O$), were more likely to promote anion secretion across epithelial cell monolayers.

Based upon success in solubilizing transmembrane sequences, amino-terminal lysyl adducts were added to the C- and N-termini of the new modular mutants. C- and N-$K_4$- (A•L•a) (PARVGLGITTV-L-VTTIGLGVRAP) exhibited higher activity than had previously been found in the prior art. Because this sequence is a palindrome, the amino- and carboxyl-terminal lysyl adducts allow for testing the effects of the helical dipole on anion transport. Both adducts exhibit increased Isc in MDCK epithelial cell monolayers with half maximal effects observed at or below 30 µM, a nearly 10-fold improvement over any peptide previously characterized in the C- and N-$K_4$ M2GlyR family. C-$K_4$ A•L•a, however, produced channels with cytotoxic effects while N-$K_4$ A•L•a produced equally high maximal ion transport rates (up to 45 $\mu Amp/cm^2$) and were not harmful to isolated cells. In comparison, N-$K_4$_M2GlyR requires a 4-fold higher concentration than N-$K_4$-PARVGLGITTV-L-VTTIGLGVRAP (A•L•a) (SEQ ID No. 18) to support anion flux ($EC_{50}$ 208 µM vs. 50 µM). SDS-PAGE of cross-linked peptides revealed that the N-$K_4$ A•L•a is >90% monomeric with only a trace of dimer and no indication of higher order aggregates. FIG. 14 illustrates the concentration dependence of SEQ ID No. 19. In this figure, A' and a' have had their terminal proline residue replaced by an alanine.

Initially, the most active variant form of M2 was SEQ ID No. 18. Several modifications were made to this sequence and subsequently tested. Some of these variants have enhanced activity in comparison to SEQ ID No. 18. This enhanced activity is present despite the fact that tested variants of M2GlyR included palindromic sequences, mutated sequences, truncated sequences, and combinations of all of these. Some sequences included replacements for one or both proline residues as well as deletion or replacement of the central leucine residue(s). Removal of the prolines improves the ease of synthesis.

It was also discovered that certain of the sequences (SEQ ID Nos. 9, 18, 19, 26, 27, 54, and 55) had extremely high channel forming activity and the unexpected effect of a dramatic decrease in transepithelial electrical resistance that far exceeded the expected change associated with apical membrane channel insertion. Such an unexpected effect occurred upon the onset of channel activity in MDCK monolayers and this effect is illustrated in FIG. 15. Of these peptides, SEQ ID Nos. 54 and 55 required a much lower concentration of peptide to reach full activity. FIG. 16 illustrates the effect of SEQ ID No. 55 on $I_{SC}$ and $R_{TE}$. This sequence induced a 70% and 90% decrease in resistance at 100 and 200 µM, respectively, in MDCK monolayers. As shown by FIG. 17, other peptides exhibited similar effects. However, the effect on the time-dependent decrease in $R_{TE}$ exhibited by certain of these peptides (with FIG. 17 showing the results for SEQ ID No. 27) at slightly lower concentrations (60 and 80 µM, respectively) indicates a strong concentration dependence on residual resistance. This is because the total resistance loss was less at these lower concentrations.

To test whether the change in transepithelia electrical resistance was permanent, an experiment was designed to evaluate $R_{TE}$ after the peptide was removed from the solution bathing the apical surface. In this experiment, the MDCK monolayers were initially incubated with 60 µM of SEQ ID No. 27. When the residual resistance reached approximately 10% of the initial value, the peptide was removed by aspiration and followed by the addition of pre-warmed Ringers solution. $I_{sc}$ and $R_{TE}$ were then monitored for the next 6 hours with the results provided in FIG. 18. In this figure, the solid line represents $I_{sc}$ and the vertical bars result from a periodic 1 mV bipolar pulse. The current deflection magnitude associated with the bipolar pulse is inversely proportional to the resistance in accordance with Ohm's law. The larger the bar, the lower the resistance. Prior to peptide exposure, the vertical bars were small and reflected an $R_{TE}$ of 600 $\Omega cm^2$. As peptide was added to the apical surface, the measured current increased rapidly. As the current approached its highest value, the resistance began to drop. The observed change in $R_{TE}$ was far greater than would be predicted for simple channel insertion. The minimum resistance observed was 40 $\Omega cm^2$, measured shortly after the peptide was removed from the apical bathing solution. After about an hour, post peptide treatment, $R_{TE}$ began to slowly increase in value. After six hours, $R_{TE}$ was 135 $\Omega cm^2$. These results demonstrate that peptide-associated change in $R_{TE}$ is reversible. $R_{TE}$ returned to pretreatment values within 48 hours.

In another experiment, the reversibility of peptide-induced change in $R_{TE}$ was tested repeatedly with a number of polarized epithelial monolayers. The pooled results of this experiment are shown in FIG. 19. The exact same monolayers (n=12) were treated with peptide such that $R_{TE}$ was reduced and the subsequent return in resistance was monitored as a function of time. All monolayers were briefly exposed to peptide on day 1 with a consistent reduction in transepithelial electrical resistance being observed. The same monolayers were assessed and retreated at 48, 72, 96, and 120 hours. With the exception of a few monolayers that became fungally contaminated, all cells recovered. Forty-eight hours appears to be an adequate period for complete restoration of monolayer resistance. This experiment also demonstrated that the same monolayer can be subjected to repeated treatments without compromising the ability to regain and maintain epithelial barrier integrity that is indistiguishable from untreated epithelia. Results from another experiment demonstrated the ability of a high molecular weight reporter molecule to cross the monolayer to a greater extent after treatment with a peptide of the invention. In this experiment, monolayers were treated with 100 µM of peptide in the absence of the basolateral K+ channel activator 1-EBIO. Peptide was subsequently removed and the reporter molecule (9.5 kDa FITC-dextran) added to the apical compartment. Fluorescence was assessed in aliquots taken from the basolateral solution after 15 minutes. FIG. 20 illustrates the results for SEQ ID No. 27. Epithelial permeation by the reporter molecule was significantly enhanced by peptide exposure. An aliquot taken after 30 minutes indicated that the translocation of the reporter dye had decreased, again suggesting that the peptide-induced permeation pathway for large solutes across the epithelial monolayer is only transiently available. The most likely way the dye-labeled dextran molecule could pass from one side of the monolayer to the other would be if the paracellular pathway had been opened through disruption of the cell-cell tight junctions that impart the high resistance barrier. Accordingly, the present invention provides peptides operable for reversibly opening tight junctions. Preferred peptides in this respect include SEQ ID Nos. 9, 18, 19, 26, 27, 54, and 55. Additionally, the present invention provides methods of modulating the tight junctions such that molecules which cannot cross the junction without the treatment are able to cross the junctions after the treatment. It is preferred that the junctions can be opened to permit the crossing thereof by a molecule of any size. It is noted that opening tight junctions may not be a good feature for a cystic fibrosis therapeutic, however, it may be an outstanding way to facilitate delivery of DNA or drugs to other tissues in the body. Advantageously, the process is reversible through the removal of the causative peptide, including through dilution/washes or complexation with an antibody. Moreover, the peptides of the present invention work at relatively low concentrations (~30 µM) relative to other agents such as EDTA which work at concentrations that are at least 100-fold higher.

The present invention also includes a method of altering the flux of water from an epithelial cell presenting first and second spaced apart surfaces. The method broadly includes providing multiple peptides capable of forming a channel assembly with each of such peptides having from about 16-31 amino acid residues therein. These peptides are contacted with the first surface of an epithelial cell thereby causing the peptides to embed therein and alter the flux of water across the cell. In accordance with the method aspects of the invention, the epithelial cells may be selected from the group consisting of CF-affected epithelial cells, e.g., cells selected from the group consisting of airway, intestinal, pancreatic duct and reproductive tract epithelial cells. In the case of airway epithelial cells, the method further comprises a delivery step immediately preceding the contacting step, wherein the channel-forming peptides are aerosolized inhaled. In another representative method, the epithelial cells are cystic epithelium of an APKD-affected individual, and the first surface of the epithelial cells is the basolateral membrane of such cells.

In another method of the present invention, the electrical resistivity or barrier to solute flux of cell layers can be decreased by contacting the cell layer with a peptide. Preferably, the peptide is a derivative of SEQ ID No. 1 and includes a portion that is palindromic to a portion of SEQ ID No. 1 or to itself. Preferably, this palindromic portion comprises at least about 7 amino acid residues, more preferably at least about 9 amino acid residues and still more preferably, at least about 11 amino acid residues. In order to increase the solubility of these peptides, the C- and/or N-termini thereof can be modified to contain a plurality of polar amino acids thereon. A particularly preferred polar amino acid is lysine. The concentration of the peptide necessary for decreasing the cell layer electrical resistivity or increasing solute permeation is preferably up to about 500 µM, more preferably up to about 300 µM, still more preferably up to about 200 µM, and most preferably, less than about 100 µM. Particularly preferred peptides will have at least about 35% sequence homology with a sequence selected from the group consisting of SEQ ID Nos. 4-47, 54, and 55. More preferably, these peptides will have at least about 50% sequence homology, still more preferably at least about 65%, even more preferably at least about 75%, still more preferably at least about 85%, even more preferably at least about 90%, even more preferably at least about 95% and most preferably at least about 98% sequence homology with a peptide selected from the group consisting of SEQ ID Nos. 4-47, 54, and 55. SEQ ID No. 27 is also particularly preferred for this aspect of the invention.

The channel-forming peptides of the invention are normally in the L-stereoconfiguration. However, the invention is not so limited and indeed D-stereoconfiguration peptides can also be used. The latter type of peptides may also have significant advantages as they are not degraded in vivo by proteolytic enzymes nor do they elicit an immune response.

During the course of this study, it was noted that N-$K_4$-(AARVGLGITTV-L-VTTIGLGVRAA) (A'•L•a') (SEQ ID No. 27) exhibits all the targeted attributes for a CF therapeutic (monomeric, soluble, high transport rates). However, SEQ ID No. 27 was also found to cause an increase in the transepithelial electrical conductance ($g_{TE}$) across MDCK monolayers which may indicate an effect on the paracellular pathway and specifically on tight junctions. Such an effect may preclude this sequence from use as a CF therapeutic but may thereby represent a possible tool for the study or manipulation, modulation, or regulation of the epithelial barrier. Additionally, peptides having at least one form of the A module (A, a, A', and a') therein, and especially those with at least two forms of the A module (each individually and respectively selected) exhibited greater ability to induce de novo ion transport and increase conductance across cell monolayers. The Ala, ALa', and A'La' sequences all achieved similar $I_{max}$ at 100 μM and caused the monolayers to gain conductance. Of these, the L and D-stereoisomers of SEQ ID No. 27 were able to trigger conductance increases in MDCK monolayers at concentrations of 40 μM, a value equal to the concentration required for 0.5 $I_{max}$. The other sequences showed this effect at concentrations ≥100 μM, a value equal to or above that required to reach $I_{max}$ in MDCK monolayers.

As previously discussed, tight junctions are complex, highly regulated dynamic structures that are a barrier to movement of solutes between apical and basolateral compartments and form a fence that maintains cell membrane polarity. Regulated openings of junctions occur in a variety of situations such as sperm maturation, extravisation of lymphocytes and nutrient uptake in the intestine. Pathology associated with aberrant function and dysregulation of tight junctions includes cancer metastases, autoimmune dysfunction and inflammatory bowel disease. Tight junctions are targets of bacterial toxins such as *Vibrio cholerae* zonlua occludens toxin (ZOT) and *Clostridium difficile* toxins TcdA and TcdB in pathological, experimental, and perhaps therapeutic situations. A mammalian homolog of ZOT has been identified and may be a primary physiological regulator of tight junctions in intestinal tissues. Additionally, cytokines and a number of second-messengers are known to be involved in the modulation of tight junctions, although the mechanisms by which these processes occur remain to be elucidated.

A variety of treatments including $Ca^{2+}$ chelation, surfactants, fatty acids and cationic polymers have been used to experimentally modulate the paracellular pathway. However, when applied in vivo, side effects of the chemical treatments used to modulate $g_{TE}$ can include hypersensitivity, asthma, anaphylaxis and the sloughing of epithelial cells. Surfactants and detergents can cause cell lysis and sloughing while $Ca^{2+}$ chelators can cause cytoskeletal rearrangements and interfere with calcium signaling pathways. An additional drawback to these treatments is that, in general, there is little separation between the effective concentration and the cytotoxic concentration. Alternatively, ZOT, which lacks many undesirable side effects has been used to modulate the epithelial barrier in an experimental therapeutic setting. The results are encouraging and provide a 'proof of concept' indicating that intestinal tight junctions can be modulated to allow for the absorption of high molecular weight therapeutic compounds without apparent deleterious side effects. Other studies have suggested that gene therapy might be augmented by transiently reducing epithelial tight junction integrity, as well. Thus, there is a great need to identify safe and efficient means by which to modulate the epithelial barrier function at the tight junction in a wider variety of epithelia.

In another aspect of the present invention, the relationship between apical exposure of epithelial cells to SEQ ID No. 27 and resultant changes in barrier function as typified by the increase in $g_{TE}$ and transepithelial solute permeability, is defined. Results show that SEQ ID No. 27 provides a route for ion permeation across the cell membrane and modulates the paracellular pathway over a similar concentration range although the time-course of the two responses is different.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence homology", as used herein, also refers to a method of determining the relatedness of two sequences. To determine sequence homology, two or more sequences are optimally aligned as described above, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

As used herein, "derivative" with respect to M2GlyR, refers to mutants produced by amino acid addition, deletion, replacement, and/or modification; mutants produced by recombinant and/or DNA shuffling; and salts, solvates, and other chemically modified forms of the sequence which retain the activity of the related sequence. Derivatives also include palindromes and reversals of the M2GlyR sequence, palindromes and reversals of portions of the M2GlyR sequence (such as some of the modules generated) and combinations of any of the above.

Sequences having or including a portion having at least about 35% sequence homology with any one of SEQ ID Nos. 4-47, 54, and 55 are embraced within the present invention. More preferably, these peptides will have at least about 50% sequence homology, still more preferably at least about 65%, even more preferably at least about 75%, still more preferably at least about 85%, even more preferably at least about 90%, even more preferably at least about 95% and most preferably at least about 98% sequence homology with a peptide selected from the group consisting of SEQ ID Nos. 4-47, 54, and 55.

Additionally, derivatives of the M2GlyR sequence which have their solubilities modified to a level of at least 5 mM and which exhibit similar properties to any one of SEQ ID Nos. 4, 9, 10, 13, 14, 18, 19, 21, 26-28, 32-35, that is sequences which exhibit greater than 15.0 $\mu A/cm^2$ at a peptide concentration of 500 μM are embraced within the present invention. Preferably, these derivatives will have their solubilities modified by the addition of multiple polar amino acid residues on the C- or N-ends thereof. Moreover, it is preferred that these derivatives exhibit an activity profile of at least about 15.0 $\mu A/cm^2$ in MDCK cells at a level of 500 μM. More preferably, these derivatives will have an activity profile of at least about 15.0 $\mu A/cm^2$ in MDCK cells at a level of 300 μM, and still more preferably an activity profile of at least about 15.0 $\mu A/cm^2$ in MDCK cells at a level of 200 μM. Most preferably, such derivatives will have an activity profile of at least about 15.0 $\mu A/cm^2$ in MDCK cells at a level of 100 μM. Notably and advantageously, many of the generated sequences exhibited higher activity at lower concentrations than the previously known sequences (SEQ ID Nos. 1-3), thereby allowing a lower concentration of peptide to be used yet resulting in higher activity. It was also observed that, after certain peptide concentration levels had been reached, little or no increase in activity resulted. This tapering off of activity at higher concentrations should permit sequences having high activity at low concentrations to be used with a minimum amount of side effects due to excess peptide being used. Advantageously, this should also result in lower cost per dose, when used in treatment or therapy.

BRIEF DESCRIPTION OF THE DRAWINGS

FIG. 1 is a graph illustrating the effect on $I_{SC}$ of a peptide on an MDCK cell monolayer wherein maximal effect occurs at a peptide concentration of at least 500 μM;

FIG. 2 is a graph illustrating the effect on $I_{SC}$ of a peptide on an MDCK cell monolayer wherein maximal effect occurs at a peptide concentration of at least 200 μM, and wherein the cell layer resistivity was greatly affected;

FIG. 3 is a graph illustrating the effect on $I_{SC}$ of a peptide on an MDCK cell monolayer wherein maximal effect occurs at a peptide concentration of at least 100 μM;

FIG. 4 is a graph illustrating the effect on $I_{SC}$ of a peptide on an MDCK cell monolayer wherein maximal effect occurs at a peptide concentration of at least 100 μM, and wherein the cell layer resistivity was greatly affected;

FIG. 5 is a graph illustrating the effect on $I_{SC}$ of a peptide on an MDCK cell monolayer wherein maximal effect occurs at a peptide concentration of at least 500 µM;

DETAILED DESCRIPTION OF THE PREFERRED EMBODIMENT

Figure 1:
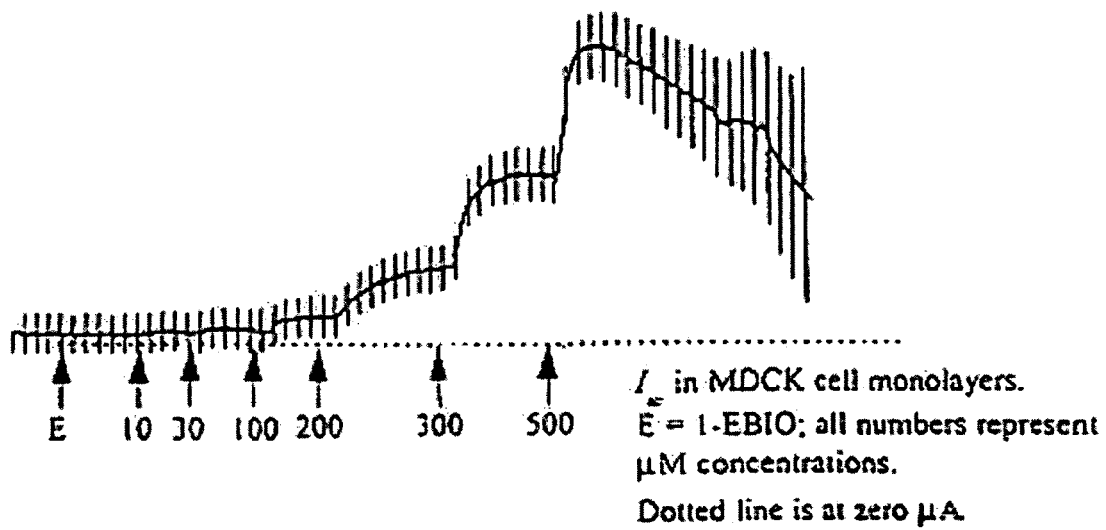

The following examples set forth preferred embodiments of the present invention. It is to be understood, however, that these examples are provided by way of illustration and nothing therein should be taken as a limitation upon the overall scope of the invention.

All summary results are presented as the arithmetic mean±SEM. The differences between control and treatment data were analyzed using ANOVA, Tukey (SAS Institute, Inc., Cary, N.C.), and Student's t-test (Excel, Microsoft Corporation, Redman, Wash.). The probability of making a type I error less than 0.05 was considered statistically significant.

Example 1

This example generated the peptides and cell monolayers for subsequent testing. Additionally, epithelial electrical measurements were taken and activity profiles determined for a number of these generated peptides.

Materials and Methods

Peptide synthesis. The synthetic peptides based on the M2GlyR sequence were prepared using an automated solid-phase peptide synthetic technique. The peptides were prepared using the well documented, base-labile, Fmoc-strategy on an Applied Biosystems Model 431A peptide synthesizer (Perkin Elmer, Norwalk Conn.). All solvents were reagent grade unless otherwise indicated and the protected amino acids were purchased from one or more of the following vendors (Perkin Elmer, Norwalk Conn.; Bachem, Torrance Calif.; Peninsula Laboratories, Belmont Calif. and Peptides International, Louisville Ky.). A reaction scale of 0.1 mmol was employed. The resin, p-hydroxymethylphenoxymethyl polystyrene (HMP resin) was purchased with the first amino acid already attached and the degree of substitution calculated (0.51 mmol/g) (Perkin Elmer, Norwalk Conn.). The N-terminus of the resin bound amino acid was reversibly blocked with the N$^\epsilon$α-fluorenylmethoxycarbonyl (Fmoc) protecting group and was weighed out and loaded into the reaction vessel (RV) of the synthesizer. The resin was first washed and swelled washed in the RV using 2×1.5 mL of N-Methylpyrrolidinone (NMP). The Fmoc group was subsequently removed by two sequential treatments with 4.5 mL of 22% piperidine (v/v) in NMP. The first deprotection was completed in 1 minute and the second after an additional 11 minutes. The resin was subsequently washed with 4×2.0 mL of NMP. The RV was drained and the resin was then ready to be coupled to the first incoming amino acid.

During the deprotection and washing steps outlined above, the incoming Fmoc-protected amino acid was preactivated to make it more reactive toward the resin-bound residue. The preactivation incubated 1-Hydroxybenzotriazole (HOBt) in the presence of the condensing agent 2-(1H-benzotriazol-1-yl)-1,1,3,3-tetramethyluronium hexafluorophosphate (HBTU), thereby resulting in the formation of a highly reactive HOBt-amino acid ester. A ten-fold excess of amino acid (1.0 mmol) over resin sites was weighed out and transferred to a labeled plastic cartridge. Just prior to preactivation the amino acid was dissolved in 2.1 mL of NMP in the cartridge. This activation reaction begins upon the addition of 2.0-2.1 mL (0.9-0.95 mmol) of the 1:1; HOBt:HBTU in dimethylformamide (DMF) reagent. The amino acid was present in slight excess over the HOBt:HBTU in order to limit the possibility of undesirable side reactions. After the reaction had proceeded for 10 minutes at room temperature, 1.0 mL of 2M N,N-diisopropylethylamine (DIEA) was delivered to the amino acid cartridge, mixed briefly by bubbling argon and then the entire 5 mL solution was transferred to the RV. This transfer initiates the coupling of the incoming amino acid to the resin bound amino acid.

The coupling reaction proceeded for 25 minutes and was terminated by filtering off the soluble reactants. The resin was washed as described above and a second aliquot of preactivated HOBT ester-amino acid (prepared as described above) was added and allowed to react for 25 minutes. This second addition of the same amino acid was used to maximize the coupling efficiency of the amino acid to the resin. The first reaction usually results in about 95% efficiency and the second reaction increases it to about 99.5%. The remaining 0.5% sites were eliminated by a 5 minute reaction with 5 mL of a solution containing the following reactants in NMP at the given concentrations: 0.5 M acetic anhydride, 0.125 M DIEA, and 0.015 M HOBt. The RV was again drained and resin was subsequently washed with NMP as described above. The coupling of one amino acid to the resin was then complete. By maintaining high coupling efficiencies for the amino acids and then capping any low reactivity sites during the synthesis the number and diversity of failed or undesirable side products were significantly reduced, thus making the product easier to purify to homogeneity.

In order to add the next amino acid, the protocol outlined above was repeated with the appropriate N-Fmoc-protected amino acid. By the successive step-wise repetition of the deprotection, amino acid activation, and coupling steps, the entire sequence was assembled. The fully assembled resin bound peptide was finally washed with dichloromethane (DCM) and dried overnight under reduced pressure. The dried product was weighed and the overall synthetic yield was calculated based on a calculated theoretical 100% efficiency. For a 0.1 mmol scale synthesis, starting with 196 mg using a resin substitution of 0.510 mmol/g, the theoretical yield was 518 mg. Our average dried weight from 10 separate syntheses was 505 mg giving a calculated yield of 97.5% overall with a per step coupling efficiency of 99.88%.

The peptide was released from the resin and all side chain protecting groups were removed using a chemical cleavage reaction. In this reaction 500 mg of peptide/resin was incubated with 9.0 mL of trifluoroacetic acid (TFA) in the presence of 0.5 mL of 1,2-ethanedithiol and 0.5 mL of thioanisole at room temperature for 200 minutes. The mixture containing the cleaved peptide and by-products was removed from the solid resin support by filtration. The peptide was then precipitated by the addition of cold (4° C.) t-butyl methyl ether. The peptide precipitate was harvested by centrifugation and the ether containing the bulk of the cleavage by-products was decanted off. The precipitate was washed with the cold ether and recentrifuged a total of three times. The washed peptide was then dissolved in 20% acetic acid in water and extracted 3 more times with ether. After each extraction the ether layer was removed after a brief centrifugation. At this point the aqueous layer may be clear or slightly turbid. After these liquid-liquid extractions the water layer was shell frozen in a dry ice/ethanol bath and then dried by lyophilization. While the synthesis was complete at this point the peptide was not ready for administration to the cells.

The peptide produced above was purified to homogeneity by reversed-phase high performance liquid chromatography (RP-HPLC). The dried crude peptide (5 mg portions repeated 100 times) was dissolved in 1.0 mL of TFE (Aldrich Chemical Co., Milwaukee Wis.). A 0.2 mL sample was injected onto a pre-equilibrated polystyrene based-$C_4$ semi-prep RP-HPLC column (PLRP-S 300 Å, 7.5×50 mm Polymer Laboratories, Amherst Mass.). The column was equilibrated 18% acetonitrile ($CH_3CN$) in deionized-distilled water containing 0.1% TFA at a flow rate of 2.0 mL/minute using a System Gold 125/166 computer controlled HPLC instrument (Beckman Instruments, Fullerton Calif.). After maintaining the 18% for three minutes post sample injection, a programmed gradient from 18% $CH_3CN$ to 54% $CH_3CN$ over 10 minutes was then executed. The column was maintained at 54% $CH_3CN$ for 7 minutes and then jumped to 80% $CH_3CN$ followed by a 6 minute hold prior to returning to the initial conditions. The desired product eluted at 40.5% $CH_3CN$ and was observed by measuring the change in optical absorbance at 215 nm. Multiple runs using the HPLC were required to purify all the peptide samples. The fractions containing the peptide from successive runs were pooled and lyophilized to dryness.

Sequence Confirmation: To confirm the correctness of the assembled sequence, an aliquot of the purified material is analyzed by both automated Edman sequencing and mass spectral analyses. For sequencing, 25 picomoles are applied to a glass filter that has been pretreated with Biobrene® (Perkin Elmer, Norwalk Conn.) and allowed to dry. The filter is then sequenced using as Applied Biosystems Model 473A pulsed-liquid protein sequencer. All reagents used on this instrument are obtained from the instrument manufacturer. The sequence obtained by this method indicates that the correct amino acids have been added in the correct positions of the peptide. Mass spectral analysis is carried out using a Lasermat 2000 matrix assisted laser desorption ionization, time of flight spectrometer (MALDI-TOF) (Finnigan Corp., San Jose Calif.). The peptide (1 pmol in 1 μL of 40% $CH_3CN$) in water is mixed with 1 μL of a 10 mg/mL solution of α-Cyano-4-hydroxycinnamic acid (Aldrich, Milwaukee Wis.) dissolved in 60% acetonitrile ($CH_3CN$) in deionized-distilled water containing 0.1% TFA along with 1 μL of a 20 μM solution of the standard peptide, substance P (Bachem Inc., Torrance Calif.), with a known mass of 1348.6 Da for the MH+1 ion. After the sample is mixed 1 μL is transferred to the etched center of a stainless steel sample slide and allowed to dry. Once dry, the sample is placed in the instrument and the mass determined at the lowest power that yields signal using the added standard to calibrate the instrument. A single observed mass was obtained for each of the purified M2GlyR peptides and these values were in agreement with the predicted values calculated from the sum of the individual amino acid masses. Together these two analyses indicate that the correct sequences were assembled, there were no detectable modifications to the sequence and that no detectable contaminants were present in the purified peptide sample.

Cell culture: MDCK cells were a generous gift of Dr. Lawrence Sullivan (Kansas University Medical Center, Kansas City, Kans.). T84 cells were obtained from Dr. Daniel Devor (University of Pittsburgh, Pittsburgh, Pa.). MDCK and T84 cells were maintained with similar culture procedures. The culture medium was a 1:1 mixture of DMEM and Ham's F-12 (Gibco BRL, Grand Island, N.Y.) supplemented with 5% heat inactivated fetal bovine serum (BioWhittaker, Walkersville, Md.), and 1% penicillin and streptomycin (Gibco BRL). Cells were grown in plastic culture flasks in a humidified environment with 5% $CO_2$ at 37° C. and passaged every 5-7 days. For Ussing chamber experiments, cells were plated on 1.13 $cm^2$ permeable supports (Snapwell™, Costar®, Cambridge, Mass.) at a density of approximately $1\times10^6$ cells/well and incubated in DMEM/F-12 supplemented with FBS and antibiotics (changed every other day) for 2-3 weeks prior to being mounted in modified Ussing flux chambers.

To form monolayers, the cells were plated onto the upper surface of a permeable membrane that forms the bottom of a plastic well. Two types were used. One was the Transwell™ insert (Costar®, Cambridge, Mass.) supported in a six-well tissue culture plate and the other type was the Snapwell™ (Costar®, Cambridge, Mass.). During incubation, the medium was replaced at 48-72 hour intervals. Confluent monolayers formed within 72 hours. Experiments were performed on the monolayers 6-9 days after the initial plating. Net fluid secretion responses were optimal after six days.

Solutions: Ringer solution was made fresh daily. The final concentration (in mM) was 120 NaCl, 25 $NaHCO_3$ 3.3 $KH_2PO_4$, 0.8 $K_2HPO_4$, 1.2 $MgCl_2$, 1.2 $CaCl_2$, (290±2 mOsmol). All components of the Ringer solution were from Sigma (St. Louis, Mo.).

Electrophysiology Chemicals: Stock solutions of chemicals were prepared as follows: forskolin (*Coleus forskohlii*, Calbiochem, La Jolla, Calif.), 10 mM in ethanol; 1-EBIO (Acros Organics), 1 M in dimethyl sulfoxide (DMSO); bumetanide (Sigma) 20 mM in ethanol; diphenylamine-2-dicarboxylic acid (DPC; Sigma), 1 M in DMSO; and 4,4'-Dinitrostilben-2,2'-disulfonic acid (DNDS; Acros Organics) 10 mM in Ringer solution. The following stock solutions were prepared at 100 mM in DSMO; glibenclamide, indanyloxyacetic acid (R(+)-IAA-94), 2-[3-(trifluoromethyl)-anilino]nicotinic acid (niflumic acid; Sigma), 5-nitro-2-(3-phenylpropylamino) benzoic acid (NPPB; RBI, Natick, Mass.). All other chemicals were purchased from Sigma and were of reagent grade unless otherwise noted.

Epithelial electrical measurements: Transepithelial ion transport was evaluated in a modified Ussing chamber (Model DCV9, Navicyte, San Diego, Calif.). The Ussing chamber's fluid resistance compensation was completed in Ringer solution (see below). For electrical measurements cell monolayers were bathed in Ringer solution maintained at 37° C. and continuously bubbled with 5% $CO_2$:95% $O_2$. The transepithelial membrane potential ($V_{te}$) was clamped to zero and the transepithelial short circuit current ($I_{sc}$), an indicator of net ion transport, was measured continuously with a voltage clamp apparatus (Model 558C, University of Iowa, Department of Bioengineering, Iowa City, Iowa). Data were digitally acquired at 1 Hz with a Macintosh computer (Apple Computer, Cuppertino, Calif.) using Aqknowledge software (ver. 3.2.6, BIOPAC Systems, Santa Barbara, Calif.) with an MP100A-CE interface.

Results

Table 1 provides the results of this example. The peptide sequences generated are identified as SEQ ID Nos. 1-55. Measured activity for these sequences is provided as $\mu A/cm^2$ at specific peptide concentrations.

TABLE 1

Activity profile in MDCK cells for Palindromic M2GlyR sequence module and variants

| Seq. ID # | Amino Acid Sequence | Name | Acitvity $\mu A/cm2$ |
|---|---|---|---|
| 1 | PARVGLGITT VLTMTTQSSG SRA | M2GlyR | 1.5 at 500 µM |
| 2 | PARVGLGITT VLTMTTQSSG SRAKKKK | $CK_4$M2GlyR or $CK_4$ALB | 12.5 at 500 µM |
| 3 | KKKKPARVGL GITTVLTMTT QSSGSRA | $NK_4$M2GlyR or $NK_4$ALB | 15.9 at 500 µM |
| 4 | KKKKARSGSS QTTMTLVTTI GLGVRAA | $NK_4$bLa' | 18.7 at 300 µM |
| 5 | KKKKVTTIGL GVRAPLVTTI GLGVRAA | $NK_4$aLa' | <1.0 at 500 µM |
| 6 | KKKKTMTTQS SGSRALTMTT QSSGSRA | $NK_4$BLB | <1.0 at 500 µM |
| 7 | KKKKTMTTQS SGSRALVTTI GLGVRAA | $NK_4$Bla | <1.0 at 500 µM |
| 8 | KKKKVTTIGL GVRAPLARSG SSQTTMT | $NK_4$aLb | <1.0 at 500 µM |
| 9 | KKKKAARVGL GITTVWVTTI GLGVRAA | $NK_4$A'Wa' | 20.0 at 100 µM |
| 10 | KKKKPARVGL GITTVWTMTT QSSGSRA | $NK_4$AWB | 20.0 at 500 µM |
| 11 | KKKKPARVGL GITTVTTMTT QSSGSRA | $NK_4$ATB | NT |
| 12 | KKKKPARVGL GITTVLTMTT QSSGSRAW | $NK_4$ALBW | NT |
| 13 | KKKKPARVGL GITTVLTMTT RS | $NK_4$ p22Q→R | 24.0 at 500 µM |
| 14 | KKKKPARVGL GITTVLTMTT QR | $NK_4$ p22S→R | 20.0 at 500 µM |
| 15 | KKKKPARVGL GITTVLTRTT QS | $NK_4$ p22M→R | <1.0 at 500 µM |
| 16 | KKKKARSGSS QTTMTLVTTI GLGVRAP | $NK_4$bLa | NT |
| 17 | ARSGSSQTTM TLVTTIGLGV RAPKKKK | $CK_4$bLa | 3.6 at 500 µM |

TABLE 1-continued

Activity profile in MDCK cells for Palindromic M2GlyR sequence module and variants

| Seq. ID # | Amino Acid Sequence | Name | Acitvity μA/cm2 |
|---|---|---|---|
| 18 | KKKKPARVGL GITTVLVTTI GLGVRAP | NK$_4$Ala | 17.4 at 100 μM |
| 19 | PARVGLGITT VLVTTIGLGV RAPKKKK | CK$_4$Ala | 43.3 at 200 μM |
| 20 | KKKKPARVGL GITTVLPARV GLGITTV | NK$_4$ALA | <1.0 at 500 μM |
| 21 | KKKKPARVGL GITTVLAARV GLGITTV | NK$_4$ALA' | 8.0 at 250 μM |
| 22 | KKKKVTTIGL GVRAPLPARV GLGITTV | NK$_4$aLA | <1.0 at 500 μM |
| 23 | KKKKARSGSS QTTMTLTMTT QSSGSRA | NK$_4$bLB | 4.2 at 500 μM |
| 24 | KKKKTMTTQS SGSRALARSG SSQTTMT | NK$_4$BLb | <1.0 at 500 μM |
| 25 | KKKKARSGSS QTTMTLARSG SSQTTMT | NK$_4$bLb | <1.0 at 500 μM |
| 26 | KKKKPARVGL GITTVLVTTI GLGVRAA | NK$_4$ALa' | 25.7 at 100 μM |
| 27 | KKKKAARVGL GITTVLVTTI GLGVRAA | NK$_4$A'La' | 20.3 at 100 μM |
| 28 | KKKKAARVGL GITTVVTTIG LGVRAA | NK$_4$A'a' | 17.3 at 100 μM |
| 29 | KKKKAARVGL GITTVLLVTT IGLGVRAA | NK$_4$A'LLa' | NT |
| 30 | KKKKAARVGL GITTVLLLVT TIGLGVRAA | NK$_4$A'LLLa' | NT |
| 31 | KKKKAARVGL GITTVLLLLV TTIGLGVRAA | NK$_4$A'LLLLa' | NT |
| 32 | KKKKPARVGL GITTVLTRTT (DAP)S | NK$_4$-p22Q→DAP | 24.0 at 500 μM |
| 33 | KKKKPARVGL GITTVLTMTT QSSGS | NK$_4$ p25 | 18.4 at 500 μM |
| 34 | KKKKPARVGL GITTVLTMTT QS | NK$_4$ p22 | 20.3 at 500 μM |
| 35 | KKKKPARVGL GITTVLTMTT Q | NK$_4$ p21 | 13.1 at 500 μM |
| 36 | KKKKPARVGL GITTVLTMTT | NK$_4$ p20 | 8.8 at 500 μM |
| 37 | KKKKPARVGL GITTVLTMT | NK$_4$ p19 | 8.7 at 500 μM |
| 38 | KKKKPARVGL GITTVLTM | NK$_4$ p18 | 6.8 at 500 μM |
| 39 | KKKKPARVGL GITTVLT | NK$_4$ p17 | 1.8 at 500 μM |
| 40 | KKKKPARVGL GITTVL | NK$_4$ p16 | 1.5 at 500 μM |
| 41 | RVGLGITTVL TMTTQSSGSR AKKKK | CK$_4$ p25 | 6.3 at 500 μM |
| 42 | GLGITTVLTM TTQSSGSRAK KKK | CK$_4$ p22 | 3.3 at 500 μM |
| 43 | LGITTVLTMT TQSSGSRAKK KK | CK$_4$ p21 | <1.0 at 500 μM |
| 44 | GITTVLTMTT QSSGSRAKKK K | CK$_4$ p20 | <1.0 at 500 μM |
| 45 | ITTVLTMTTQ SSGSRAKKKK | CK$_4$ p19 | <1.0 at 500 μM |
| 46 | LTMTTQSSGS RAKKKK | CK$_4$ p16 | <1.0 at 500 μM |
| 47 | KKKKPARVGL GITTVLTMTT QSSGSRAKKK K | NK$_4$/CK$_4$ p31 | 5.0 at 500 μM |
| 48 | PARVGLGITT V | A | <1.0 at 500 μM |
| 49 | TMTTQSSGSR A | B | <1.0 at 500 μM |
| 50 | VTTIGLGVRA P | a | <1.0 at 500 μM |
| 51 | ARSGSSQTTM T | b | <1.0 at 500 μM |
| 52 | AARVGLGITT V | A' | <1.0 at 500 μM |
| 53 | VTTIGLGVRA A | a' | <1.0 at 500 μM |

TABLE 1-continued

Activity profile in MDCK cells for Palindromic M2GlyR
sequence module and variants

| Seq. ID # | Amino Acid Sequence | Name | Acitvity µA/cm2 |
|---|---|---|---|
| 54 | KKKKPARVGLGITTVLTMTTQW | NK$_4$-p22S→W | |
| 55 | KKKKPARVGLGITTVLTMTTRW | NK$_4$-p22QS→RW | |

Modules:
A = PARVGLGITTV
A' = AARVGLGITTV
a = VTTIGLGVRAP
a' = VTTIGLGVRAA
B = TMTTQSSGSRA
b = ARSGSSQTTMT As shown by these results, many derivatives of the M2GlyR sequence exhibited much greater activity at lower peptide concentrations than the M2GlyR sequence (SEQ ID No. 1) and the lysine-modified M2GlyR sequences (SEQ ID Nos. 2 and 3). For example, SEQ ID No. 26 exhibited nearly twice the activity at one-fifth of the concentration. In comparing SEQ ID No. 26 with SEQ ID No. 3, both sequences include four lysine residues at the N terminus, followed by the first eleven residues of the M2GlyR sequence, followed by a leucine residue. However, SEQ ID No. 3 further includes the remaining eleven residues of the M2GlyR sequence while SEQ ID No. 26 includes the first eleven residues of the M2GlyR sequence, in reverse order with an alanine substituted for the C-terminal proline residue. Thus, the modifications of the lysine-modified M2GlyR sequence resulting in the derivative M2GlyR sequence (SEQ ID No. 26) reduced the amount of peptide necessary to generate a high activity level in cell monolayers.

Additionally, FIGS. 1-5 illustrate the effects of M2GlyR derived sequences on $I_{SC}$ in MDCK monolayers. Each of these figures represents one testing run for each of the identified sequences. The numbers along the abscissa represent the concentrations of peptide added at that point in the test. Total time along the abscissa is 5 minutes. The ordinate scale bar represents a 5 µA/cm² change in ion flux across the epithelium. The upward deflection of the $I_{sc}$ trace in response to peptide exposure is indicative of net anion secretion. As shown in these figures, the cell layer of FIG. 1 was unresponsive until exposed to 200 µM and a substantial increase in anion secretion was not observed until the epithelium was exposed to 500 µM. In contrast, the cell layer of FIG. 2 exhibits an almost immediate response when exposed to 100 µM peptide and exhibits a maximal increase in anion secretion when exposed to 200 µM peptide. An even greater response is shown by the cell layers of FIGS. 3 and 4, which both had maximal response to peptide concentrations of 100 µM.

Figure 2:
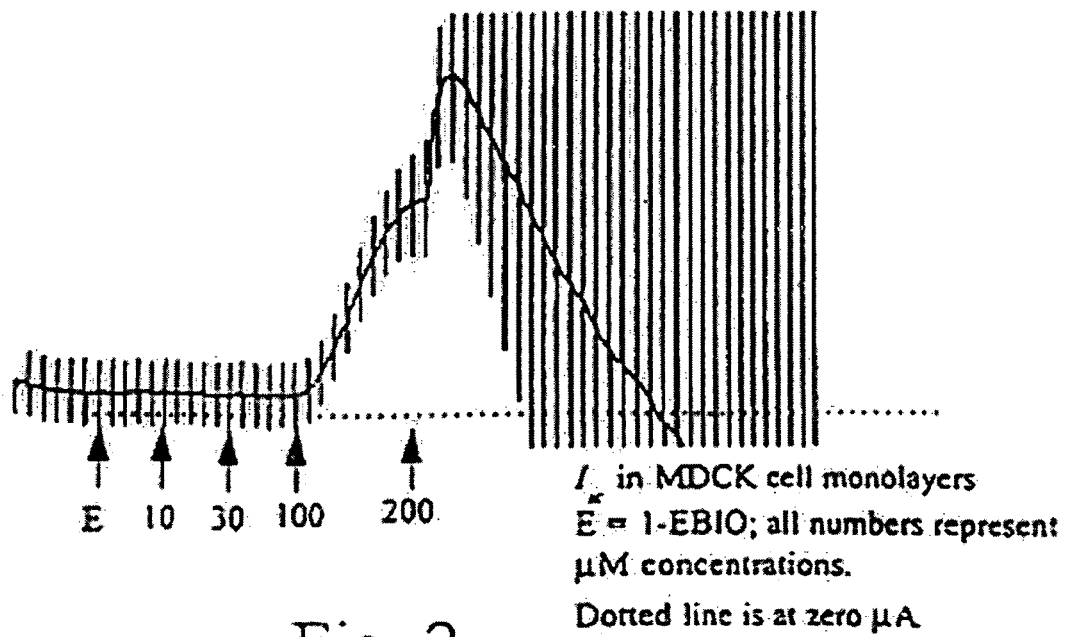
Figure 3:
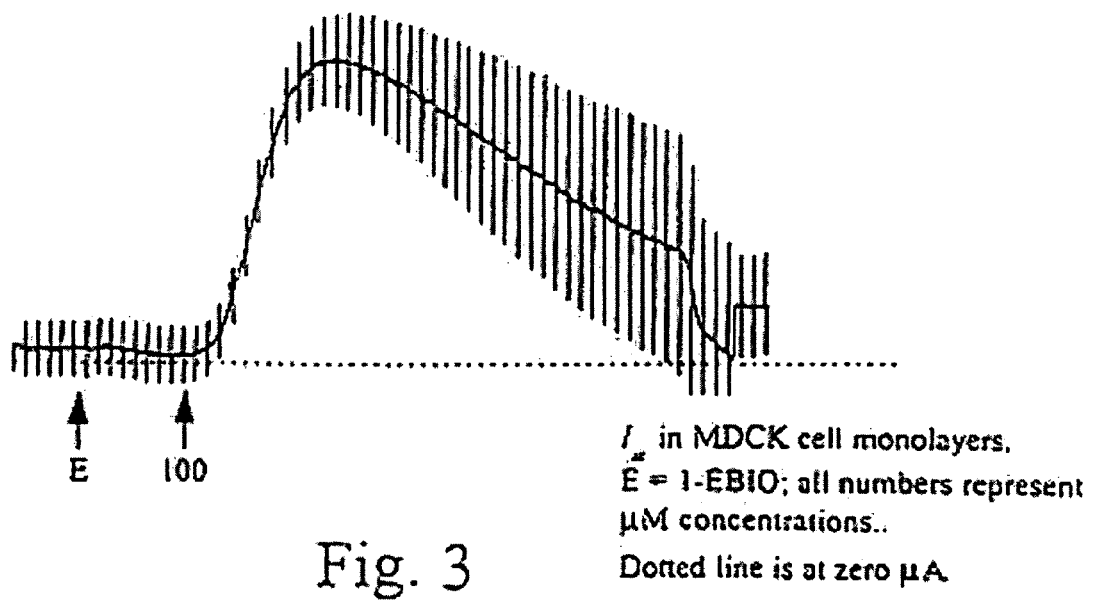
Figure 4:
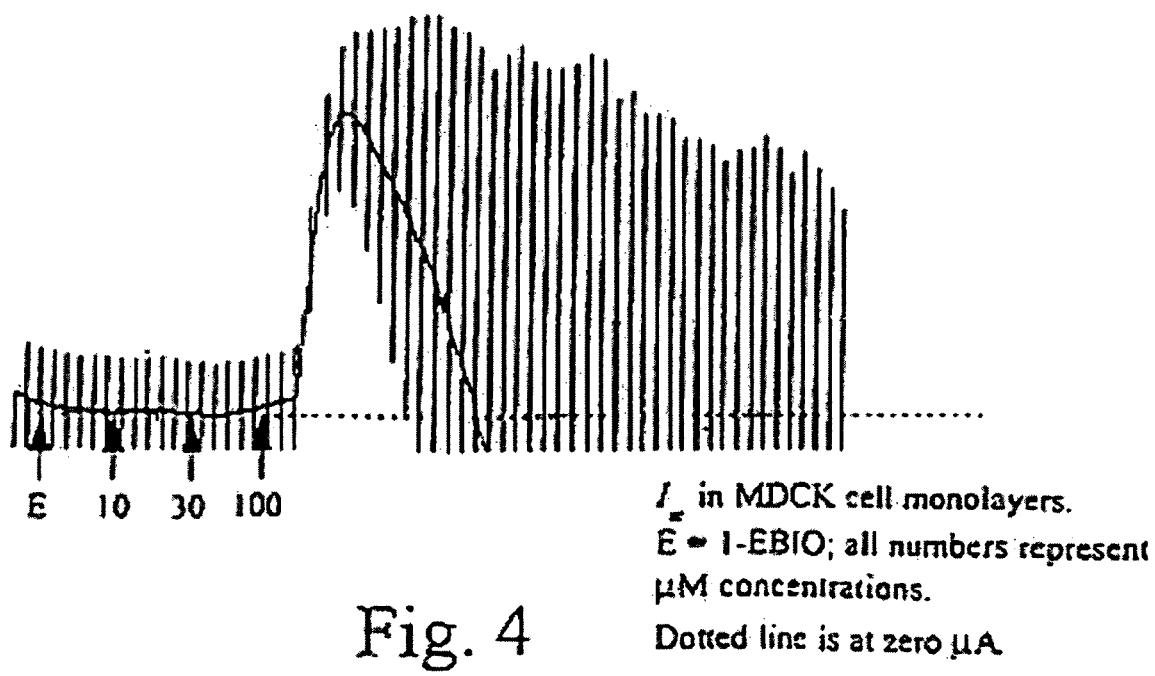
Figure 5:
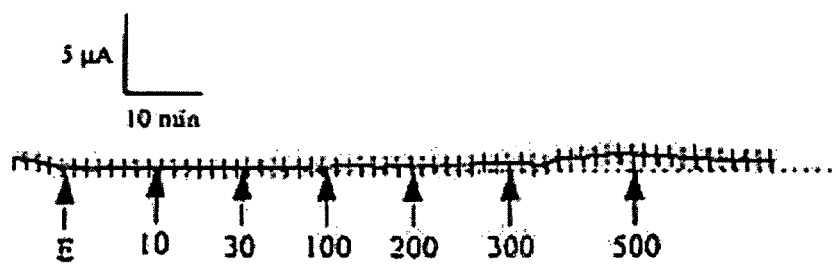

Another interesting result from these electrophysiology experiments was that the palindromic sequences generally reduced transepithelial electrical resistance ($R_{TE}$), likely due to modulation of cell-cell interactions at the tight junction. This effect is present to varying extents with different sequences. FIGS. 1-5 illustrate this result by the magnitude of the cross-hatch lines—line length is inversely proportional to $R_{TE}$. For example, FIGS. 1 and 3 show moderate effects of the respective peptides on $R_{TE}$. In contrast, FIG. 5 shows little change in $R_{TE}$ that accompanied peptide exposure. FIGS. 2 and 4 show greater effects of the peptides on $R_{TE}$. The change in ion transport in these figures is very rapid in onset and once maximum ion flux was observed, monolayer $R_{TE}$ declined to varying degrees. Peptide-induced changes in $R_{TE}$ reversed over time (1-48 hours) following peptide removal. Knowledge of these effects on $R_{TE}$ will aid in the design of peptide therapies directed to particular cell layers. For example, peptides causing a substantial reduction in the epithelial barrier function (indicated in this context by a reduction in $R_{TE}$) could be useful in providing access for therapeutic intervention to otherwise excluded tissues.

Example 2

This example determined the circular dichroism for various peptides generated using the methods of Example 1.

Materials and Methods

Circular dichroism: Circular dichroism spectra were recorded on a Jasco Model J-720 spectropolarimeter in the range 180-250 nm using quartz cuvettes with a 0.2 mm pathlength. Eight scans recorded at a rate of 20 nm/minute were averaged and corrected for contributions of buffer (10 mM HEPES, pH 7.2). Peptide concentrations of 50 µM in 20% TFE were used to determine the helical propensity of the different M2GlyR analogs. The molar ellipticity was calculated using d-10-camphorsulfonic acid (290.5=7783° cm2 dmol 1) as a reference (Chen, G. C., and J. T. Yang. 1977. Two point calibration of spectropolarimeter with d-10-camphorsulfonic acid. *Anal. Lett.* 10:1195-1207.). The line shapes of the spectra were analyzed using a least-square fitting routine by comparison to polylysine standards representing 100%-helix, -turn, or random coil, respectively.

Results

Figure 6:
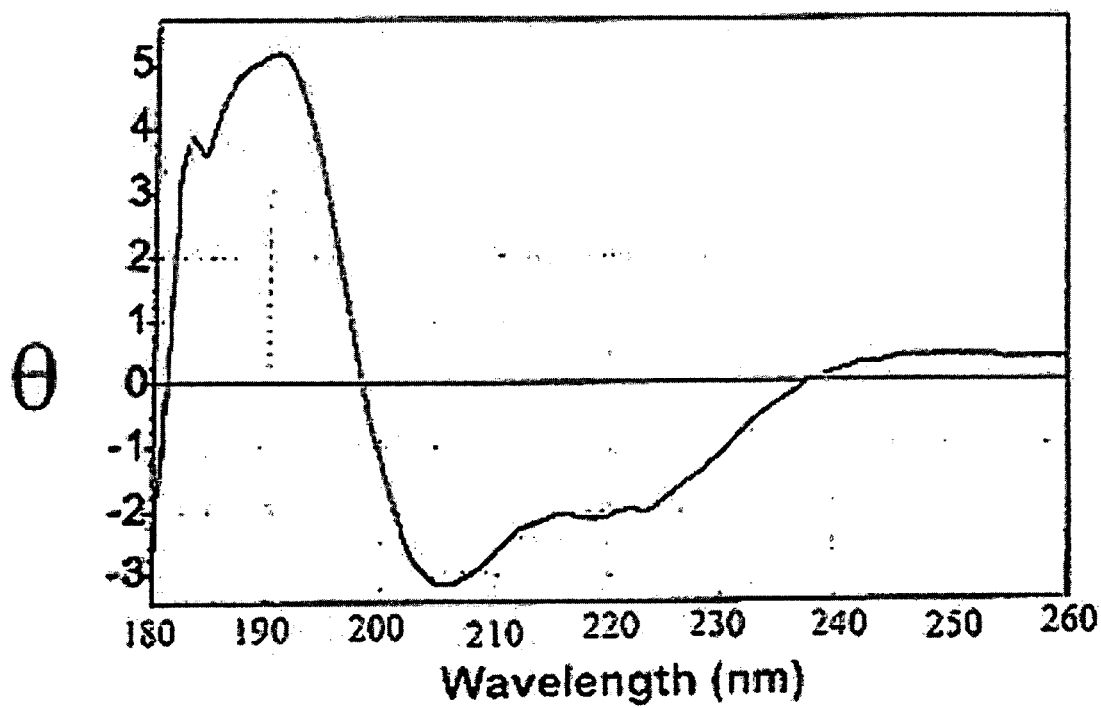
FIG. 6 is a circular dichroism spectra for a representative M2GlyR derivative depicting alpha helical content of an active peptide.
Figure 7:
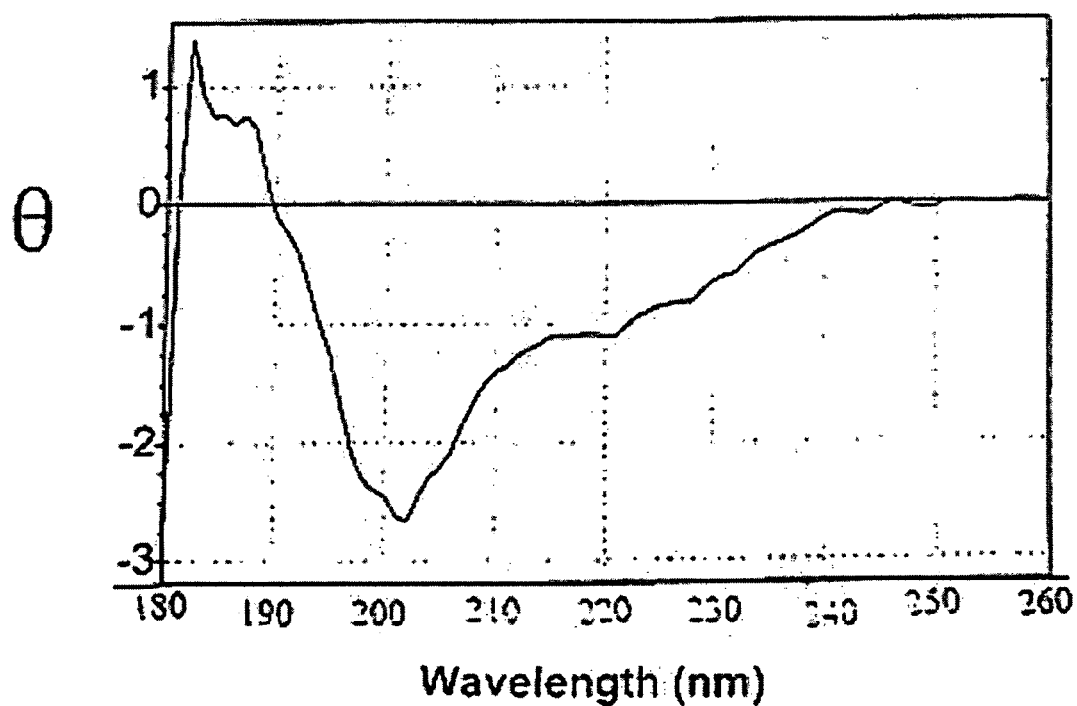
FIG. 7 is a circular dichroism spectra for a representative M2GlyR derivative depicting beta content of an inactive peptide.
Figure 8:
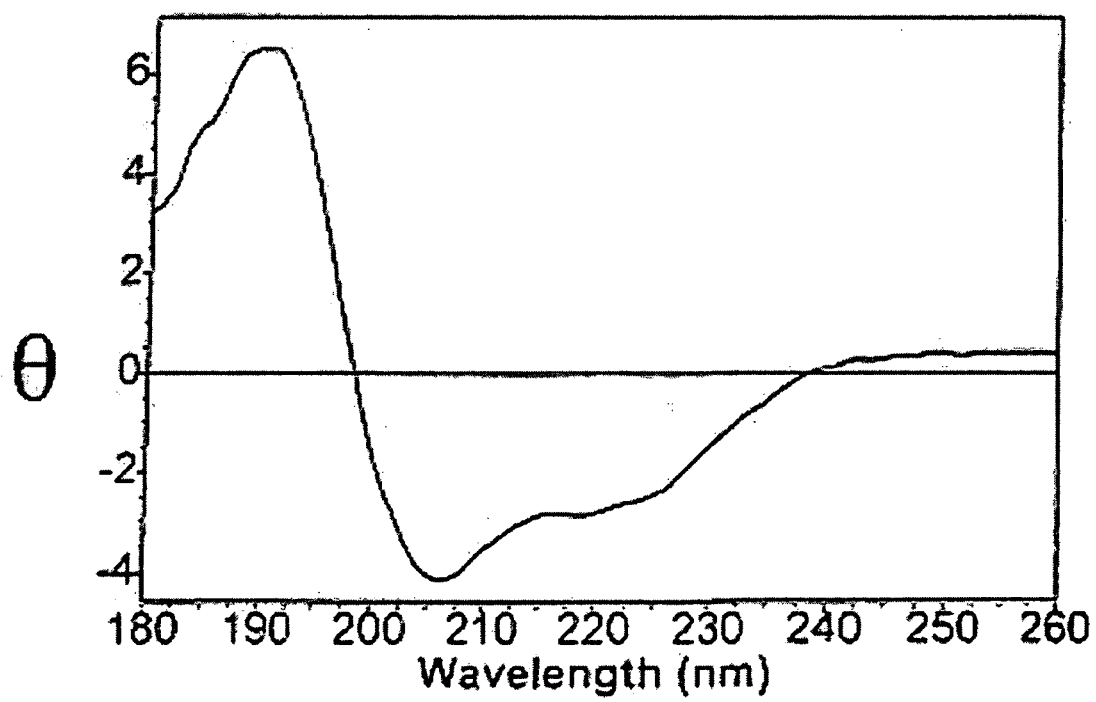
FIG. 8 is a circular dichroism spectra for a representative M2GlyR derivative depicting alpha helical content of an active peptide.

FIGS. 6-8 contain the circular dichroism spectra for three representative peptides. FIG. 6 shows the spectra for SEQ ID No. 26, FIG. 7 shows the spectra for SEQ ID No. 5, and FIG. 8 shows the spectra for SEQ ID No. 19. All spectra for these palindromes were determined in water containing 20% TFE. The spectra illustrated in FIGS. 6 and 8 are indicative of helical structure with minima at approximately 222 and 208 nm, respectively. Notably, each of these sequences are active in MDCK monolayers at 100 µM. These two sequences (SEQ ID Nos. 26 and 19) have their lysine caps on opposite ends but their helical content remains the same. In contrast, the spectra for SEQ ID No. 5 has its minima shifted, thereby indicating that the structure is not helical, but is rather beta-sheet. As shown in Table 1, this sequence (SEQ ID No. 5) has very little activity in MDCK monolayers. Thus, these results confirm that helical peptides, as determined by circular dichroism spectra, are much more active than non-helical sequences.

Example 3

This example determined the emission fluorescence spectra for peptide sequences generated using the methods of Example 1. This example also tested tryptophan containing peptides for their ability to associate with and insert into bilayers.

Materials and Methods

Fluorescence: Fluorescence was measured on a Hitachi Model F-4010 steady-state fluorescence spectrometer. All measurements were made in 10×10 mm quartz cuvettes at 37° C. Tryptophan fluorescence was excited at 280 nm with slits set to 5 nm. For samples containing vesicles, the background intensity was scaled appropriately and subtracted from the peptide-containing sample. Potassium iodide quenching measurements were performed by titrating a 4 M solution of KI, prepared daily, into a peptide solution and scanning the intensity of fluorescence from 300-400 nm stimulated by excitation at 280 nm. Stem-Volmer quenching constants $K_{S-V}$ were determined by linear regression with the equation $(F_0/F) = 1+K_{S-V}[I]$, where F is the fluorescence intensity in the presence of iodide, $F_0$ is the fluorescence in the absence of iodide, and [I] is the molar concentration of iodide.

Liposome studies: Liposomes are used to assess the propensity of different, tryptophan containing, channel-forming peptides to associate with and insert into bilayers. These events were followed using changes in the fluorescence intensity and emission maxima (blue shift) of the resident tryptophan residue. Lipids were obtained from Avanti Polar Lipids (Alabaster, Ala.) dissolved in chloroform and stored under nitrogen until used. A solution containing 1-palmitoyl-2-oleoyl-sn-glycero-3-phosphocholine (POPC; 22.5 wt %), 1-palmitoyl-2-oleoyl-sn-glycero-3-phosphoserine (POPS; 10 wt %) and 1-palmitoyl-2-oleoyl-sn-glycero-3-phosphoethanolamine (POPE; 67.5 wt %) was prepared and the chloroform was evaporated with nitrogen. Lipids were then hydrated at a concentration of 11.1 mMol/L in a loading buffer containing (in mMol/L) 100 NaCl, 10 HEPES pH 7.4, for 60 minutes at 50° C. Large unilamaellar lipid vesicles were prepared by extrusion through a 2 μm polycarbonate filter 17 times, then centrifuged at 37,500 rpm (125,000×g) in a TA865 rotor in a Sorvall ultracentrifuge (DuPont, Wilmington, Del.) for 60 minutes at 4° C. The supernatant was removed by aspiration and the pellet dissolved in external buffer.

For the peptide-liposome fluorescence studies are performed at 37° C. Buffer containing the liposomes were used to zero the instrument. Peptide is added to liposomes in heated cuvette and allowed to incubate for 10 minutes before scanning. Peptide concentrations were varied from a low of 5.0 μM up to a maximum of 300 μM. The lipid to protein Molar ratio varied from 2,200:1 at the lowest protein concentration up to 40:1 at the highest peptide concentration. Fluorescence quenching using potassium iodide (4.0 M stock) was also performed as described in the fluorescence section above.

Results

Figure 9:
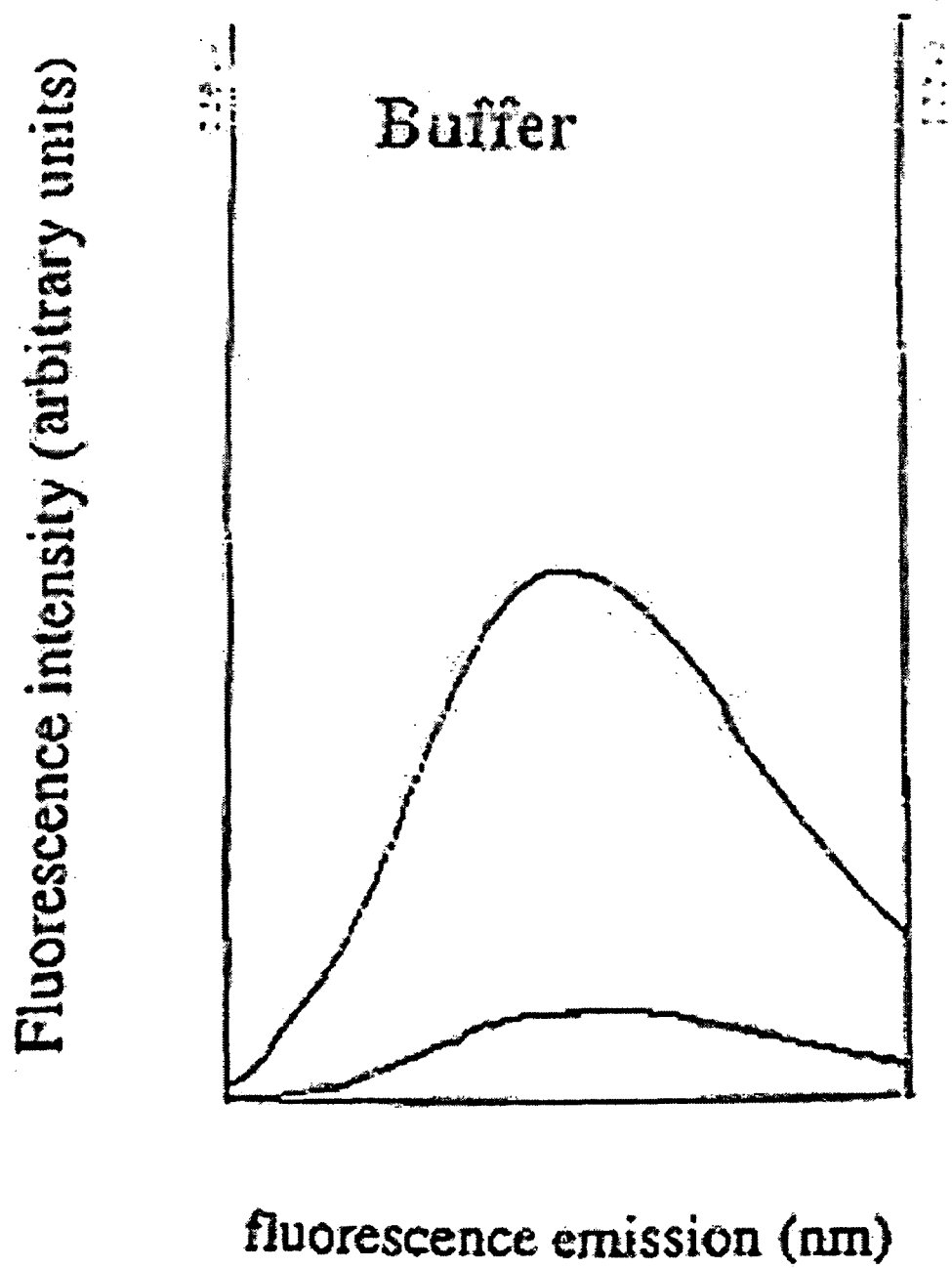
FIG. 9 is a graph of the fluorescence emission properties of a representative M2GlyR derivative in buffer illustrating the effect of a quencher agent.

FIG. 9 is the emission fluorescence spectra for SEQ ID No. 9 in aqueous buffer and in presence of 1 mM liposomes (90% POPC and 10% POPS). Buffer in both cases is 10 mM HEPES, 100 mM KCl at pH 7.4. Upper tracing in each panel has peptide (6.25 micromolar). Bottom tracing has final potassium iodide (KI) at a final concentration of 50 mM. KI is added to quench the fluorescence of the tryptophan residue.

As shown in FIG. 9, the tryptophan in buffer has a 348.4 nm lambda max. This value is consistent with the tryptophan (W) being fully exposed to solvent. The intensity is 148.0 (this is in arbitrary units). The near complete quenching (illustrated by the lower line) with 50 mM KI confirms the full exposure of W to solvent. Thus, once the KI was added, the lambda max changed to 357.0 nm and the intensity dropped to 26.7.

Figure 10:
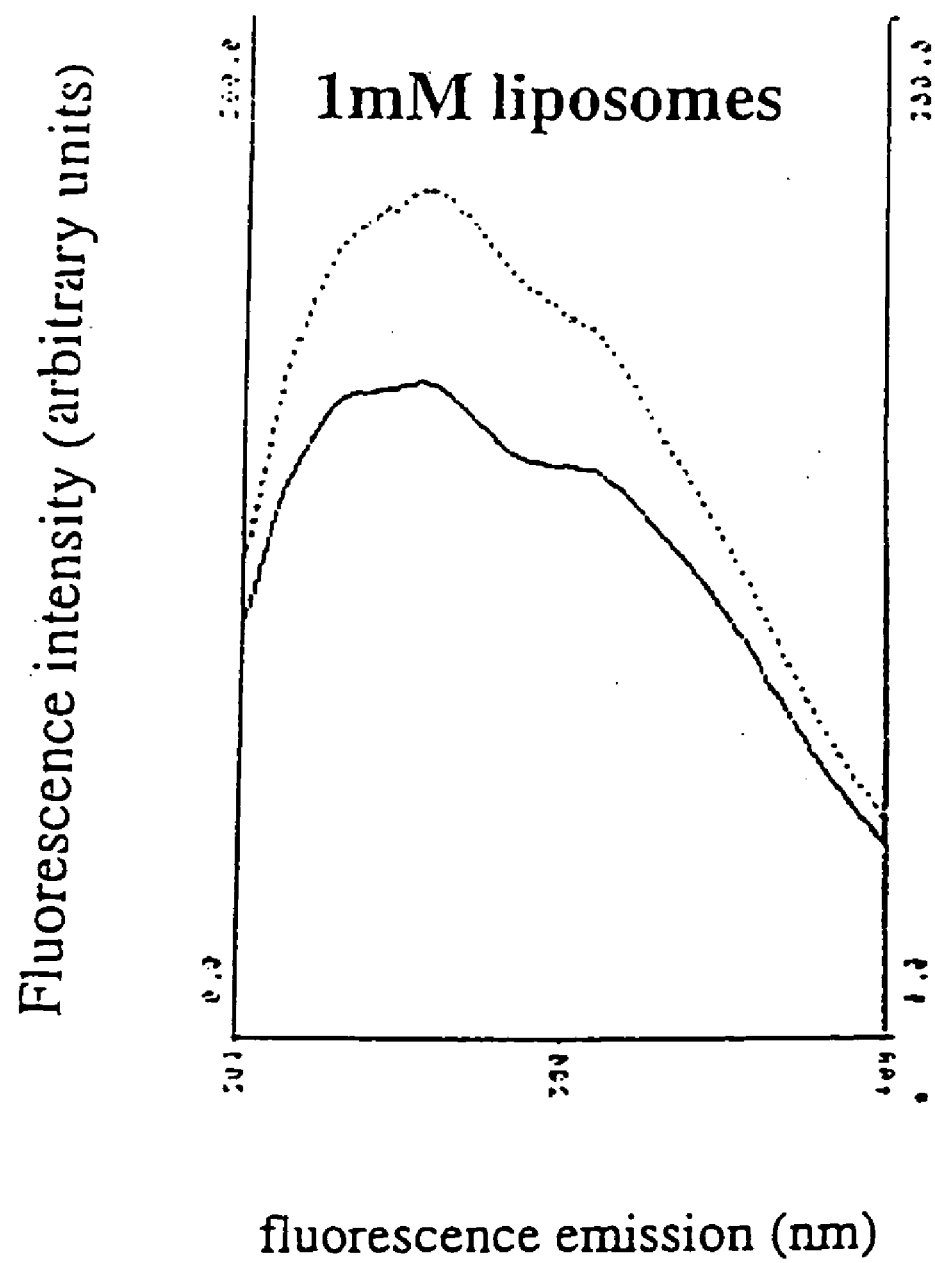
FIG. 10 is a graph of the fluorescence emission properties of a representative M2GlyR derivative in liposomes illustrating the effect of a quencher agent.

When the peptide is added to liposomes, the lambda max decreases slightly, however, the intensity is greatly increased. Additionally, the addition of the quenching agent does not have as great of an effect on the peptide in the buffer solution. As shown in FIG. 10, there is both a blue shift of the lambda max to 327.8 nm (so-called blue shift) with a doubling of the fluorescence intensity to approximately 249.0. This large shift in the presence of lipid indicates that the W residue is buried in the membrane. When the quenching agent (KI) is added, the intensity decreases to 193.0 and the lambda max drops only 0.4 nm to 327.4 nm. The weak quenching with KI indicates a shielding from solvent which is not membrane permeable, thereby confirming the membrane association of the W. The very large blue shift also suggests a deep burying, which suggests that the peptide is in a transmembrane or membrane spanning configuration as opposed to a simple membrane association without insertion. Additionally, the binding of the peptide to the membrane is almost instantaneous, as shown by the rapid onset of fluorescence.

Example 4

This example determined the amount of aggregation exhibited by peptides generated using the methods of Example 1.

Materials and Methods

Chemical cross-linking: In order to visualize the oligomeric state of the peptide in solution a chemical cross-linking protocol was developed. Calculated amounts of each peptide were weighted out and dissolved in 1 mL of distilled water to make 1 mM stock solutions. A 100 mM stock solution of the chemical crosslinking reagent Bis[Sulfosuccinimidyl]suberate, $BS^3$, (Pierce Chemical Co., Rockford, Ill.) was prepared in dimethyl sulfoxide (DMSO). In typical reactions, 5-30 μL of 1.0 mM stock solution of peptide are added to 64-94 μL of 10 mM HEPES buffer, pH 8.1 to give a range of concentrations starting at 50 μM rising up to 300 μM. Sample were allowed to sit at room temperature for 15 minutes. 1-6 μL of 100 mM $BS^3$ was then added to the previously prepared peptide such that the crosslinking reagent was present in 20-fold excess. The final volume for each reaction was 100 μL. After reacting for 30 minutes, the reaction was stopped with the addition of 10 μL 1.0 N HCl. Each sample was then vacuum dried. Later dry samples were re-dissolved in 60 μL of distilled water along with 60 μL of a 2×-tricine SDS sample buffer (Novex, San Diego). All samples were then boiled at 100° C. for 5 minutes. 5 μL aliquots of each SDS boiled sample was then loaded into separate lanes of pre-cast, 1.0 mm, 10 well, 10-20% tricine gels (Novex, San Diego). Pre-made Novex tricine-SDS buffer was used in the electrophoresis. The reference well contained 1 μL of MultiMark® multi-colored molecular weight standard (Novex, San Diego). The electrophoresis was carried out at a constant 110 Volts for 90 minutes. The gel was then fixed in 40% methanol in water and the cross-linked peptides visualized using silver staining (SilverXpress® silver staining kit, Invitrogen, Carlsbad, Calif.).

Results

Figure 11:
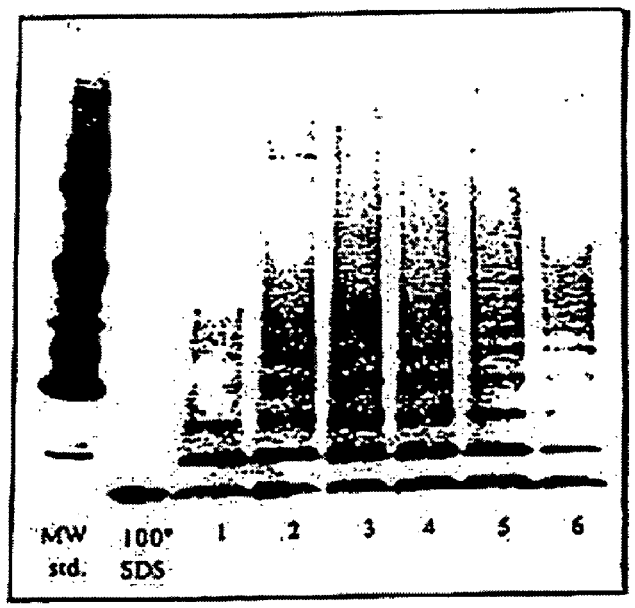
FIG. 11 is a photograph of an SDS-PAGE illustrating the multimeric species of representative M2GlyR derivatives.
Figure 11:
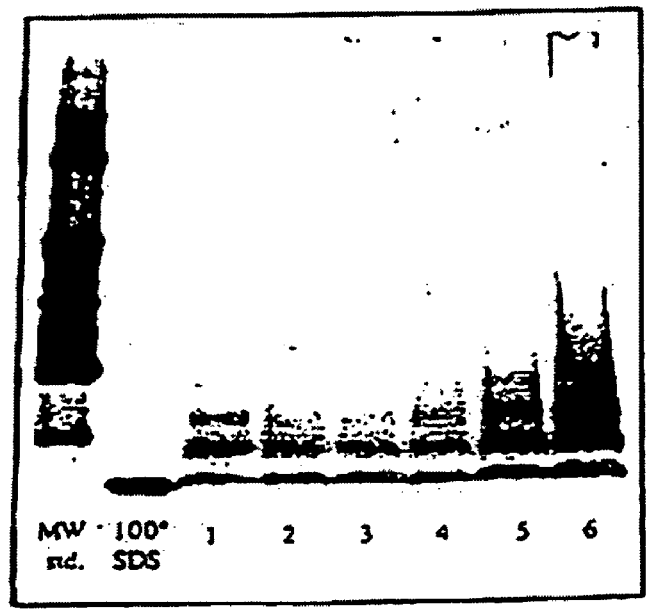
Figure 12:
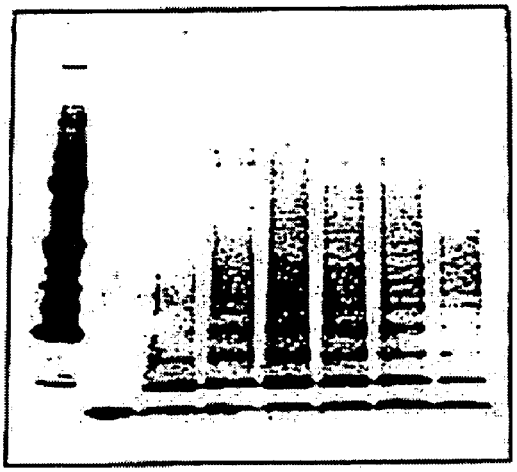
FIG. 12 is a photograph of an SDS-PAGE illustrating the multimeric species of representative M2GlyR derivatives.
Figure 12:
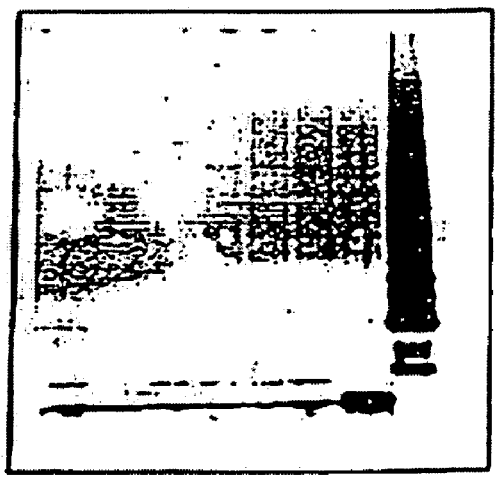

Representative results for this Example are provided in FIGS. 11 and 12, which illustrate the aggregate numbers for SEQ ID Nos. 2, 3 and 18. Physical data from other experiments support the modeling data described above. As shown by FIG. 11, N-$K_4$ M2GlyR (SEQ ID No. 3) gave a ladder of bands starting from monomer up to assemblies approaching 36 kDa. However, C-$K_4$ M2GlyR (SEQ ID No. 2) showed only trace amounts of aggregates higher than trimer. Assuming that the lysines are participating in hydrogen bonds with the backbone carbonyls, two postulates can be proposed; 1) the lysine ε-amino groups are not readily available for cross-linking, or 2) the lysine C-capping disrupts the ability to form the pores in membranes or form aggregates in solution. FIG. 12 compares the results for SEQ ID No. 3 with a palindrome of that sequence, SEQ ID No. 27. SEQ ID No. 27 is related to SEQ ID No. 3 in that the first 12 residues (the first 11 residues comprise module A and the 12th is leucine) are identical and the remaining 11 amino acid residues are the A module in reverse. The result is a decrease in multimers as SEQ ID No. 3 comprised 12 or more aggregates while SEQ ID No. 27 was >90% monomeric with only a trace of dimer. As the number of aggregates decreased, the activity increased greatly (see Table 1).

Figure 13:
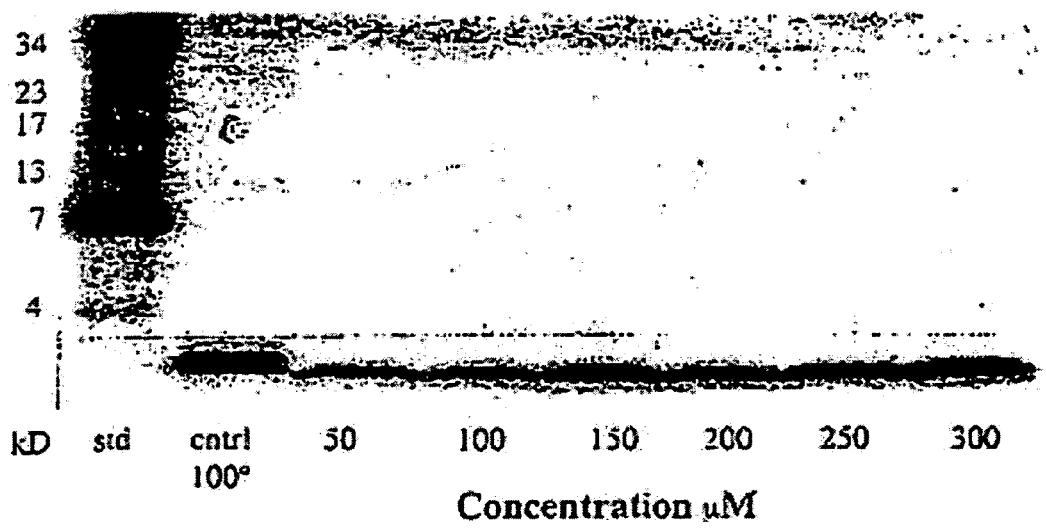
FIG. 13 is a photograph of a gel illustrating the concentration dependence of cross-linking of a representative M2GlyR derivative.
Figure 14:
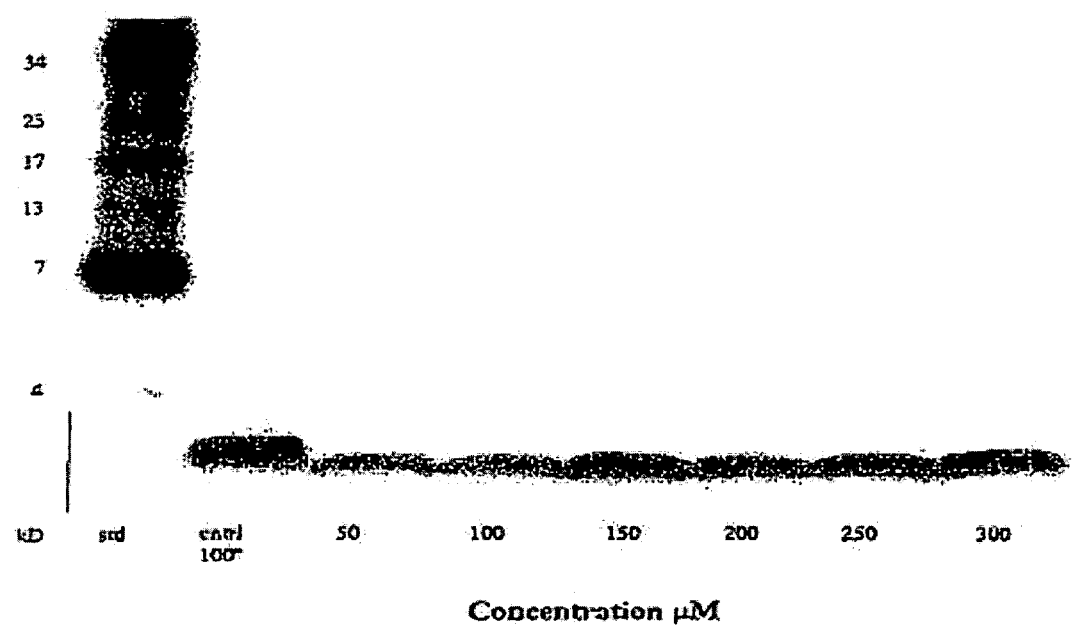
FIG. 14 is a graph illustrating the concentration dependence of cross-linking SEQ ID No. 19.

Other representative figures for this Example are FIGS. 13 and 14 which illustrate the concentration dependence of cross-linking for SEQ ID Nos. 9 and 19, respectively. As shown in these Figures, increasing concentrations of the peptide did not result in peptide aggregation and the peptides remained in monomer form. As monomeric forms tend to have higher levels of activity, the stability of SEQ ID No. 9 at high concentrations would indicate relatively high activity. This was, in fact, the case for SEQ ID No. 9 which has an activity of 20.0 μA/cm² at a concentration of 100 μM.

SDS-PAGE gels of the cross-linked peptide of SEQ ID No. 19 revealed that the N-$K_4$ A•L•a peptide is >90% monomeric with only a trace of dimer and nothing higher. FIG. 14 illustrates the concentration dependence of SEQ ID No. 19. In this figure, A' and a' have had their terminal prolyl residue replaced by an alanine.

Example 5

This example illustrated anion selective channel forming activity by selected peptides at concentrations below 500, below 300, and below 100 μM in accordance with the invention.
Materials and Methods
MDCK cells were cultured as a confluent polarized monolayer on permeable Snapwell™ supports. The culture medium was a 1:1 mixture of DMEM and Ham's F-12 (Gibco BRL, Grand Island, N.Y.) supplemented with 5% heat inactivated fetal bovine serum (BioWhittaker, Walkersville, Md.), and 1% penicillin and streptomycin (Gibco BRL). Cells were incubated in DMEM/F-12 supplemented with FBS and antibiotics (changed every other day) for 2-3 weeks prior to being mounted in modified Ussing flux chambers.

Transepithelial ion transport was evaluated in a modified Ussing chamber (Model DCV9, Navicyte, San Diego, Calif.). The Ussing chamber's fluid resistance compensation was completed in Ringer solution (composition (in mM) was 120 NaCl, 25 NaHCO₃ 3.3 KH₂PO₄, 0.8 K₂HPO₄, 1.2 MgCl₂, 1.2 CaCl₂). For electrical measurements cell monolayers were bathed in Ringer solution maintained at 37° C. and continuously bubbled with 5% $CO_2$:95% $O_2$. The transepithelial membrane potential ($V_{te}$) was clamped to zero and the transepithelial short circuit current ($I_{sc}$), an indicator of net ion transport, was measured continuously with a voltage clamp apparatus (Model 558C, University of Iowa, Department of Bioengineering, Iowa City, Iowa). Data were digitally acquired at 1 Hz with a Macintosh computer (Apple Computer, Cuppertino, Calif.) using Aqknowledge software (ver. 3.2.6, BIOPAC Systems, Santa Barbara, Calif.) with an MP100A-CE interface.

MDCK cell monolayers (in the presence of 1-EBIO to maximize basolateral membrane K⁺ conductance) were exposed on the apical aspect to escelating peptide concentrations. Maximal change in $I_{sc}$ (relative to the $I_{sc}$ prior to peptide exposure) was recorded following each increment in apical peptide concentration. The change in $I_{sc}$ as a function of peptide concentration was fitted to a modified Hill equation of the following form.

$$I_{sc} = I_{scmax}\left[\frac{[\text{peptide}]^n}{K_D^n + [\text{peptide}]^n}\right]$$

Figure 15:
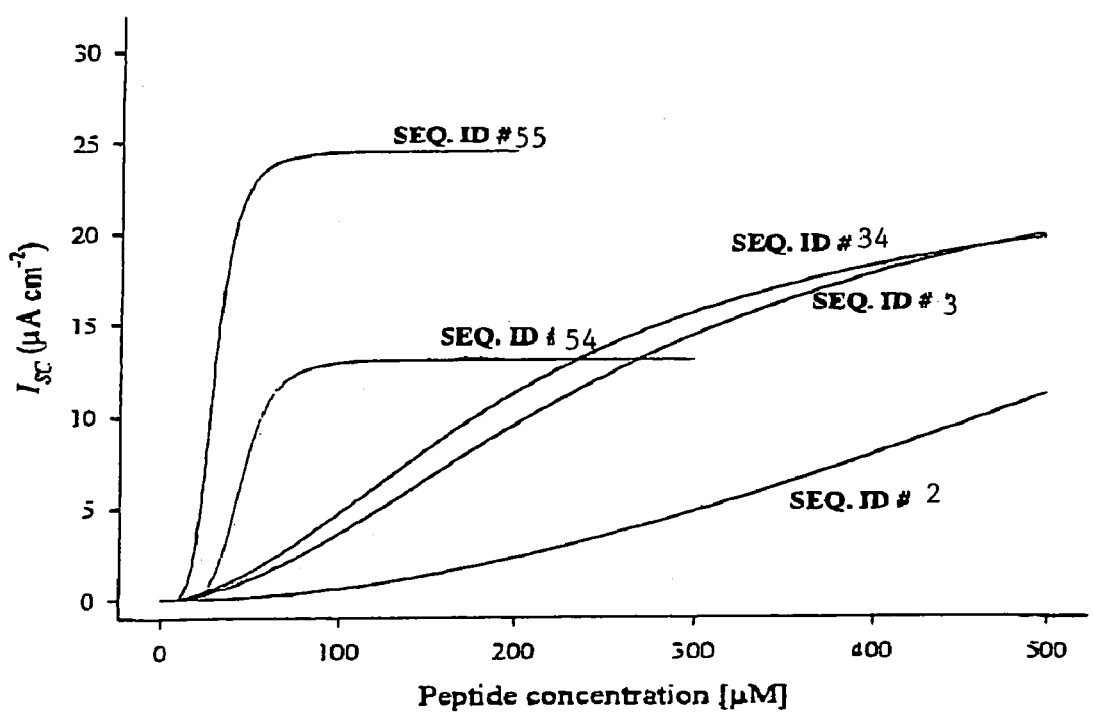
FIG. 15 is a graph illustrating the anion conductance of varying concentrations of M2GlyR derived peptides in accordance with the present invention.

Lines in FIG. 15 represent the best fit of the equation to the data set associated with each peptide as indicated.
Results
Certain of the sequences (SEQ ID Nos. 9, 18, 19, 26, 27, 54, and 55) exhibited the ability to induce a substantial (i.e., >15 μA/cm²) increase in $I_{sc}$ and some sequences (SEQ ID Nos. 54 and 55) produced maximal effects at concentrations of less than 100 μM.

Example 6

This example illustrated the effect of certain peptides in accordance with the invention on $I_{SC}$ and $R_{TE}$.
Materials and Methods
MDCK cells were cultured as a confluent polarized monolayer on permeable Snapwell™ supports. The culture medium was a 1:1 mixture of DMEM and Ham's F-12 (Gibco BRL, Grand Island, N.Y.) supplemented with 5% heat inactivated fetal bovine serum (BioWhittaker, Walkersville, Md.), and 1% penicillin and streptomycin (Gibco BRL). Cells were incubated in DMEM/F-12 supplemented with FBS and antibiotics (changed every other day) for 2-3 weeks prior to being mounted in modified Ussing flux chambers.

Transepithelial ion transport was evaluated in a modified Ussing chamber (Model DCV9, Navicyte, San Diego, Calif.). The Ussing chamber's fluid resistance compensation was completed in Ringer solution (composition (in mM) was 120 NaCl, 25 NaHCO₃ 3.3 KH₂PO₄, 0.8 K₂HPO₄, 1.2 MgCl₂, 1.2 CaCl₂). For electrical measurements cell monolayers were bathed in Ringer solution maintained at 37° C. and continuously bubbled with 5% $CO_2$:95% $O_2$. The transepithelial membrane potential ($V_{te}$) was clamped to zero and the transepithelial short circuit current ($I_{sc}$), an indicator of net ion transport, was measured continuously with a voltage clamp apparatus (Model 558C, University of Iowa, Department of Bioengineering, Iowa City, Iowa). Data were digitally acquired at 1 Hz with a Macintosh computer (Apple Computer, Cuppertino, Calif.) using Aqknowledge software (ver. 3.2.6, BIOPAC Systems, Santa Barbara, Calif.) with an MP100A-CE interface.

Figure 16:
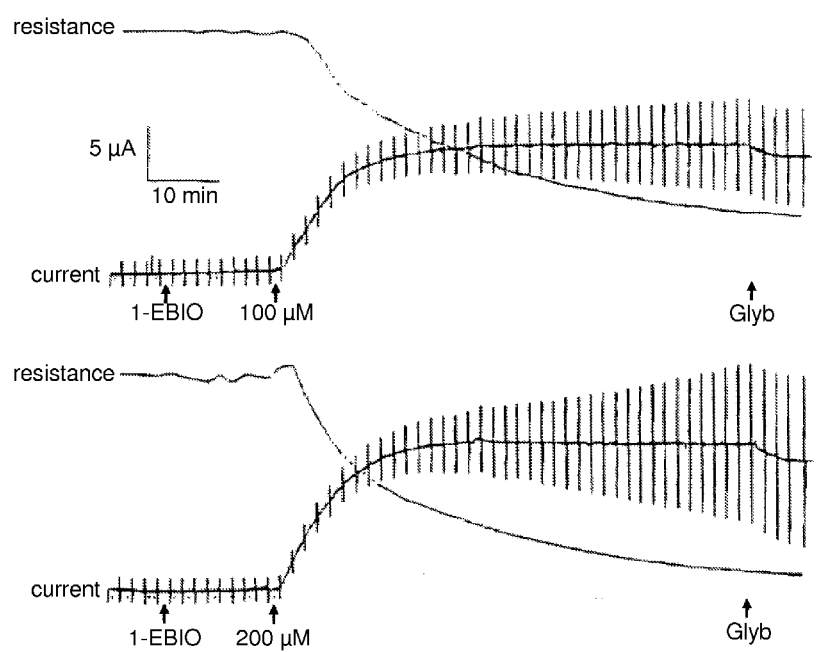
FIG. 16 is a graph illustrating the concentration effect of a peptide in accordance with the present invention on $I_{SC}$ and $R_{TE}$.
Figure 17:
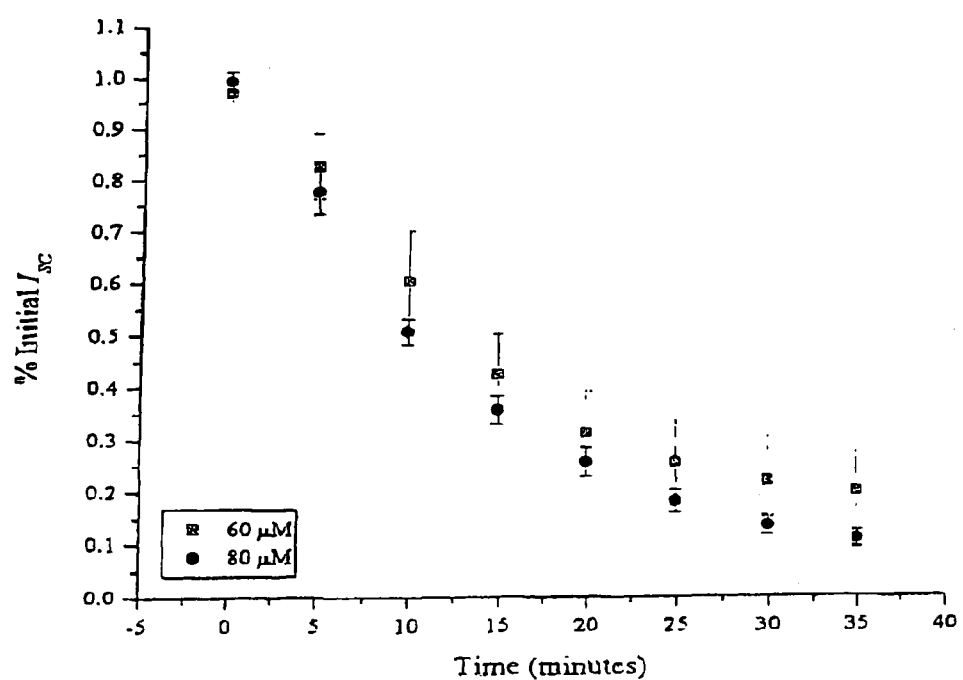
FIG. 17 is a graph illustrating the time dependent decrease in $R_{TE}$ induced by a peptide in accordance with the present invention.

MDCK cell monolayers (in the presence of 1-EBIO to maximize basolateral membrane K⁺ conductance) were exposed on the apical aspect to various concentrations of selected peptides as indicated.
Results
FIG. 16 illustrates the effect of SEQ ID No. 55 on $I_{SC}$ and $R_{TE}$. This sequence induced a ~70% and ~90% decrease in $R_{TE}$ at 100 and 200 μM, respectively, across MDCK monolayers. Such data indicate that a single peptide of this invention can affect both anion secretion across an epithelial monolayer and transepithelial electrical resistance. Both effects of the peptide are concentration dependent although the time frame of these two effects is different. As shown by FIG. 17, other peptides exhibited similar effects. However, the effect on the time-dependent decrease in $R_{TE}$ exhibited by certain of these peptides (with FIG. 17 showing the results for SEQ ID No. 27) at slightly lower concentrations (60 and 80 µM, respectively) indicates a strong concentration dependence on residual resistance.

Example 7

This example tested whether the change in $R_{TE}$ as a result of peptide exposure was permanent or reversible.
Materials and Methods
MDCK cells were cultured as a confluent polarized monolayer on permeable Snapwell™ supports. The culture medium was a 1:1 mixture of DMEM and Ham's F-12 (Gibco BRL, Grand Island, N.Y.) supplemented with 5% heat inactivated fetal bovine serum (BioWhittaker, Walkersville, Md.), and 1% penicillin and streptomycin (Gibco BRL). Cells were incubated in DMEM/F-12 supplemented with FBS and antibiotics (changed every other day) for 2-3 weeks prior to flux analysis.

Figure 18:
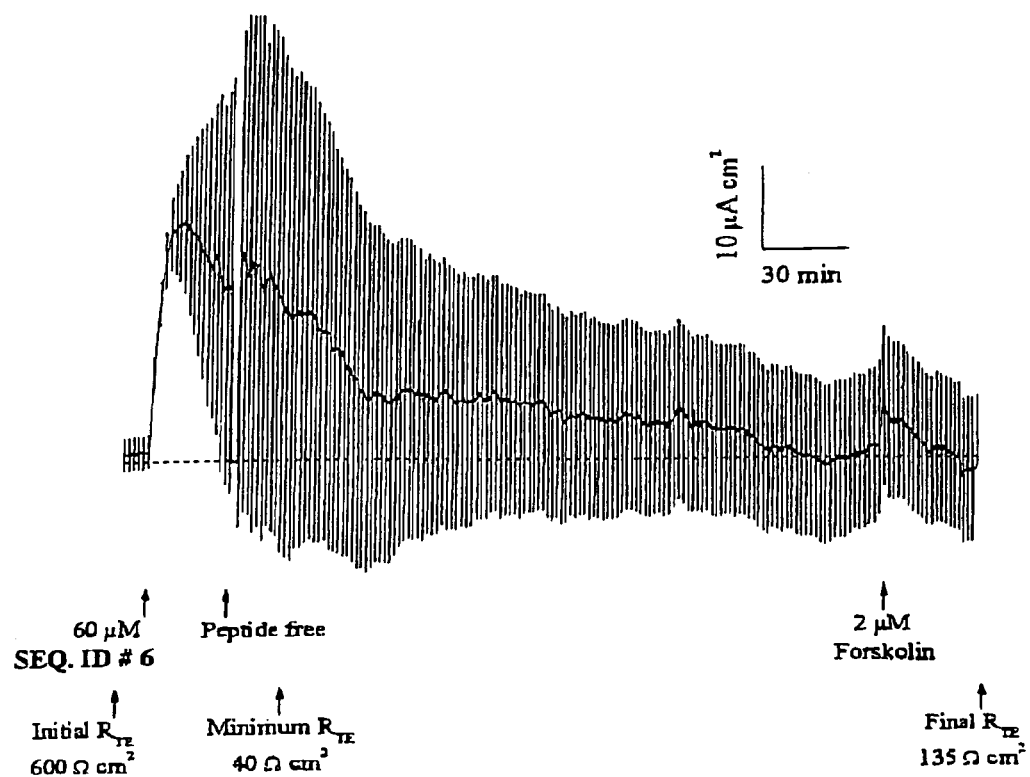
FIG. 18 is a graph illustrating the recovery of $R_{TE}$ in MDCK cells after the removal of peptide.

In this experiment, the MDCK monolayers were initially incubated with 60 µM of SEQ ID No. 27. When the residual resistance reached approximately 10% of the starting value, the peptide was removed by aspiration and followed by the addition of pre-warmed Ringer solution. This solution was subsequently removed and replaced an additional five times over the next 2 minutes. $I_{sc}$ was then monitored for the next 6 hours with the results given in FIG. 18. In this figure, the solid central line represents the measured current at zero mV and the vertical deflections represent the current recorded during periodic 1 mV bipolar pulses. Pulse amplitude is inversely proportional to $R_{TE}$ in accordance with Ohm's law.
Results
FIG. 18 shows that at the beginning of this reaction, the vertical bars were small and reflected a transepithelial electrical resistance of 600 $\Omega cm^2$. As peptide was added to the apical surface, the measured current increased rapidly, indicative of anion secretion. As the current approached its highest value, $R_{TE}$ began to drop. Based upon circuit analysis (that models the epithelial monolayer as a parallel construction of the paracellular pathway that is a purely resistive element and the transcellular pathway that is composed of the apical and basolateral membrane, in series, each modeled as a series capacitor and resistor) the insertion of apical ion channels is expected to result in a modest reduction in $R_{TE}$. However, the $R_{TE}$ change was far greater than would be predicted by this model. The minimum $R_{TE}$ observed was 40 $\Omega cm^2$, measured shortly after the peptide was removed from the apical bathing solution. After about an hour, post peptide treatment, $R_{TE}$ began to slowly increase, as illustrated by the decreasing length of the vertical deflections. After six hours, the resistance increased to 135 $\Omega cm^2$. This experiment clearly showed that resistance loss is reversible and recovery begins shortly after the effecting peptide is removed from the system. It was found that complete recovery of resistance takes less than 48 hours.

Example 8

Figure 19:
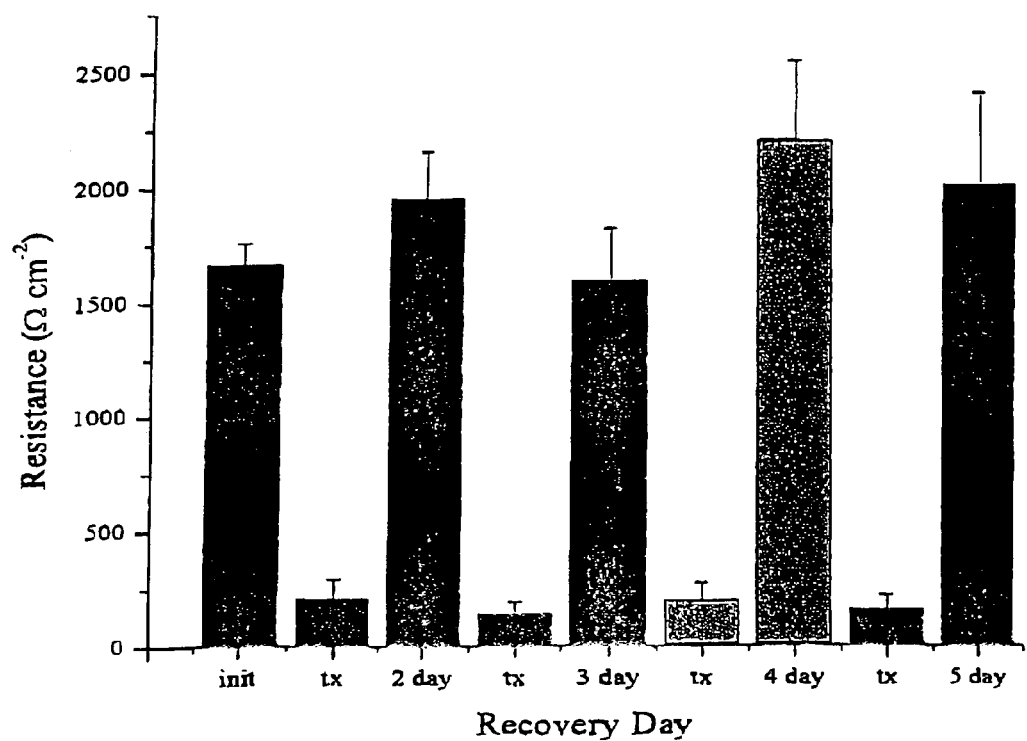
FIG. 19 is a graph illustrating the effect of repeated peptide administration to epithelial cell monolayers on recovery of $R_{TE}$.

This example tested the reversibility of resistance loss on a number of polarized epithelial monolayers.
Materials and Methods
Additional experiments have been conducted to test for complete reversibility of peptide-induced changes in $R_{TE}$. Monolayers were exposed to peptide (60 µM) in an Ussing chamber for ~20 minutes to document decreases in $R_{TE}$, recovered and returned to the cell culture incubator for two to five days with the apical and basolateral media refreshed daily before subsequent assessment of basal $R_{TE}$ and responsiveness to peptide. In the previous example, the return of $R_{TE}$ was only followed for hours. In this example, the restoration of $R_{TE}$ was measured over days to determine the minimum time require for full recovery.
Results
Results presented in FIG. 19 show that the initial $R_{TE}$ was >1500 $\Omega cm^2$ and that exposure to peptide caused $R_{TE}$ to decrease to <200 $\Omega cm^2$, in every case. Forty eight hours appears to be an adequate period for complete restoration of monolayer resistance. In every case, 2, 3, 4, and 5 post treatment, basal $R_{TE}$ was >1500 $\Omega cm^2$ and in every case, the previously treated monolayers responded indistinguishably from monolayers that had not previously been exposed to a channel-corming peptide. This experiment also demonstrated that the same monolayer can be subjected to repeated treatments without affecting its maximal resistance as the resistance of same monolayer subjected to repeated treatments returned to resistance levels and responsiveness equaling these parameters of the epithelium prior to peptide treatment.

Example 9

Figure 20:
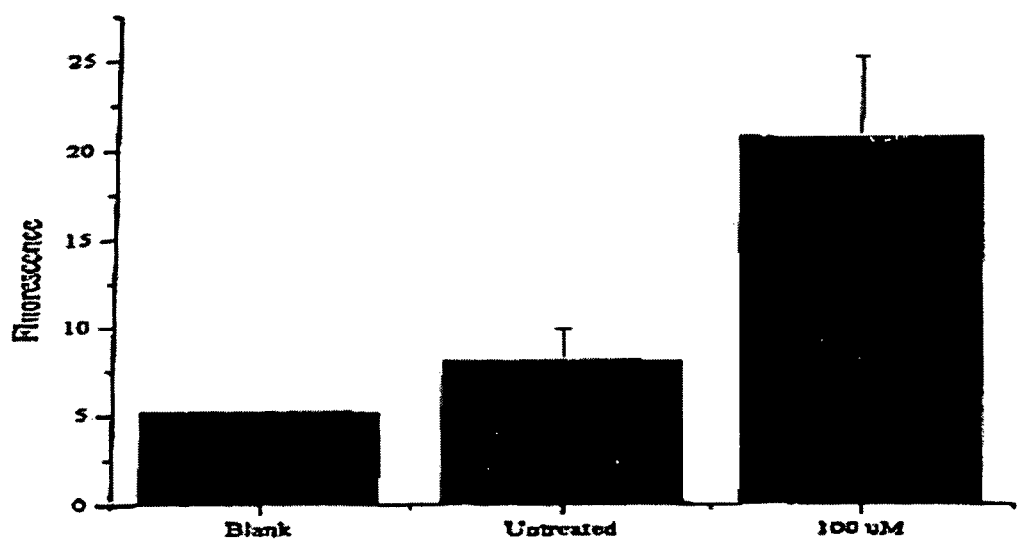
FIG. 20 is a graph illustrating the effect of peptide administration to a monolayer and the subsequent modulation of the tight junctions therein.

This example demonstrated the ability of a high molecular weight reporter molecule to cross epithelial cell monolayers only after peptide exposure.
Materials and Methods
Confluent MDCK cell monolayers were washed once with Ringer solution and placed in one of three treatments containing FITC-conjugated dextran (Sigma Chemical Co.) in the apical compartment; 1, Ringer solution in the apical and basolateral compartments; 2, Ringer solution apical and basolateral with SEQ ID No. 27 (also referred to herein as NC-1059) (100 µM) in the apical solution; 3, EDTA (3 mM) in Ringer solution that had been diluted 1:1 with distilled water in both the apical and basolateral compartments. Monolayers are incubated at 37° C. for 60 minutes and the solution in the basolateral well sampled to quantify fluorescently labeled dextran. Monolayers are then washed with Ringer solution to remove peptide, EDTA, and dextran, placed in tissue culture medium and returned to the incubator for two days before the assay was conducted again.
Results
FIG. 20 illustrates the results of this experiment for SEQ ID No. 27. Peptide exposure caused a substantial increment in transepithelial flux of FITC-labeled 9.5 kDa dextran over a 60 minute assay period, although less than half that observed across paired monolayers exposed to 3 mM EDTA in hypotonic Ringer solution (50% dilution with $H_2O$). Tissue culture inserts are permeant to all sizes of dextran tested (up to 2.5 MDa; FIG. 20 inset). These results demonstrate that the peptide-stimulated decrease in $R_{TE}$ is paralleled by an increase in concentration-gradient driven transepithelial flux of large, uncharged solutes. The lack of permeation by 77 kDa and larger solutes suggests that the peptide-associated permeation pathway has a finite maximal diameter or that the pathway exhibits some form of selectivity, an observation that is consistent with $I_{sc}$ measurements reported for bi-ionic conditions. The permeation of FITC conjugated dextran across a tissue culture support in the absence of cells occurs at a rate that is approximately 1000 fold higher than in the presence of cells. (FIG. 20 insert).

Parsimony indicates that the dye-labeled dextran molecule passes from one side of the monolayer to the other via a pathway that results from disruption of the cell-cell tight junctions that impart the high resistance barrier. Accordingly, the present invention provides peptides operable for reversibly opening tight junctions. Preferred peptides in this respect include SEQ ID Nos. 9, 18, 19, 26, 27, 54, and 55. Additionally, the present invention provides methods of modulating the tight junctions such that molecules that cannot cross the junction without the treatment are able to cross the junctions after the treatment. It is preferred that the junctions can be opened to permit the crossing thereof by a molecule of any size. Advantageously, the process is reversible through the removal of the causative peptide, including through dilution/washes or complexation with an antibody. Moreover, the peptides of the present invention work at relatively low concentrations ($\approx 30$ µM) relative to other agents such as EDTA which work at concentrations that are at least 100× higher.

Example 10

This example determined the effects of SEQ ID No. 18 on ion transport, MDCK $g_{TE}$, permselectivity of Cl⁻ vs. Na⁺, solute permeation and transepithelial flux of solutes, epithelial cell recovery after peptide exposure, as well as the distribution alteration of tight junction associated proteins after peptide exposure.

Materials and Methods

Peptide synthesis. All peptides were synthesized by solid phase synthesis using 9-Fluorenylmethoxycarbonyl chemistry as described in detail previously. Peptides were purified and characterized by reversed-phase HPLC and matrix-assisted laser desorption time-of-flight mass spectroscopy (MALDI-TOF).

Cell culture. MDCK cells were provided by Dr. Lawrence Sullivan (University of Kansas Medical Center, Kansas City, Kans.) and were maintained in culture as described previously. Briefly, the culture medium was a 1:1 mixture of DMEM and Ham's F-12 (GIBCO BRL, Rockville, Md.) supplemented with 5% heat inactivated fetal bovine serum (FBS, BioWhittaker, Walkersville, Md.), and 1% penicillin and streptomycin (Gibco BRL). Cells were grown in plastic 25 cm² culture flasks (Cellstar, Frickenhouse, GE) in a humidified environment with 5% $CO_2$ at 37° C. Confluent cultures were dissociated for subculture with -phosphate-buffered saline (PBS) containing 2.6 mM EDTA and 0.25% trypsin. For permeation and flux experiments cells were seeded on 1.13 cm² permeable supports (Snapwell, Costar, Cambridge, Mass.) at a density of approximately 1×10⁶ cells/well and incubated in DMEM/F-12 supplemented with FBS and antibiotics (refreshed every other day) for 2-3 weeks prior to being mounted in modified Ussing flux chambers for evaluation.

Electrical measurements. Transepithelial ion transport was evaluated in modified Ussing chambers (Model DCV9; Navicyte, San Diego, Calif.). For typical electrical measurements of ion flux, cells were bathed in symmetrical Ringer solution (composition in mM: 120 NaCl, 25 $NaHCO_3$, 3.3 $KH_2HPO_4$, 0.8 $K_2HPO_4$, 1.2 $MgCl_2$, 1.2 CaCl $_2$; 290±2 mOsmol). The diffusion chambers were maintained at 37° C. and continuously bubbled with 5% CO2/95% $O_2$ to maintain pH, provide aeration and mix the fluid in the chambers. The transepithelial potential ($V_{TE}$) was clamped to zero, and $I_{SC}$ measured continuously with a voltage-clamp apparatus (Model 558C, University of Iowa, Department of Bioengineering, Iowa City, Iowa). Data were acquired at 1 Hz with a Macintosh computer (Apple Computer, Cuppertino, Calif.) using Aqknowledge software (ver. 3.2.6; BIOPAC Systems, Santa Barbara, Calif.) with an MP100A-CE interface. $g_{TE}$ was determined by exposing the epithelia to a 5 second 1 mV bipolar pulse at 100 second intervals. The recorded current deflections were used with Ohms law to calculate $g_{TE}$:

$$g_{TE} = g_{TEo} + \frac{g_{TEmax}}{1 + e^{-\left[\frac{t-t_0}{b}\right]}}$$

Alternative apical bathing solutions that allowed for the imposition of defined transepithelial ion gradients were employed for one set of experiments. Three solutions of virtually identical osmolality (280-290 mOsm) and total electrolyte strength to normal Ringer solution were formulated: nominally Na⁺-free (in mM; 120 N-methyl-D-glucamine {NMDG}-Cl, 25 choline-$HCO_3$, 3.3 $KH_2PO_4$, 0.8 $K_2HPO_4$, 1.2 $CaCl_2$, 1.2 $MgCl_2$), nominally Cl⁻-free (in mM; 120 Nagluconate, 25 $NaHCO_3$, 3.3 $KH_2PO_4$, 1.2 $CaSO_4$, 1.2 $MgSO_4$, 2.8 $CaCl_2$) and nominally NaCl-free (in mM; 120 NMDG-gluconate, 25 choline $HCO_3$, 3.3 $KH_2PO_4$, 0.8 $K_2HPO_4$, 1.2 $CaSO_4$, 1.2 $MgSO_4$, 2.8 $CaCl_2$), was added to the gluconate-containing solutions to maintain the free $Ca^{2+}$ concentration and to insure adequate Cl⁻ for proper electrode function.

Xenopus oocyte isolation. Oocyte isolation was performed as described previously with minor modifications. Briefly, sexually mature, HCG-treated Xenopus laevis were purchased (Xenopus 1, Ann Arbor, Mich.) and individually maintained in aquaria in an AAALAC-accredited facility. Oocyte isolation was accomplished by using IACUC-approved protocols in which Xenopus were anesthetized by exposure to MS-222 (Sigma, St. Louis, Mo.) and a laparoscopic approach was employed to isolate and remove the ovary. Oocytes were separated from follicular cells by incubation in nominally Ca-free ND-96 (in mM: 96 NaCl, 1 KCl, 1 $MgCl_2$, 5 HEPES, pH 7.5) including 0.7 mg/ml collagenase (Gibco BRL) and 0.1 mg/ml trypsin inhibitor (Sigma Chemical Co.) on a low-speed rocker at room temperature for 35-60 min. Oocytes were rinsed fivex and incubated in $K_2HPO_4$, (100 mM; pH 6.5) with BSA (Sigma Chemical Co.; 0.1% w/v for one hour with gentle agitation at 15 minute intervals. Oocytes were then transferred to and maintained in modified Barth's solution (in mM; 88 NaCl, 2.4 $NaHCO_3$ 1 KCl, 0.82 $MgSO_4$, 0.41 $CaCl_2$, 0.3 $Ca(NO_3)_2$, 10 HEPES, pH7.5) at 18-20° C. until current recordings were made 1 to 5 days later.

Membrane conductance and permselectivity. The two-electrode voltage-clamp technique was employed. Oocytes were impaled with two 3-M KCl-filled electrodes having resistances of 0.5-2 MΩ. The electrodes were connected to a GeneClamp 500 current-voltage clamp amplifier (Axon Instruments, Foster City, Calif.) via Ag-AgCl pellet electrodes and referenced to a Ag—AgCl pellet that communicated to the bath via an agarose bridge (3% agarose in 1 M KCl). The voltage clamp was controlled by an analog-digital interface (Digidata 1200b) using a Pentium-based computer running pClamp software (version 9.0, Axon Instruments) for command potential and current and voltage recording. Two voltage-pulse protocols were employed. In the first, membrane potential ($V_m$) was held at −30 mV (approximately the resting $V_m$) and pulsed to 0 mV for 1000 ms.

This pulse protocol was repeated at 4128 ms intervals throughout the experimental period to verify that stable conductance levels were achieved with each change of bath solution. Current-voltage relationships were generated at the end of each treatment period (baseline, peptide-exposed, ion-substituted) with a repeating three-step protocol. $V_m$ was held at −30 mV for 500 ms, pulsed to one of nine voltages (−100 to +60 mV in 20 MV increments) for 1000 ms and returned to −30 mV for 500 ms. The average voltage and current during the final 500 ms of each voltage pulse was used to construct each current-voltage (I-V) relationship.

Data were recorded in solutions of four ionic compositions; ND96 (in mM; 96 NaCl, 1 KCl, 1 MgCl$_2$, 1.8 CaCl$_2$, 5 HEPES), reduced Na$^+$ and Cl$^-$ (in mM; 173 mannitol, 9.6 NaCl, 1 KCl, 1 MgCl$_2$, 1.8 CaCl$_2$, 5 HEPES) reduced Cl$^-$ (in mM; 92.3 Na-gluconate, 3.7 NaCl, 1 KCl, MgCl$_2$, 1.8 CaCl$_2$, 5 HEPES) and reduced Na$^+$ (in mM; 86.4 NMDG-Cl, 9.6 NaCl, 1 KCl, 1 MgCl$_2$, 1.8 CaCl$_2$, 5 HEPES). pH was adjusted to 7.5 for all solutions. The final osmolality of all solutions was between 185 and 200 mOsm. I-V relationships were initially recorded in ND96 in the absence of any synthetic peptide. Peptide (8 µl, 5 mM in H$_2$O) was then added to the 400 µl bath and mixed to attain a final concentration of 100 µM. After attaining stable parameters (<5 min), an I-V was again recorded. Subsequently, the bath composition was changed to an alternative ion composition by adding 200 µl of the new solution, mixing, and removing 200 µl of the bathing medium 15 times (>99.7% bath replacement). Peptide was again added to the bathing medium (100 µM final concentration), and the stability of membrane conductance was verified before recording an I-V relationship. The bathing media was repeatedly changed with this technique. In every case, though, recordings were made in ND96 before (and typically after) recording in an alternative ionic composition to verify reversibility of bath composition-induced changes and to allow for comparisons to temporally close controls. Visual inspection suggested that a linear I-V relationship was present, as expected. Thus linear regression (Sigmaplot v. 2000 for Windows; SPSS, Chicago, Ill. and Excel, v. 9.0.38; Microsoft, Redmond, Wash.) was employed to determine the slope conductance and reversal potential in each condition. I-V relationships were mathematically adjusted for junction potentials by using the appropriate pClamp module. Permselectivity (P) for Cl$^-$ versus Na$^+$ was estimated by using equation 1, which is derived from the Goldman-Hodgkin-Katz constant field equation.

$$P_{Cl} : P_{Na} = \frac{[Cl]_2 - \left(e^{\frac{\Delta V_{rev} F}{RT}} * [Cl]_1\right)}{\left([Na]_2 * e^{\frac{\Delta V_{rev} F}{RT}}\right) - [Na]_1}$$

This analysis is based on changes in reversal potential ($\Delta V_{rev}$) that accompany a change in bath ionic composition with the underlying assumption that, in the presence of peptide, membrane conductance could be attributed to the peptide. The analysis further assumes that, since the concentration of other ions (e.g., K$^+$, Ca$^{2+}$, Mg$^{2+}$) was relatively small and unchanged, overall permeation by these ions would minimally contribute to changes in reversal potential. e, F, R, and T have their conventional definitions. Subscript 1 indicates the ion activity in ND96 while subscript 2 denotes the activity in reduced NaCl ND96.

FITC-dextran permeability assay. Epithelial permeability to uncharged solutes of various sizes was assessed with monolayers grown on Snapwell tissue culture inserts as described above. Confluent monolayers were washed once with Ringer solution and placed in one of three treatments containing FITC-conjugated dextran (Sigma Chemical Co.) in the apical compartment; 1, Ringer solution in the apical and basolateral compartments; 2, Ringer solution apical and basolateral with NC-1059(SEQ ID No. 27) (100 µM) in the apical solution; or 3, EDTA (3 mM) in Ringer solution that had been diluted 1:1 with distilled water in both the apical and basolateral compartments. Monolayers were incubated at 37° C. for 60 minutes and the solution in the basolateral well was sampled to quantify fluorescently labeled dextran. Monolayers were then washed with Ringer solution to remove peptide, EDTA, and dextran, placed in tissue culture medium and returned to the incubator for two days before the assay was conducted again.

Confocal microscopy. Immunoreactivity to antibodies raised against tight-junction associated proteins was assessed by confocal microscopy (Zeiss, Thornwood, N.Y.). Samples for visualization were prepared from monolayers used in electrophysiological studies. After removal from Ussing chambers, monolayers were washed in Ringer solution and fixed overnight in 10% neutral buffered formalin. Monolayers were washed 3 times in PBS, permeabilized with 0.1% Triton X-100 in PBS, blocked with goat serum, and then exposed to primary antibody in a 1:500 dilution (rat anti-ZO-1, cat# MAB120, Chemicon, Temecula, Calif. or rabbit anti-occludin, cat.# 71-1500; Zymed, San Francisco, Calif.) for 1 hour at room temperature. After being washed 3 times in PBS, FITC-conjugated goat anti-rat (cat #AP136F, Chemicon) or goat anti-rabbit (cat #FI-1000; Vector Laboratories, Burlingame, Calif.) secondary antibodies were employed (1:1000 dilution) with exposure occurring for 1 hour at room temperature. TRITC-labeled phalloidin (0.1 mg/ml in methanol; Sigma Chemical Co.) was used for F-actin localization was applied concurrently with the secondary antibody. A KrAr laser was used to excite the fluorophores. Filter sets used for fluorescein were BP485/20 nm for excitation and BP515-540 nm for emission and for rhodamine BP530-585 nm for excitation and LP590 nm for emission.

Chemicals and stock solutions. 1-EBIO (Acros; Fisher Scientific, Pittsburgh, Pa.) was prepared as a 1 M stock solution in dimethyl sulfoxide. Forskolin (*Coleus forskohlii*) was purchased from Calbiochem (La Jolla, Calif.) and prepared as a 10 mM stock in ethanol. All other chemicals were purchased from Sigma Chemical Co. and were of reagent grade unless otherwise noted. Unless otherwise stated, synthetic peptide was suspended in water at 5 mM just before experimental addition.

Data analysis. All results are presented as means±SEM. Fitting of user-defined functions to data sets was conducted with Sigmaplot. The difference between treatment groups was analyzed by using Student's t-test (Microsoft Excel 2002). The probability of making a type I error <0.05 is considered statistically significant. The reported value of N is the number of independent observations.

Results and Discussion

Figure 21:
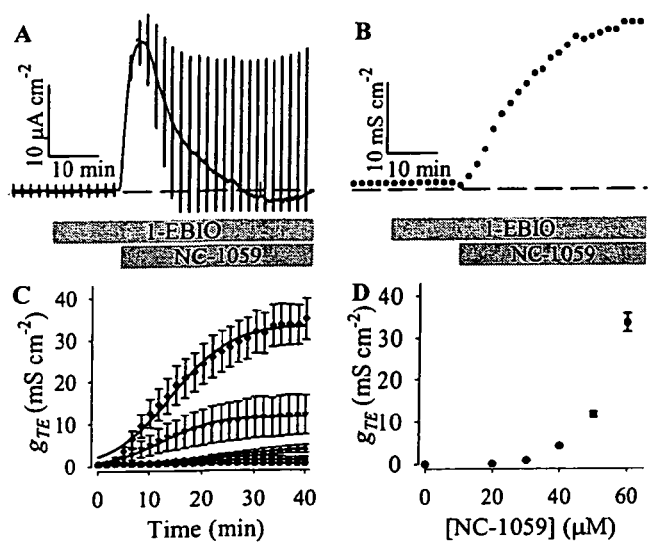
FIG. 21 is a set of four graphs illustrating the modulation of epithelial permeability by EBIO (21A and 21B) and SEQ ID No. 27 (21C and 21D)

SEQ ID NO. 27 mediates ion transport in a concentration-dependent manner. NC-1059 (SEQ ID No. 27) causes a concentration-dependent increase in I$_{SC}$ (indicative of anion secretion or cation absorption) and g$_{TE}$ across MDCK epithelial monolayers. Thus experiments have been conducted to determine if the concentration-dependency is similar for these two outcomes. Epithelia were pretreated with 1-EBIO to fully activate basolateral potassium channels in all preparations and thus maximize the electrochemical driving force for ion transport. As previously reported, 1-EBIO has no effect on either I$_{SC}$ or g$_{TE}$, suggesting that under basal conditions, the basolateral membrane of MDCK cells is not rate limiting for anion secretion nor is it the primary determinant of transepithelial resistance (FIGS. 21A and B wherein dashed lines represent either zero current or zero conductance). Apical exposure to SEQ ID NO. 27 (100 µM) results in a rapid increase in I$_{SC}$ that reaches a peak value before declining toward zero (FIG. 21A) with corresponding changes in g$_{TE}$ (FIG. 21B). Basal g$_{TE}$ is low (<1 mS/cm$^{-2}$), and exposure to SEQ ID NO. 27 results in an increase in $g_{TE}$ with a slower onset of effect than the increase in $I_{SC}$. These results suggest that the conductive pathway that accounts for ion transport does not directly or fully account for the increase in $g_{TE}$. However, the increase in $g_{TE}$ may contribute to the return of $I_{SC}$ toward zero by depolarization of the epithelial cells that reduces secondary active ion flux. There is also the possibility that, at extremely high $g_{TE}$, any electrode offset or junction potential could affect $I_{SC}$. Data similar to that presented in FIG. 21A, in which the change in $I_{SC}$ is plotted as a function of peptide concentration have been reported previously. The fit of a modified Hill equation to the data revealed a value for $K_{1/2}$ (50 µM) that is four-fold lower than that reported for similar peptides (e.g., $NK_4$-M2GlyR, 208±6 µM), although the predicted value for $I_{MAX}$ (25.0 µA cm$^{-2}$) is indistinguishable (24.3±0.5). These results show that SEQ ID NO. 27 exhibits greater biological availability or efficacy than $NK_4$-M2GlyR while maintaining channel-forming ability, a stated goal for the design of a CF therapeutic. Additionally, substantial increases in $g_{TE}$ are observed. Whereas the latter effect is not a targeted outcome, it is immediately obvious that SEQ ID NO. 27 provides unique research and therapeutic opportunities. Characterization of this effect provides the basis for the remainder of this report.

SEQ ID NO. 27 causes concentration-dependent increase in MDCK $g_{TE}$. Experiments have been conducted to determine the concentration-dependence and time-course of SEQ ID NO. 27-induced changes in $g_{TE}$. Data from FIG. 21B and 3-10 additional experiments at each concentration are summarized in FIGS. 21C and 21D. FIG. 21C illustrates the time dependent increase in conductance across MDCK monolayers at increasing concentrations of SEQ ID No. 27 (20 µM (■), 30 µM (●), 40 µM (▲), 50 µM (▼), 60 µM (♦)). Data points represent the mean+/−SEM for 5-15 observations. The solid lines represent the best fit of equation 2 to each data set. Results clearly show that $g_{TE}$ increases to a plateau value over the duration examined and that the peptide-induced increase in $g_{TE}$ is concentration-dependent. To predict the maximal change in $g_{TE}$ and the time course of this change, data in FIG. 21D are fitted by a logistic equation. In FIG. 21D, the derived maximal change in transepithelial conductance is plotted as a function of peptide concentration. Again, the data points represent the mean+/−SEM derived by the fit of equation 2 to each data set.

$$g_{TE} = g_{TEo} + \frac{g_{TEmax}}{1+e^{-\left[\frac{t-t_0}{b}\right]}}$$

$g_{TEO}$ is the initial $g_{TE}$ while $g_{TEmax}$ represents the maximal change in $g_{TE}$. $t_0$ represents the time to reach $g_{TEmax}/2$ and b is inversely proportional to the rate of rise at $t_0$. For the analysis, $g_{TEO}$ was constrained to be positive, as negative numbers are, in this case, non-sensical. Derived values of $t_0$ varied over a narrow range (12.4±1.5 minutes at 60 µM to 15.3±0.6 minutes at 30 µM) with no distinct concentration-dependence being observed. The rate of increase in $g_{TE}$ (b) exhibits concentration dependence with a maximal rate derived for exposure to 60 µM SEQ ID NO. 27 (5.1±0.6 min)$^{-1}$. Likewise, the $g_{TEmax}$ was also concentration-dependent with a maximum value of 33.5±2.2 mS cm$^{-2}$, which is approaching a practical limit for the assay system in that this conductance is one third to one half the electrical conductance of a culture insert in the absence of cells (70-100 mS cm$^{-2}$). Values of $g_{TEmax}$ derived from the mathematical fits to the data are plotted as a function of peptide concentration in FIG. 21D. No indication of saturation is observed over the concentration range that could be tested. Whether a maximal $g_{TE}$ is reached cannot be effectively determined since the observed conductance with 60 µM is approaching the maximal observable conductance for the recording system.

Figure 22:
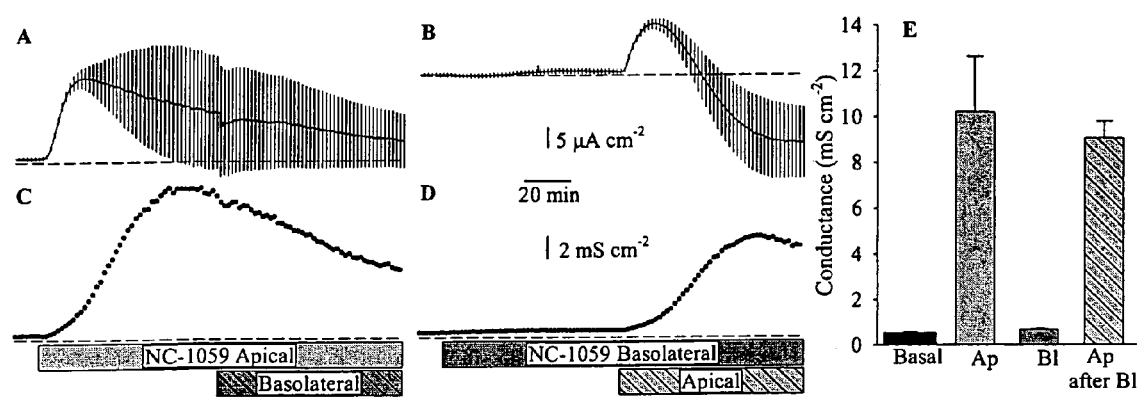
FIG. 22 is a set of five graphs illustrating the relative efficacy of apical and basolateral changes in ion transport and barrier function after exposure to SEQ ID No. 27.

SEQ ID NO. 27-induced changes in $g_{TE}$ require apical exposure. Experiments were conducted to test for the relative efficacy of apical and basolateral SEQ ID NO. 27 on changes in ion transport and barrier function. Results presented in FIG. 22 demonstrate that apical exposure is required to observe a significant effect of the peptide on these parameters. Results from a typical experiment are presented in FIGS. 22A-D. In each of these graphs, dash lines represent either zero current or zero conductance. When apically exposed to SEQ ID NO. 27 (300 µM), $I_{SC}$ rapidly increases to a peak value and then declines (panels A and B) whereas the increase in $g_{TE}$ is delayed (panels C and D; Consistent with FIG. 21). Exposure of the basolateral membrane to SEQ ID NO. 27 produces no obvious effect, regardless of the order of exposure. Results from these and five additional monolayer pairs are summarized in FIG. 22E. On a pairwise basis, effects were never observed with basolateral exposure and were always observed with apical exposure. These results might suggest that SEQ ID NO. 27 interacts with a cellular component that is accessible only from the apical aspect of the monolayer although additional experiments are required to fully test this hypothesis.

Figure 23:
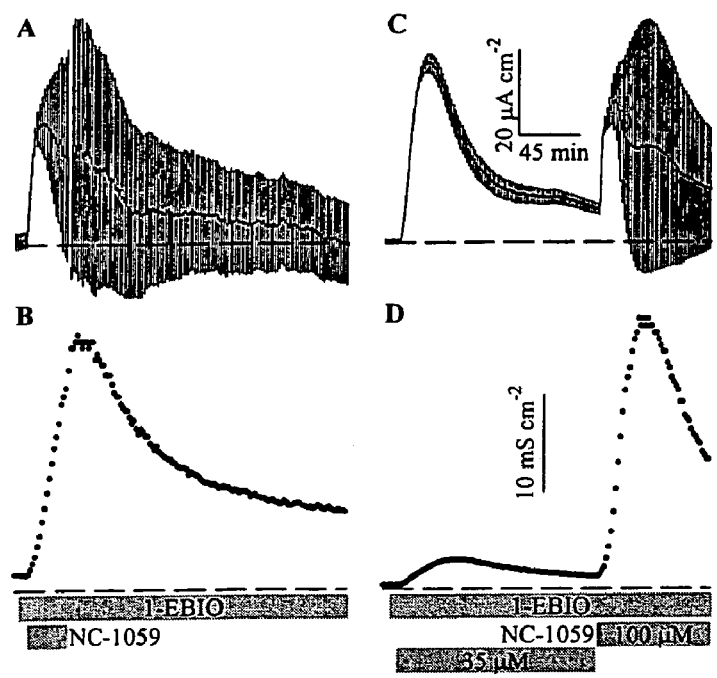
FIG. 23 is a set of four graphs illustrating peptide effects of $I_{sc}$ and $g_{TE}$ on epithelial cells.

SEQ ID NO. 27-induced changes in $g_{TE}$ are readily reversible. Data presented in FIG. 23 show that the peptide-induced increase in $I_{SC}$ and $g_{TE}$ can reverse over time either with or without washout of the peptide. In the presence of 1-EBIO, 60 µM SEQ ID NO. 27 causes a typical rise in $I_{SC}$ (FIG. 23A) and $g_{TE}$ (FIG. 23B). In FIG. 23A, an MDCK monolayer was exposed to SEQ ID NO. 27 (60 µM) for 30 minutes. Following 30 minutes of exposure, the solution bathing the apical aspect of the epithelium was replaced with peptide-free Ringer solution and recording continued for 5 hours. Results show that the $I_{SC}$ and $g_{TE}$ return toward, but do not return to pretreatment values during the duration of the recording. In this paradigm, monolayers respond to the subsequent addition of forskolin with an increase in $I_{SC}$ (data not shown), demonstrating that epithelia remain viable and responsive to cAMP-mediated stimulation following peptide exposure. FIG. 23B provides $g_{TE}$ for all time points represented in FIG. 23A.

A separate MDCK monolayer was sequentially exposed to two concentrations of SEQ ID NO. 27 (35 and 100 µM) with the recorded $I_{SC}$ and derived $g_{TE}$ presented in FIGS. 23C and 23D, respectively. In FIG. 23C, a separate MDCK monolayer was exposed to 35 µM of SEQ ID NO. 27 with no replacement of the apical solution. FIG. 23D provides the $g_{TE}$ for all time points represented in FIG. 23C. The results are typical of 3-6 separate experiments and dashed lines represent either zero current or zero conductance. Results clearly show that a sub-maximal increase in $g_{TE}$ is achieved and maintained for over 3 hrs in the presence of 35 µM SEQ ID NO. 27. Such prolonged exposure is apparently without deleterious effects on the epithelium since no evidence of epithelial deterioration is observed and responsiveness is maintained. Subsequent exposure to greater concentrations of SEQ ID NO. 27 (100 µM final) further increases $g_{TE}$ and $I_{SC}$ to a value expected for this concentration (17 mS cm$^{-2}$ and 32 µA cm$^{-2}$). It should be noted that, regardless of whether the peptide is removed from the bath, some reversal in both $I_{SC}$ and $g_{TE}$ is observed.

Figure 24:
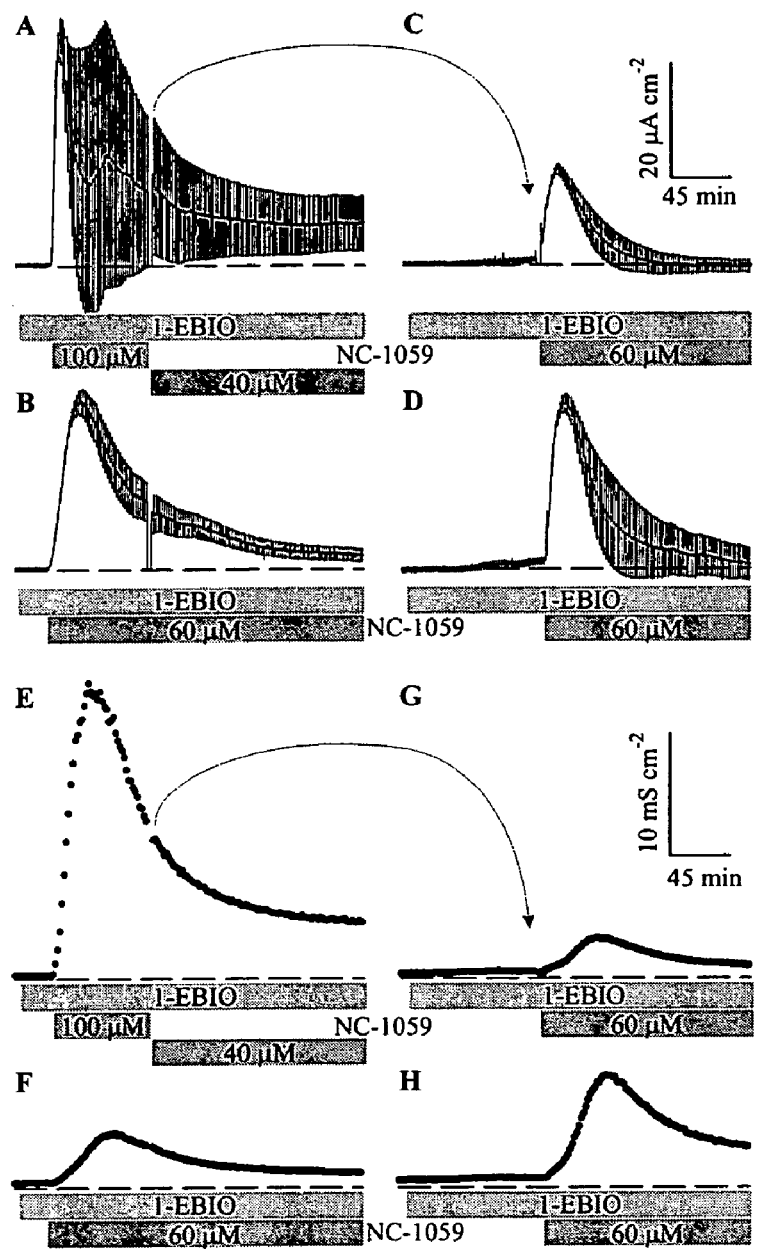
FIG. 24 is a set of eight graphs illustrating the activity of SEQ ID No. 27 on epithelial cell monolayers over time.

Experiments designed to determine whether the SEQ ID NO. 27 activity in solution declines over time were conducted although it was previously reported that SEQ ID NO. 27 does not aggregate in solution, as was seen with related peptides. Results from a typical experiment are presented in FIG. 24. Paired monolayers were mounted in Ussing chambers with some being immediately exposed to SEQ ID NO. 27. Sixty and 100 µM SEQ ID NO. 27 elicited expected increases in $I_{SC}$ and $g_{TE}$ that reversed over time. Sixty percent of the apical solution was then transferred from the apical side of a treated monolayer to an untreated monolayer as indicated by the arrow (FIGS. 24A to C; E to G). The arrow is an indicator that apical solution containing peptide had been in contact with an epithelial monolayer for greater than 75 minutes (FIGS. 24A and E) and replaced with an equal volume of apical solution. A previously untreated monolayer was exposed to 60 µM of freshly dissolved SEQ ID NO. 27 at the same time (FIGS. 24D & H). The results clearly demonstrate that active SEQ ID NO. 27 continued to be present in the apical solution even as the effect on $I_{SC}$ and $g_{TE}$ were reversing. The possibility remained that peptide activity was slowly decreasing such that the response declined incrementally as activity diminished. This possibility was excluded by experiments in which a peptide-induced response was generated and apical solution was partially replaced with Ringer solution containing freshly dissolved peptide. No increment in either $I_{SC}$ or $g_{TE}$ was observed (N=3). Taken together, these results suggest that the effect of SEQ ID NO. 27 on MDCK electrical parameters is transient.

Figure 25:
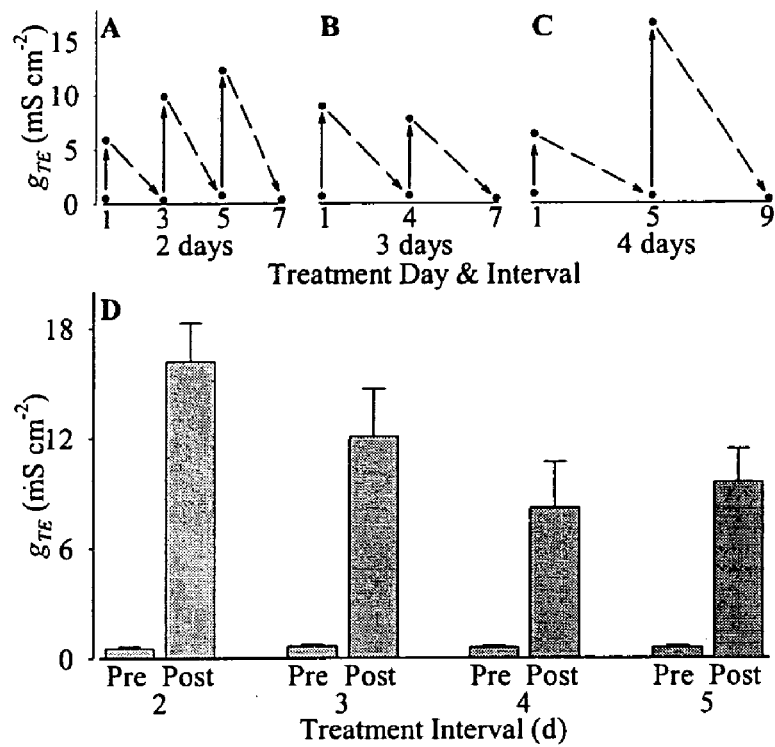
FIG. 25 is a set of four graphs illustrating the reversibility of peptide-induced changes in cell monolayers.

Additional experiments have been conducted to test for complete reversibility of peptide-induced changes in $g_{TE}$. Monolayers were exposed to peptide (60 µM) in an Ussing chamber for ~20 minutes to document increases in $g_{TE}$, recovered and returned to the cell culture incubator for two to five days with the apical and basolateral media refreshed daily before subsequent assessment of basal $g_{TE}$ and responsiveness to peptide. Results presented in FIGS. 25A-C show the time course of changes in $g_{TE}$ for three typical monolayers that were repeatedly exposed to SEQ ID NO. 27 at 2-, 3-, and 4-day intervals, respectively. Solid arrows indicate the effect of SEQ ID NO. 27 while the dashed arrows indicate the return to pretreatment values that are observed prior to a subsequent exposure. Solid circles represent derived values for $g_{TE}$. In all cases $g_{TE}$ is less than 2 mS cm$^{-2}$ at baseline, increases to greater than 15 mS cm$^{-2}$ with peptide exposure, and returns to less then 2 mS cm$^{-2}$ before the subsequent assessment. Regardless of the duration between peptide exposures (2, 3, or 4 days), $g_{TE}$ of previously treated monolayers returns to pretreatment values and is indistinguishable from that of untreated monolayers (not shown). Some monolayers have been exposed to peptide as many as 8 times over a sixteen-day period with no change in pretreatment $g_{TE}$ and no diminution of responsiveness. Data from 4 to 8 monolayers at each time point are summarized in FIG. 25D. Results demonstrate that $g_{TE}$ after as little as two days incubation in peptide-free media is indistinguishable from untreated monolayers (0.6±0.1 versus 0.5±0.1 mS cm$^{-2}$, respectively). Neither the pretreatment $g_{TE}$ nor the post-treatment $g_{TE}$ differs (P>0.2) between monolayers that are incubated for 2, 3, 4, or 5 days following peptide exposure. Taken together, results presented in FIGS. 23, 24 and 25 demonstrate that SEQ ID NO. 27-induced changes in $g_{TE}$ are fully reversible and that the responses are readily repeatable.

Figure 26:
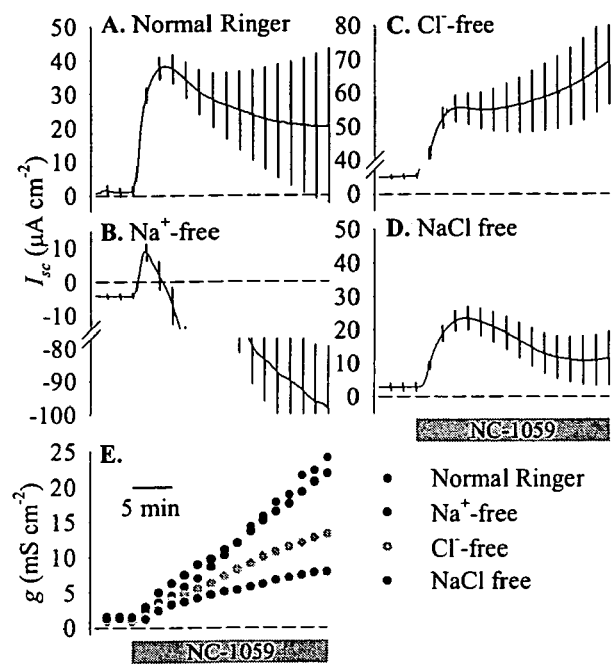
FIG. 26 is a set of five graphs illustrating the effects of changing the primary anion and/or cation is the solution bathing epithelial cells.

SEQ ID NO. 27-induced changes in $g_{TE}$ occur in the absence of small monovalent ions. Experiments have been conducted to test for effects of changing the primary anion and/or cation in the solution bathing the apical aspect of the epithelium. Substitution of apical Na$^+$ with NMDG$^+$, a cation that fails to permeate most Na$^+$ and/or K$^+$-selective channels, alters the kinetic profile for SEQ ID NO. 27-induced effects (FIG. 26B) when compared to a paired control (FIG. 26A). Exposure to SEQ ID NO. 27 was associated with a rapid increase in $I_{SC}$ that reached a maxima in less than two minutes (i.e., more rapidly than in control conditions), and then reversed polarity to achieve strong negative $I_{SC}$ (note that there is a break in the ordinate) for the duration of the experiment. Likewise, substitution of Cl$^-$ by gluconate is associated with quantitative and qualitative differences in the SEQ ID NO. 27 response profile (FIG. 26C). SEQ ID NO. 27 causes a substantially larger increase in $I_{SC}$ than in control conditions, and the elevated $I_{SC}$ is maintained for the duration of the experiment. Finally, substitution of both N$^+$ and Cl$^-$ provides a response profile that more closely approximates the control conditions (FIG. 26D). Regardless of the ions present in the apical solution, similar profiles for the increase in $g_{TE}$ are observed (FIG. 26E). Taken together, the results are consistent with SEQ ID NO. 27 being a non-selective or modestly anion-selective channel at the apical membrane that subsequently induces the operation of a pathway that allows for selective permeation by Na$^+$ and Cl$^-$ relative to NMDG$^+$ and gluconate, respectively. These conclusions are based on the observations that, in the absence of apical Na$^+$ and with no anion gradient, one might expect Na$^+$ secretion through a non-selective ion channel. Such activity would result in a negative $I_{SC}$. However, $I_{SC}$ initially increases in response to SEQ ID NO. 27, which is consistent with anion secretion, but not cation secretion. Subsequently, $I_{SC}$ becomes negative, consistent with gradient-driven Na$^+$ secretion through a pathway that is selective for Na$^+$ over NMDG$^+$. In this condition, any ongoing anion secretion would reduce the $I_{SC}$ magnitude. In the absence of apical Cl$^-$, the acute effect of SEQ ID NO. 27 on $I_{SC}$ is enhanced as would be expected for an increased electrochemical driving force for anion secretion. $I_{SC}$ reaches a transient plateau and then continues to increase. A sustained elevation in $I_{SC}$ that is consistent with ongoing anion secretion (likely both gradient driven and active transport) is observed throughout the experiment. Finally, in the absence of both Na$^+$ and Cl$^-$ in the apical solution (where similar gradient driven forces for Na$^+$ and Cl$^-$ secretion would be present), the response profile is similar to the control conditions where concentration gradients are not present. $g_{TE}$ does not increase to the same magnitude in Cl$^-$-free conditions, an outcome that would be expected if a portion of the conductance change depends upon permeation through Cl$^-$-selective channels. Taken together, the results suggest that the initial increase in $I_{SC}$ reflects anion (i.e., Cl$^-$) secretion whereas extended effects exhibit little selectivity between Cl$^-$ and Na$^+$ although larger anions (e.g., gluconate) and cations (e.g., NMDG$^+$) are less permeant through this pathway.

Figure 27:
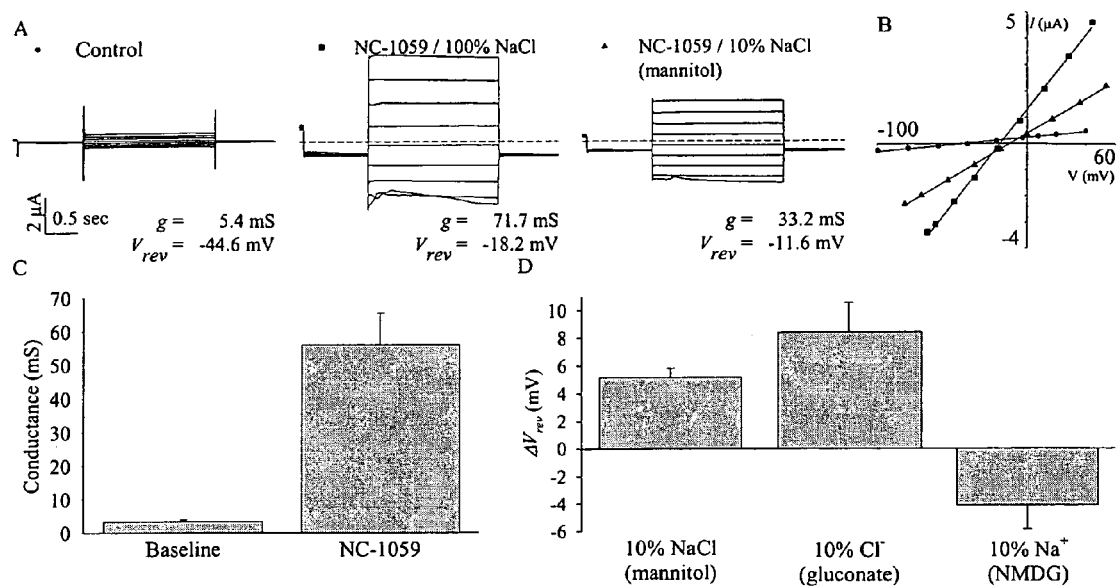
FIG. 27 is a set of four graphs illustrating the permselectivity of SEQ ID No. 27 ion channels in the absence of confounding effects associated with permeation through a non-cellular pathway and the inability to set the electrochemical driving force.

SEQ ID NO. 27 is modestly Cl$^-$ permselective. *Xenopus* oocytes have been employed to further test for permselectivity of SEQ ID NO. 27 ion channels in the absence of confounding effects associated with permeation through a non-cellular (i.e., paracellular) pathway and the inability to set the electrochemical driving force. Typical results showing the SEQ ID NO. 27-induced increase in membrane g and ion-dependent change in $V_{rev}$ are presented in FIGS. 27A and B with results from numerous experiments being summarized in FIGS. 27C and D. The results indicate that exposure to SEQ ID NO. 27 is associated with a >18±4 fold increase in membrane g (n=6). Concomitant reduction in bath Na$^+$ and Cl$^-$ is associated with a rightward shift in $V_{rev}$ of 5.2±0.6 mV. Substitution of Cl$^-$ by gluconate is associated with a greater rightward shift (8.4±2.1 mV), whereas substitution of Na$^+$ by NMDG$^+$ is associated with a 4.2±1.7 mV leftward shift. A synthetic peptide of similar amino acid composition, but in random order has no effect on membrane conductance. In FIG. 23B, the current-voltage (I-V) relationships for the three conditions depicted in FIG. 23A are illustrated. Solid lines represent the least-squares fit of linear function to the data sets from which slope conductance (g) and reversal potential ($V_{rev}$) are derived. Changes in bath ion composition have little effect on membrane conductance or on $V_{rev}$ in the absence of SEQ ID NO. 27 (not shown). Taken together, these results indicate that the SEQ ID NO. 27-induced conductance have a finite permeability for both Cl⁻ and Na⁺. There is, however, little permselectivity between these monovalent ions. Mathematical analysis employing Eqn. 1 indicates a Cl⁻ to Na⁺ permselectivity of 1.29±0.04. Experiments in which these small monovalent ions are singly substituted support this conclusion in that a greater rightward shift in $V_{rev}$ is observed with Cl⁻ substitution than the leftward shift observed with Na⁺ substitution. FIG. 27C provides a summary from 6 Oocytes of derived slope conductances in the absence of and in the presence of SEQ ID NO. 27 (100 µM) in typical Na⁺ and Cl⁻ concentrations. FIG. 23D summarizes the results from 5 Oocytes and the changes in $V_{rev}$ associated with concomitant reduction in Na⁺ and Cl⁻, reduced Cl⁻, and reduced Na⁺. Positive values indicate a rightward shift in $V_{rev}$. Changes in $V_{rev}$ are consistent with the following selectivities: Cl⁻>Na⁺, Cl⁻>gluconate and Na⁺>NMDG. Oocyte results support observation made with intact monolayers by functionally demonstrating the membrane insertion of a permeation pathway that is modestly selective for Cl⁻ over Na⁺. Results from this assay do not, however, address the possibility that a paracellular pathway might be directly or indirectly affected by peptide exposure.

Figure 28:
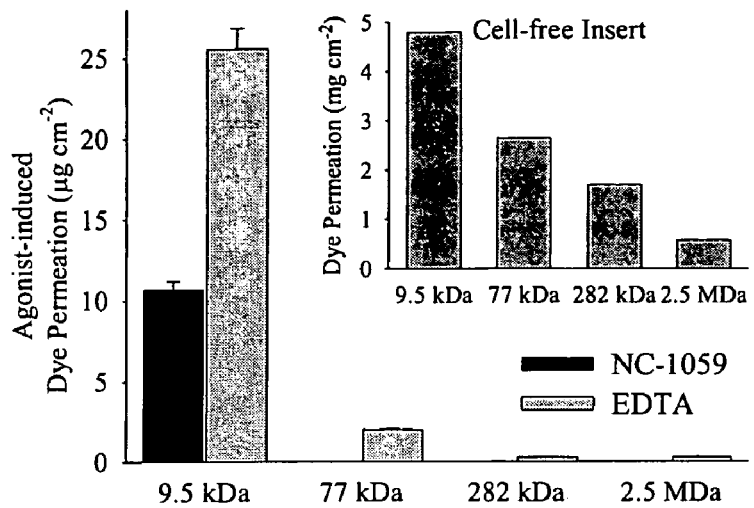
FIG. 28 is a graph and insert illustrating the modulation of permeability to solutes after epithelial exposure to SEQ ID No. 27.
Figure 31:
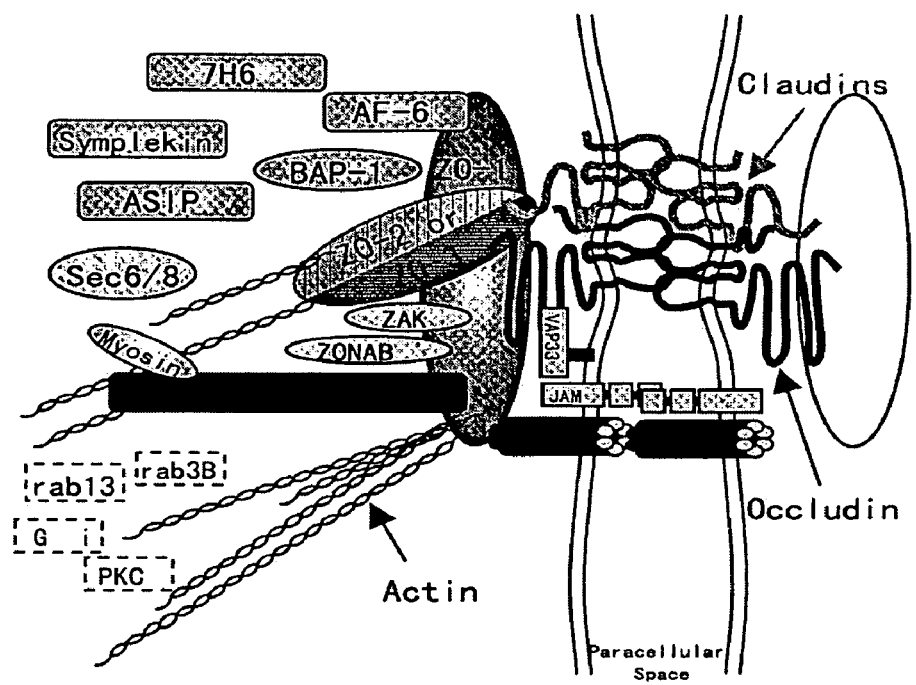
FIG. 31 is an illustration of the proteins implicated in the structure and regulation of tight junctions.

SEQ ID NO. 27 allows permeation of 9.5 kDa FITC-dextran conjugate. Experiments have been conducted to determine if SEQ ID NO. 27-induced changes in $g_{TE}$ are mirrored by changes in permeation of larger, non-ionic solutes. As shown in FIG. 28, SEQ ID NO. 27 exposure caused a substantial increment in transepithelial flux of FITC-labeled 9.5 kDa dextran over a 60 minute assay period, although less than half that observed across paired monolayers exposed to 3 mM EDTA in hypotonic Ringer solution (50% dilution with H₂O). Tissue culture inserts are permeant to all sizes of dextran tested (up to 2.5 MDa; FIG. 31 inset). These results demonstrate that the SEQ ID NO. 27-stimulated increase in $g_{TE}$ is paralleled by an increase in concentration-gradient driven transepithelial flux of large, uncharged solutes. The lack of permeation by 77 kDa and larger solutes suggests that the SEQ ID NO. 27-associated permeation pathway has a finite maximal diameter or that the pathway exhibits some form of selectivity, an observation that is consistent with $I_{SC}$ measurements reported above for bi-ionic conditions.

Figure 29:
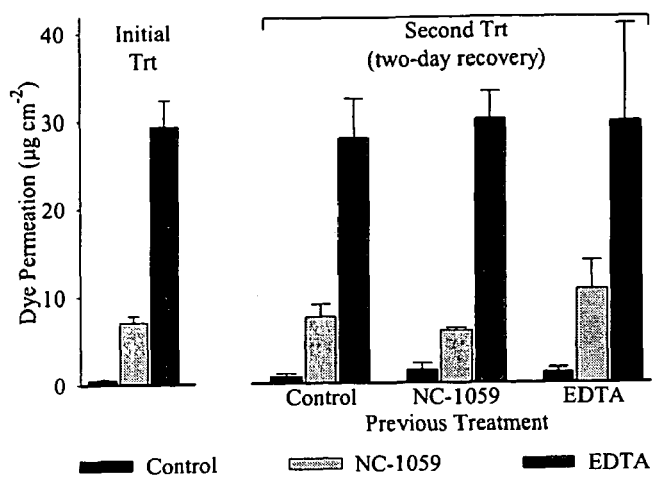
FIG. 29 is a graph illustrating the results from testing to determine if the permeability modulation induced by epithelial cell exposure to SEQ ID No. 27 was reversible.

SEQ ID NO. 27 treated monolayers are transiently permeant to 20 kDa dextran. Experiments have been conducted to determine if, like changes in $g_{TE}$, the SEQ ID NO. 27-induced increase in permeability to 20 kDa dextran is both reversible and repeatable. Results presented in FIG. 29 verify earlier observations by showing that the two treatments, SEQ ID NO. 27 and EDTA/hypotonic Ringer solution are associated with elevated permeation of 20 kDa FITC-dextran conjugate (compare results of initial treatment). All monolayers were washed after assessing the response and returned to the incubator in typical media for subsequent experiments two days later. Monolayers from each of the three initial treatments were divided and exposed in parallel to each of the three treatments. Results demonstrate that, regardless of initial treatment and the magnitude of dye permeation, two days of recovery allow for the reformation of tight epithelial barrier. In each case, when monolayers were exposed to control conditions a minimal amount of dextran permeation is observed indicating that dextran permeability returns to a value that is indistinguishable from untreated monolayers within two days. Furthermore, the results demonstrate that the results of the three treatments are not affected by previous exposure to either SEQ ID NO. 27 or to EDTA. In each treatment group, EDTA exposure was associated with the highest level of permeation. Permeation in the presence of SEQ ID NO. 27 is significantly greater that control, but less than EDTA in each treatment group. The results show that apical SEQ ID NO. 27 exposure of MDCK monolayers causes a transient increase in permeability to uncharged solutes of up to 20 kDa with no long-term deficit in the epithelial barrier function being observed.

Figure 30:
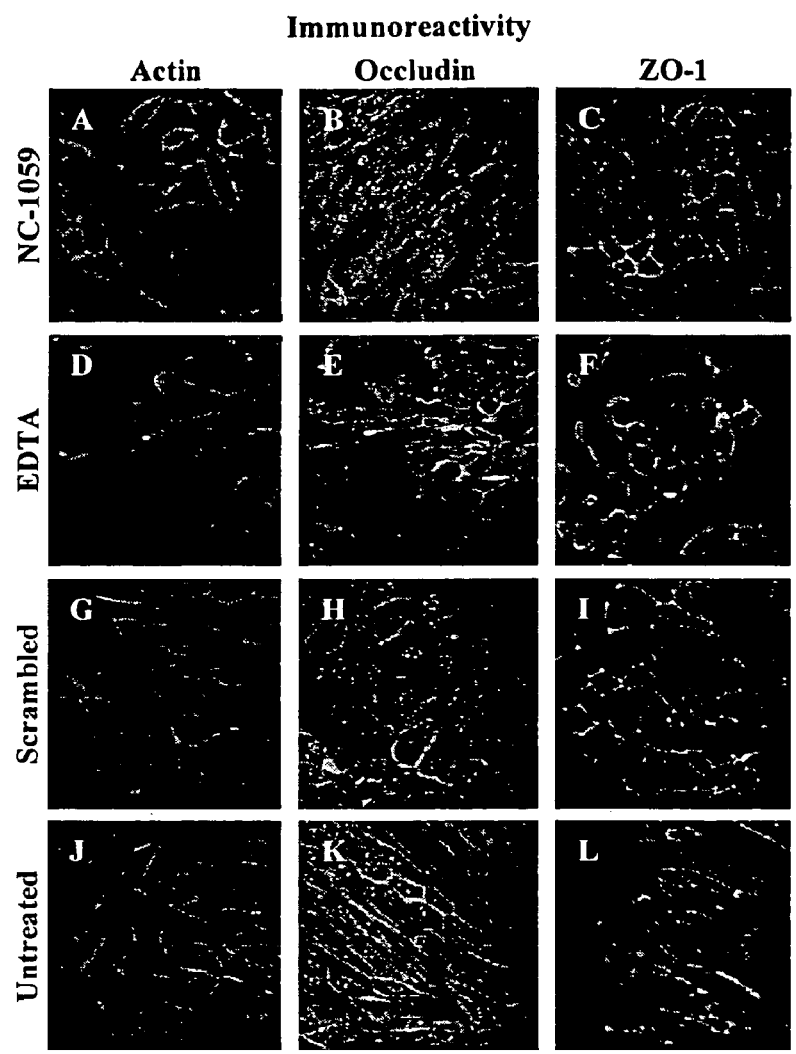
FIG. 30 is a set of photographs illustrating indirect immunofluorescence of tight junction proteins following exposure to SEQ ID No. 27, EDTA, and scrambled peptide of similar composition to SEQ ID No. 27.

Distribution of tight-junction associated proteins is unaltered by exposure to SEQ ID NO. 27. Data presented in FIG. 30 show the immuno-localization of tight junction-associated proteins using confocal microscopy. Protein components of the tight junction selected for analysis were actin, a cytoskeletal component that forms the junction-associated actomyosin ring, ZO-1, a putative scaffold protein that anchors the junctional complex to the cytoskeleton and occludin, a transmembrane protein involved in tight junction formation. When compared to untreated controls, the distribution of actin, occludin and Zo-1 immunoreactivity in MDCK monolayers was unchanged by exposure to SEQ ID NO. 27 (100 µM). Dense immunoreactivity for each tight junction constituent is observed to circumscribe all epithelial cells when viewed on fos. Additionally, punctate intracellular occludin immunoreactivity is observed at the same focal plane and diffuse ZO-1 immunoreactivity that appears to be associated with the nucleus is observed. Alternatively, exposure of epithelial cell monolayers to 6 mM EDTA and hypotonic Ringer solution, a solution commonly employed to reduce junctional integrity and to disrupt cells from culture substrates, is associated with profound changes in localization of the perijunctional actin ring, as well as the distribution of ZO-1. EDTA-treated cells appear to have 'rounded up' and vacant areas in the field suggest that some cell sloughing occurs with this treatment[1]. ZO-1 immunoreactivity remains largely associated with the cell membrane, but appears to be somewhat more diffuse than peptide-treated or untreated controls. Protein distribution in monolayers exposed to a non-channel forming peptide (100 µM) (scrambled) of similar amino acid composition to SEQ ID NO. 27 is indistinguishable from that observed in vehicle-treated control monolayers with cell-to-cell contacts apparently being maintained. In each of these drafts, the scale bar is equal to 25 µM. These results suggest that the SEQ ID NO. 27-associated change in $g_{TE}$ results from tightly controlled changes in the paracellular pathway since large, uncharged solutes can readily permeate the epithelium without any apparent change in the distribution of tight junction-associated proteins or any indication of cell sloughing.

SEQ ID NO. 27 was synthesized as part of an ongoing program to develop synthetic peptides that form anion selective channels in epithelial monolayers as potential therapeutics for CF. The rationale for the synthesis of this peptide was to determine if separate domains contribute to aggregation in aqueous solution and assembly of the peptide in cell membranes. This peptide is remarkable in that it remains monomeric in aqueous solution, yet partitions into cell membranes and supports ion transport across the cell membrane, and thus across epithelial cell monolayers. SEQ ID NO. 27 acts to increase the $I_{SC}$ across MDCK monolayers, with a $k_{1/2}$ of ~40 µM, which is 4-fold less than that of NK₄-M2GlyR, a sequence from which it was developed. Observations made during these experiments initially suggested that SEQ ID NO.

27 also modulates epithelial tight junctions. While not a target of the design process, this effect holds great therapeutic and research potential.

SEQ ID NO. 27 induces a concentration-dependant increase in $I_{SC}$ across epithelial cell monolayers with a con-current increase in $g_{TE}$. This peptide is the only sequence designed so far that has demonstrated the ability to increase $g_{TE}$ to this magnitude, which is in excess of conductance changes expected for apical channel formation as related peptide sequences provide a comparable increases in $I_{SC}$, but do not exhibit the dramatic effects on transmural conductance. This additional functionality suggest that the ability of the peptide to support anion secretion is separate from, but perhaps related to, the effect on $g_{TE}$.

The mechanism by which v modulates $g_{TE}$ is unclear. The simplest interpretation, that SEQ ID NO. 27 forms conductive pores in the apical membrane that fully account for the change in $g_{TE}$, is inadequate. Similar peptide sequences (i.e. with the first 16 amino acid residues identical) cause an equal increase in Isc across MDCK epithelial monolayers, but do not affect transepithelial resistance to the same extent. Comparison of the data presented in FIG. 21D to an earlier report shows that the concentration-dependence for changes in $g_{TE}$ is right-shifted compared to the concentration-dependence of $I_{SC}$. Additionally, permeation of 20 kDa dextran across the epithelium strongly suggests that a paracellular rather than a transcellular route is involved. A second simple possibility that can be discounted is that SEQ ID NO. 27 is cytotoxic and that a loss of cells accounts for the change in $g_{TE}$. Visual inspection provides no indication that cells are absent from the epithelium following SEQ ID NO. 27 exposure, as they are following EDTA exposure. Furthermore, tight junction proteins are not redistributed in response to SEQ ID NO. 27 and both the selectivity ($Na^+>NMDG^+$; $Cl^->$gluconate) and the finite size of the permeation pathway (20, but not 77 kDa dextran) suggests that a selective paracellular pathway is opened. Rather, the results suggest a specific interaction of SEQ ID NO. 27 with the cellular components involved in modulating $g_{TE}$. This conclusion is bolstered by the 'sided-ness' of effects in that changes in electrical parameters are observed only with apical exposure. There is clearly precedence for metabotropic receptors selectively modulating the size exclusion of the paracellular pathway although evidence has not yet been acquired to suggest a metabotropic effect of SEQ ID NO. 27.

That SEQ ID NO. 27 is effective only from the apical aspect of the epithelium suggests that a 'receptor-type' mechanisms might be involved. There is at this time, however, no definitive evidence to support such a claim. Results presented in FIG. 22 might indicate that there is limited access of the peptide across the tissue culture support. However, the membrane was permeable to 2.5 MDa and 77 kD dextran permeated the membrane in the presence of cells following EGTA exposure. Thus, size exclusion by the culture support is unlikely. An alternative to the 'receptor' hypothesis is that the apical membrane exhibits a unique lipid milieu with which SEQ ID NO. 27 interacts. This possibility by necessity includes the supposition that a similar milieu must be present in *Xenopus* oocytes since SEQ ID NO. 27 was quite effectively modulated membrane conductance in this system. A third possibility is that SEQ ID NO. 27 exhibits pleiotropic effects by interacting at multiple cellular sites. At this time it remains unclear if channel formation (i.e., ion transport) is a prerequisite for modulation of $g_{TE}$. The possibility exists that SEQ ID NO. 27 may interact with the apical membrane to form ion channels by mechanisms similar to those that have been indicated for closely related peptides and that effects on $g_{TE}$ require interaction with another epithelial target. Experiments are ongoing to test these possibilities.

The SEQ ID NO. 27-induced change in $g_{TE}$ is transient in nature, reaching a peak value within the first 10-30 minutes of exposure. Several events might account for the transient nature of the response. It is possible that, due to charge neutralization or shielding, the peptide may undergo some aggregation and/or precipitation in Ringer solution, thus reducing the effective concentration. It was previously reported that SEQ ID NO. 27 (initially termed $NK_4$-A'la') does not aggregate in solution. However, the analysis was conducted using $H_2O$ as the solvent instead of Ringer solution. The ionic strength of the Ringer solution may promote peptide aggregation (a competing and irreversible reaction) that would tend to decrease the effective concentration of SEQ ID NO. 27 in the bath and in the cell membrane. Alternatively, the response may diminish due to protease degradation of the peptide, due to uptake of peptide from the apical membrane that subsequently leads to proteolysis. Data presented in FIG. 24 suggest that peptide aggregation or inactivation cannot account for the transient nature of the effects. The possibility remains that there may be some down-regulation of the metabolic process that modulates junction integrity. Data presented in FIG. 23 argue against this latter possibility in that the response to a submaximal concentration remains above baseline for at least two hours and the epithelium subsequently responds to a higher concentration of (SEQ ID NO. 27). Nonetheless, these and other possibilities may in part account for the transient nature of the response; additional experiments must be conducted to more fully evaluate these hypotheses.

There are numerous clinical situations in which modulation of an epithelial barrier presents therapeutic benefits. Drug absorption across intestinal, airway or dermal epithelium could be enhanced with transient decreases in barrier function, making oral, inhaler, or topical administration of what we are now parenteral drugs possible. Oral or inhalant formulations of medications such as insulin would be less expensive to produce and more easily delivered than parenteral formulations. The permeability of the small intestinal epithelium to both insulin and immunoglobulin G was increased in rabbits when co-administered with ZOT. However, ZOT is limited in its therapeutic application as it is only effective in the small intestine. Additionally, ZOT is a 45 kDa protein that must be recombinantly produced and purified although it has been shown that the majority of biological activity can reside in the C-terminus 15 amino acid segment. The M2GlyR-derived peptides are <3 kDa and can be prepared synthetically or recombinately expressed.

Gene therapy for epithelia-associated diseased such as CF provides a second therapeutic setting in which modulation of transepithelial permeability is desirable. Stable transfection of DNA sequences into epithelial cells in culture provides proof that genetic epithelial diseases can be treated or cured. However, bronchiolar epithelial cell viral receptors are located primarily in the basolateral membrane, leading to a low efficiency of gene transfer from apical exposure to viral vectors. Thus, high viral titers and long incubation times are required to increase transfection efficiency, which can lead to a decrease in the effectiveness of repeated treatments. Increased transfection efficiency has been achieved with some chemical modulators of tight junctions (e.g., EGTA, perfluorochemicals, fatty acids), although these treatments were sometimes associated with inflammation. Modulators of epithelial barrier function would be the ideal agents to augment gene therapy, provided that they have a rapid onset, transient duration of action, a favorable safety profile, and do not decrease viral titer. Initial observations with SEQ ID NO. 27 suggest that it may fulfill these criteria although additional experiments are required to determine if viral access is limited due to size exclusion (i.e., <77 kDa). Additional experiments are also required to test for inflammation. In this regard it is encouraging that similar effects on $g_{TE}$ have been observed when all-D amino acid form of SEQ ID NO. 27 was used (unpublished observations).

SEQ ID NO. 27 also presents the potential for developing an increased understanding of physiological and pathophysiological processes that modulate tight junctions. Various epithelia throughout the body exhibit transepithelial electrical resistances that vary over four orders of magnitude, some of which change depending upon the hormonal state (e.g., mammary) or physical environment (e.g., small intestine following a meal). Signaling pathways that affect the paracellular pathway are not fully defined for any epithelium and it is unknown which mechanisms are broadly applicable and which are species- or tissue-specific. In this regard, it is noteworthy that SEQ ID NO. 27 stimulates $g_{TE}$ across male porcine reproductive epithelia, porcine ileal epithelia (IPEC-J2), and human colonic epithelia (Caco-2; unpublished observations). Thus, unlike ZOT, which affects only the small intestine, SEQ ID NO. 27 affects a broader spectrum of epithelia and, unlike *Clostridium perfringens* enterotoxin, causes no discernable cell damage. Thus, SEQ ID NO. 27 can be used to survey a variety of tissues to identify common regulatory mechanisms.

In summary, SEQ ID NO. 27 is a channel-forming peptide that reversibly modulates conductance through the epithelial paracellular pathway. The response is fully repeatable and occurs without overt indications of cytotoxicity. This functionality provides a unique opportunity to conduct research regarding the mechanisms that selectively modulate tight junction maintenance. Additionally, SEQ ID NO. 27 represents a novel lead compound that might be developed to augment other forms of therapy that are currently limited by the epithelial barrier.

We claim:

1. An isolated synthetic peptide having a total of from about 16-31 amino acid residues and comprising a plurality of polar amino acid residues at either the N- or C-terminus of said peptide and at least two modules individually and respectively selected from the group consisting of A, B, a, b, A', and a', said A module comprising SEQ ID No. 48, said B module comprising SEQ ID No. 49, said a module comprising SEQ ID No. 50, said b module comprising SEQ ID No. 51, said A' module comprising SEQ ID No. 52, and said a' module comprising SEQ ID No. 53.

2. The peptide of claim 1, said plurality of polar amino acid residues including at least one lysine residue.

3. The peptide of claim 1, said plurality of polar amino acid residues comprising up to four lysine residues.

4. The peptide of claim 1, said peptide having from about 22-27 amino acid residues.

5. The peptide of claim 1, said peptide being substantially monomeric in solution.

6. The peptide of claim 1, said peptide being soluble to a level of at least about maybe 1 mM.

7. The peptide of claim 1, said peptide being soluble to a level of at least about 10 mM.

8. The peptide of claim 1, said peptide having at least about 35% helical content.

9. The peptide of claim 1, said peptide having an activity profile of greater than about 15.0 µA/cm2 in MDCK cells when applied to the MDCK cells at a concentration of about 500 µM.

10. The peptide of claim 1, said peptide including at least one amino acid residue positioned between said modules.

11. The peptide of claim 1, said at least one amino acid residue positioned between said modules being selected from the group consisting of alanine, lysine, and tryptophan.

12. The isolated synthetic peptide of claim 1, said peptide being selected from the group consisting of SEQ ID Nos. 27, 26, 19, 18, 28, 9, 13, 4, 32, and 34.

* * * * *

SEQUENCE LISTING

```
<160> NUMBER OF SEQ ID NOS: 55

<210> SEQ ID NO 1
<211> LENGTH: 23
<212> TYPE: PRT
<213> ORGANISM: Homo sapiens

<400> SEQUENCE: 1

Pro Ala Arg Val Gly Leu Gly Ile Thr Thr Val Leu Thr Met Thr Thr
1               5                   10                  15

Gln Ser Ser Gly Ser Arg Ala
            20

<210> SEQ ID NO 2
<211> LENGTH: 27
<212> TYPE: PRT
<213> ORGANISM: Modified Homo sapiens

<400> SEQUENCE: 2

Pro Ala Arg Val Gly Leu Gly Ile Thr Thr Val Leu Thr Met Thr Thr
1               5                   10                  15

Gln Ser Ser Gly Ser Arg Ala Lys Lys Lys Lys
            20                  25

<210> SEQ ID NO 3
<211> LENGTH: 27
<212> TYPE: PRT
<213> ORGANISM: Modified Homo sapiens

<400> SEQUENCE: 3

Lys Lys Lys Lys Pro Ala Arg Val Gly Leu Gly Ile Thr Thr Val Leu
1               5                   10                  15

Thr Met Thr Thr Gln Ser Ser Gly Ser Arg Ala
            20                  25

<210> SEQ ID NO 4
<211> LENGTH: 27
<212> TYPE: PRT
<213> ORGANISM: Modified Homo sapiens

<400> SEQUENCE: 4

Lys Lys Lys Lys Ala Arg Ser Gly Ser Ser Gln Thr Thr Met Thr Leu
1               5                   10                  15

Val Thr Thr Ile Gly Leu Gly Val Arg Ala Ala
            20                  25
```

```
<210> SEQ ID NO 5
<211> LENGTH: 27
<212> TYPE: PRT
<213> ORGANISM: Modified Homo sapiens

<400> SEQUENCE: 5

Lys Lys Lys Lys Val Thr Thr Ile Gly Leu Gly Val Arg Ala Pro Leu
1               5                   10                  15

Val Thr Thr Ile Gly Leu Gly Val Arg Ala Ala
            20                  25

<210> SEQ ID NO 6
<211> LENGTH: 27
<212> TYPE: PRT
<213> ORGANISM: Modified Homo sapiens

<400> SEQUENCE: 6

Lys Lys Lys Lys Thr Met Thr Thr Gln Ser Ser Gly Ser Arg Ala Leu
1               5                   10                  15

Thr Met Thr Thr Gln Ser Ser Gly Ser Arg Ala
            20                  25

<210> SEQ ID NO 7
<211> LENGTH: 27
<212> TYPE: PRT
<213> ORGANISM: Modified Homo sapiens

<400> SEQUENCE: 7

Lys Lys Lys Lys Thr Met Thr Thr Gln Ser Ser Gly Ser Arg Ala Leu
1               5                   10                  15

Val Thr Thr Ile Gly Leu Gly Val Arg Ala Ala
            20                  25

<210> SEQ ID NO 8
<211> LENGTH: 27
<212> TYPE: PRT
<213> ORGANISM: Modified Homo sapiens

<400> SEQUENCE: 8

Lys Lys Lys Lys Val Thr Thr Ile Gly Leu Gly Val Arg Ala Pro Leu
1               5                   10                  15

Ala Arg Ser Gly Ser Ser Gln Thr Thr Met Thr
            20                  25

<210> SEQ ID NO 9
<211> LENGTH: 27
<212> TYPE: PRT
<213> ORGANISM: Modified Homo sapiens

<400> SEQUENCE: 9

Lys Lys Lys Lys Ala Ala Arg Val Gly Leu Gly Ile Thr Thr Val Trp
1               5                   10                  15

Val Thr Thr Ile Gly Leu Gly Val Arg Ala Ala
            20                  25

<210> SEQ ID NO 10
<211> LENGTH: 27
<212> TYPE: PRT
<213> ORGANISM: Modified Homo sapiens
```

-continued

```
<400> SEQUENCE: 10

Lys Lys Lys Lys Pro Ala Arg Val Gly Leu Gly Ile Thr Thr Val Trp
1               5                   10                  15

Thr Met Thr Thr Gln Ser Ser Gly Ser Arg Ala
            20                  25

<210> SEQ ID NO 11
<211> LENGTH: 27
<212> TYPE: PRT
<213> ORGANISM: Modified Homo sapiens

<400> SEQUENCE: 11

Lys Lys Lys Lys Pro Ala Arg Val Gly Leu Gly Ile Thr Thr Val Thr
1               5                   10                  15

Thr Met Thr Thr Gln Ser Ser Gly Ser Arg Ala
            20                  25

<210> SEQ ID NO 12
<211> LENGTH: 28
<212> TYPE: PRT
<213> ORGANISM: Modified Homo sapiens

<400> SEQUENCE: 12

Lys Lys Lys Lys Pro Ala Arg Val Gly Leu Gly Ile Thr Thr Val Leu
1               5                   10                  15

Thr Met Thr Thr Gln Ser Ser Gly Ser Arg Ala Trp
            20                  25

<210> SEQ ID NO 13
<211> LENGTH: 22
<212> TYPE: PRT
<213> ORGANISM: Modified Homo sapiens

<400> SEQUENCE: 13

Lys Lys Lys Lys Pro Ala Arg Val Gly Leu Gly Ile Thr Thr Val Leu
1               5                   10                  15

Thr Met Thr Thr Arg Ser
            20

<210> SEQ ID NO 14
<211> LENGTH: 22
<212> TYPE: PRT
<213> ORGANISM: Modified Homo sapiens

<400> SEQUENCE: 14

Lys Lys Lys Lys Pro Ala Arg Val Gly Leu Gly Ile Thr Thr Val Leu
1               5                   10                  15

Thr Met Thr Thr Gln Arg
            20

<210> SEQ ID NO 15
<211> LENGTH: 22
<212> TYPE: PRT
<213> ORGANISM: Modified Homo sapiens

<400> SEQUENCE: 15

Lys Lys Lys Lys Pro Ala Arg Val Gly Leu Gly Ile Thr Thr Val Leu
1               5                   10                  15

Thr Arg Thr Thr Gln Ser
            20
```

-continued

```
<210> SEQ ID NO 16
<211> LENGTH: 27
<212> TYPE: PRT
<213> ORGANISM: Modified Homo sapiens

<400> SEQUENCE: 16

Lys Lys Lys Lys Ala Arg Ser Gly Ser Ser Gln Thr Thr Met Thr Leu
1               5                   10                  15

Val Thr Thr Ile Gly Leu Gly Val Arg Ala Pro
            20                  25

<210> SEQ ID NO 17
<211> LENGTH: 27
<212> TYPE: PRT
<213> ORGANISM: Modified Homo sapiens

<400> SEQUENCE: 17

Ala Arg Ser Gly Ser Ser Gln Thr Thr Met Thr Leu Val Thr Thr Ile
1               5                   10                  15

Gly Leu Gly Val Arg Ala Pro Lys Lys Lys Lys
            20                  25

<210> SEQ ID NO 18
<211> LENGTH: 27
<212> TYPE: PRT
<213> ORGANISM: Modified Homo sapiens

<400> SEQUENCE: 18

Lys Lys Lys Lys Pro Ala Arg Val Gly Leu Gly Ile Thr Thr Val Leu
1               5                   10                  15

Val Thr Thr Ile Gly Leu Gly Val Arg Ala Pro
            20                  25

<210> SEQ ID NO 19
<211> LENGTH: 27
<212> TYPE: PRT
<213> ORGANISM: Modified Homo sapiens

<400> SEQUENCE: 19

Pro Ala Arg Val Gly Leu Gly Ile Thr Thr Val Leu Val Thr Thr Ile
1               5                   10                  15

Gly Leu Gly Val Arg Ala Pro Lys Lys Lys Lys
            20                  25

<210> SEQ ID NO 20
<211> LENGTH: 27
<212> TYPE: PRT
<213> ORGANISM: Modified Homo sapiens

<400> SEQUENCE: 20

Lys Lys Lys Lys Pro Ala Arg Val Gly Leu Gly Ile Thr Thr Val Leu
1               5                   10                  15

Pro Ala Arg Val Gly Leu Gly Ile Thr Thr Val
            20                  25

<210> SEQ ID NO 21
<211> LENGTH: 27
<212> TYPE: PRT
<213> ORGANISM: Modified Homo sapiens
```

```
<400> SEQUENCE: 21

Lys Lys Lys Lys Pro Ala Arg Val Gly Leu Gly Ile Thr Thr Val Leu
1               5                   10                  15

Ala Ala Arg Val Gly Leu Gly Ile Thr Thr Val
            20                  25

<210> SEQ ID NO 22
<211> LENGTH: 27
<212> TYPE: PRT
<213> ORGANISM: Modified Homo sapiens

<400> SEQUENCE: 22

Lys Lys Lys Lys Val Thr Thr Ile Gly Leu Gly Val Arg Ala Pro Leu
1               5                   10                  15

Pro Ala Arg Val Gly Leu Gly Ile Thr Thr Val
            20                  25

<210> SEQ ID NO 23
<211> LENGTH: 27
<212> TYPE: PRT
<213> ORGANISM: Modified Homo sapiens

<400> SEQUENCE: 23

Lys Lys Lys Lys Ala Arg Ser Gly Ser Ser Gln Thr Thr Met Thr Leu
1               5                   10                  15

Thr Met Thr Thr Gln Ser Ser Gly Ser Arg Ala
            20                  25

<210> SEQ ID NO 24
<211> LENGTH: 27
<212> TYPE: PRT
<213> ORGANISM: Modified Homo sapiens

<400> SEQUENCE: 24

Lys Lys Lys Lys Thr Met Thr Thr Gln Ser Ser Gly Ser Arg Ala Leu
1               5                   10                  15

Ala Arg Ser Gly Ser Ser Gln Thr Thr Met Thr
            20                  25

<210> SEQ ID NO 25
<211> LENGTH: 27
<212> TYPE: PRT
<213> ORGANISM: Modified Homo sapiens

<400> SEQUENCE: 25

Lys Lys Lys Lys Ala Arg Ser Gly Ser Ser Gln Thr Thr Met Thr Leu
1               5                   10                  15

Ala Arg Ser Gly Ser Ser Gln Thr Thr Met Thr
            20                  25

<210> SEQ ID NO 26
<211> LENGTH: 27
<212> TYPE: PRT
<213> ORGANISM: Modified Homo sapiens

<400> SEQUENCE: 26

Lys Lys Lys Lys Pro Ala Arg Val Gly Leu Gly Ile Thr Thr Val Leu
1               5                   10                  15

Val Thr Thr Ile Gly Leu Gly Val Arg Ala Ala
            20                  25
```

<210> SEQ ID NO 27
<211> LENGTH: 27
<212> TYPE: PRT
<213> ORGANISM: Modified Homo sapiens

<400> SEQUENCE: 27

Lys Lys Lys Lys Ala Ala Arg Val Gly Leu Gly Ile Thr Thr Val Leu
1               5                   10                  15

Val Thr Thr Ile Gly Leu Gly Val Arg Ala Ala
            20                  25

<210> SEQ ID NO 28
<211> LENGTH: 26
<212> TYPE: PRT
<213> ORGANISM: Modified Homo sapiens

<400> SEQUENCE: 28

Lys Lys Lys Lys Ala Ala Arg Val Gly Leu Gly Ile Thr Thr Val Val
1               5                   10                  15

Thr Thr Ile Gly Leu Gly Val Arg Ala Ala
            20                  25

<210> SEQ ID NO 29
<211> LENGTH: 28
<212> TYPE: PRT
<213> ORGANISM: Modified Homo sapiens

<400> SEQUENCE: 29

Lys Lys Lys Lys Ala Ala Arg Val Gly Leu Gly Ile Thr Thr Val Leu
1               5                   10                  15

Leu Val Thr Thr Ile Gly Leu Gly Val Arg Ala Ala
            20                  25

<210> SEQ ID NO 30
<211> LENGTH: 29
<212> TYPE: PRT
<213> ORGANISM: Modified Homo sapiens

<400> SEQUENCE: 30

Lys Lys Lys Lys Ala Ala Arg Val Gly Leu Gly Ile Thr Thr Val Leu
1               5                   10                  15

Leu Leu Val Thr Thr Ile Gly Leu Gly Val Arg Ala Ala
            20                  25

<210> SEQ ID NO 31
<211> LENGTH: 30
<212> TYPE: PRT
<213> ORGANISM: Modified Homo sapiens

<400> SEQUENCE: 31

Lys Lys Lys Lys Ala Ala Arg Val Gly Leu Gly Ile Thr Thr Val Leu
1               5                   10                  15

Leu Leu Leu Val Thr Thr Ile Gly Leu Gly Val Arg Ala Ala
            20                  25                  30

<210> SEQ ID NO 32
<211> LENGTH: 22
<212> TYPE: PRT
<213> ORGANISM: Modified Homo sapiens
<220> FEATURE:
<221> NAME/KEY: misc_feature
<222> LOCATION: (21)..(21)
<223> OTHER INFORMATION: X is Di-aminopimelic acid

```
<400> SEQUENCE: 32

Lys Lys Lys Lys Pro Ala Arg Val Gly Leu Gly Ile Thr Thr Val Leu
1               5                   10                  15

Thr Arg Thr Thr Xaa Ser
            20

<210> SEQ ID NO 33
<211> LENGTH: 25
<212> TYPE: PRT
<213> ORGANISM: Modified Homo sapiens

<400> SEQUENCE: 33

Lys Lys Lys Lys Pro Ala Arg Val Gly Leu Gly Ile Thr Thr Val Leu
1               5                   10                  15

Thr Met Thr Thr Gln Ser Ser Gly Ser
            20                  25

<210> SEQ ID NO 34
<211> LENGTH: 22
<212> TYPE: PRT
<213> ORGANISM: Modified Homo sapiens

<400> SEQUENCE: 34

Lys Lys Lys Lys Pro Ala Arg Val Gly Leu Gly Ile Thr Thr Val Leu
1               5                   10                  15

Thr Met Thr Thr Gln Ser
            20

<210> SEQ ID NO 35
<211> LENGTH: 21
<212> TYPE: PRT
<213> ORGANISM: Modified Homo sapiens

<400> SEQUENCE: 35

Lys Lys Lys Lys Pro Ala Arg Val Gly Leu Gly Ile Thr Thr Val Leu
1               5                   10                  15

Thr Met Thr Thr Gln
            20

<210> SEQ ID NO 36
<211> LENGTH: 20
<212> TYPE: PRT
<213> ORGANISM: Modified Homo sapiens

<400> SEQUENCE: 36

Lys Lys Lys Lys Pro Ala Arg Val Gly Leu Gly Ile Thr Thr Val Leu
1               5                   10                  15

Thr Met Thr Thr
            20

<210> SEQ ID NO 37
<211> LENGTH: 19
<212> TYPE: PRT
<213> ORGANISM: Modified Homo sapiens

<400> SEQUENCE: 37

Lys Lys Lys Lys Pro Ala Arg Val Gly Leu Gly Ile Thr Thr Val Leu
1               5                   10                  15

Thr Met Thr
```

```
<210> SEQ ID NO 38
<211> LENGTH: 18
<212> TYPE: PRT
<213> ORGANISM: Modified Homo sapiens

<400> SEQUENCE: 38

Lys Lys Lys Lys Pro Ala Arg Val Gly Leu Gly Ile Thr Thr Val Leu
1               5                   10                  15

Thr Met

<210> SEQ ID NO 39
<211> LENGTH: 17
<212> TYPE: PRT
<213> ORGANISM: Modified Homo sapiens

<400> SEQUENCE: 39

Lys Lys Lys Lys Pro Ala Arg Val Gly Leu Gly Ile Thr Thr Val Leu
1               5                   10                  15

Thr

<210> SEQ ID NO 40
<211> LENGTH: 16
<212> TYPE: PRT
<213> ORGANISM: Modified Homo sapiens

<400> SEQUENCE: 40

Lys Lys Lys Lys Pro Ala Arg Val Gly Leu Gly Ile Thr Thr Val Leu
1               5                   10                  15

<210> SEQ ID NO 41
<211> LENGTH: 25
<212> TYPE: PRT
<213> ORGANISM: Modified Homo sapiens

<400> SEQUENCE: 41

Arg Val Gly Leu Gly Ile Thr Thr Val Leu Thr Met Thr Thr Gln Ser
1               5                   10                  15

Ser Gly Ser Arg Ala Lys Lys Lys Lys
            20                  25

<210> SEQ ID NO 42
<211> LENGTH: 23
<212> TYPE: PRT
<213> ORGANISM: Modified Homo sapiens

<400> SEQUENCE: 42

Gly Leu Gly Ile Thr Thr Val Leu Thr Met Thr Thr Gln Ser Ser Gly
1               5                   10                  15

Ser Arg Ala Lys Lys Lys Lys
            20

<210> SEQ ID NO 43
<211> LENGTH: 22
<212> TYPE: PRT
<213> ORGANISM: Modified Homo sapiens

<400> SEQUENCE: 43

Leu Gly Ile Thr Thr Val Leu Thr Met Thr Thr Gln Ser Ser Gly Ser
1               5                   10                  15

Arg Ala Lys Lys Lys Lys
            20
```

-continued

```
<210> SEQ ID NO 44
<211> LENGTH: 21
<212> TYPE: PRT
<213> ORGANISM: Modified Homo sapiens

<400> SEQUENCE: 44

Gly Ile Thr Thr Val Leu Thr Met Thr Thr Gln Ser Ser Gly Ser Arg
1               5                   10                  15

Ala Lys Lys Lys Lys
            20

<210> SEQ ID NO 45
<211> LENGTH: 20
<212> TYPE: PRT
<213> ORGANISM: Modified Homo sapiens

<400> SEQUENCE: 45

Ile Thr Thr Val Leu Thr Met Thr Thr Gln Ser Ser Gly Ser Arg Ala
1               5                   10                  15

Lys Lys Lys Lys
            20

<210> SEQ ID NO 46
<211> LENGTH: 16
<212> TYPE: PRT
<213> ORGANISM: Modified Homo sapiens

<400> SEQUENCE: 46

Leu Thr Met Thr Thr Gln Ser Ser Gly Ser Arg Ala Lys Lys Lys Lys
1               5                   10                  15

<210> SEQ ID NO 47
<211> LENGTH: 31
<212> TYPE: PRT
<213> ORGANISM: Modified Homo sapiens

<400> SEQUENCE: 47

Lys Lys Lys Lys Pro Ala Arg Val Gly Leu Gly Ile Thr Thr Val Leu
1               5                   10                  15

Thr Met Thr Thr Gln Ser Ser Gly Ser Arg Ala Lys Lys Lys Lys
            20                  25                  30

<210> SEQ ID NO 48
<211> LENGTH: 11
<212> TYPE: PRT
<213> ORGANISM: Modified Homo sapiens

<400> SEQUENCE: 48

Pro Ala Arg Val Gly Leu Gly Ile Thr Thr Val
1               5                   10

<210> SEQ ID NO 49
<211> LENGTH: 11
<212> TYPE: PRT
<213> ORGANISM: Modified Homo sapiens

<400> SEQUENCE: 49

Thr Met Thr Thr Gln Ser Ser Gly Ser Arg Ala
1               5                   10

<210> SEQ ID NO 50
<211> LENGTH: 11
<212> TYPE: PRT
<213> ORGANISM: Modified Homo sapiens
```

```
<400> SEQUENCE: 50

Val Thr Thr Ile Gly Leu Gly Val Arg Ala Pro
1               5                  10

<210> SEQ ID NO 51
<211> LENGTH: 11
<212> TYPE: PRT
<213> ORGANISM: Modified Homo sapiens

<400> SEQUENCE: 51

Ala Arg Ser Gly Ser Ser Gln Thr Thr Met Thr
1               5                  10

<210> SEQ ID NO 52
<211> LENGTH: 11
<212> TYPE: PRT
<213> ORGANISM: Modified Homo sapiens

<400> SEQUENCE: 52

Ala Ala Arg Val Gly Leu Gly Ile Thr Thr Val
1               5                  10

<210> SEQ ID NO 53
<211> LENGTH: 11
<212> TYPE: PRT
<213> ORGANISM: Modified Homo sapiens

<400> SEQUENCE: 53

Val Thr Thr Ile Gly Leu Gly Val Arg Ala Ala
1               5                  10

<210> SEQ ID NO 54
<211> LENGTH: 22
<212> TYPE: PRT
<213> ORGANISM: Modified Homo sapiens

<400> SEQUENCE: 54

Lys Lys Lys Lys Pro Ala Arg Val Gly Leu Gly Ile Thr Thr Val Leu
1               5                  10                  15

Thr Met Thr Thr Gln Trp
            20

<210> SEQ ID NO 55
<211> LENGTH: 22
<212> TYPE: PRT
<213> ORGANISM: Modified Homo sapiens

<400> SEQUENCE: 55

Lys Lys Lys Lys Pro Ala Arg Val Gly Leu Gly Ile Thr Thr Val Leu
1               5                  10                  15

Thr Met Thr Thr Arg Trp
            20
```